US006921654B2

(12) United States Patent
Abu-Threideh et al.

(10) Patent No.: US 6,921,654 B2
(45) Date of Patent: Jul. 26, 2005

(54) ISOLATED HUMAN KINASE PROTEINS, NUCLEIC ACID MOLECULES ENCODING HUMAN KINASE PROTEINS, AND USES THEREOF

(75) Inventors: Jane Abu-Threideh, Germantown, MD (US); Beena Neelam, Gaithersburg, MD (US); Chunhua Yan, Boyds, MD (US)

(73) Assignee: Applera Corporation, Norwalk, CT (US)

( * ) Notice: Subject to any disclaimer, the term of this patent is extended or adjusted under 35 U.S.C. 154(b) by 129 days.

(21) Appl. No.: 10/429,873

(22) Filed: May 6, 2003

(65) Prior Publication Data

US 2004/0014193 A1 Jan. 22, 2004

Related U.S. Application Data

(60) Provisional application No. 60/380,134, filed on May 6, 2002.

(51) Int. Cl.$^7$ ............................ C12N 9/20; C12N 1/20; C12N 15/00; C12N 5/00; C12Q 1/68

(52) U.S. Cl. .................... 435/194; 435/320.1; 435/325; 435/252.3; 435/6; 536/23.2

(58) Field of Search ......................... 435/194, 6, 252.3, 435/325, 320.1; 536/23.2

(56) References Cited

U.S. PATENT DOCUMENTS 5,858,662 A 1/1999 Keating et al.
2002/0110811 A1 8/2002 Levine et al.

OTHER PUBLICATIONS

Results of BLAST Search of SEQ ID No.:2 against Derwent (FastAlertP and GENESEQP) and NCBI (pataa) protein patent databases on Sep. 8, 2004 (60 pages).

Sumi et al. "Cofilin Phosphorylation and Actin Cytoskeletal Dymanics Regulated by Rho– and Cdc42–Activated Lim–Kinase 2." Journal of Cell Biol. 1999. vol. 147, pp. 1519–1532.

Mizuno et al. "Identification of a Human cDNA Encoding a Novel Protein Kinase with Two Repeats of the LIM/Double Zinc Finger Motif." Oncogene. 1994. vol. 9, pp. 1605–1612.

Yang et al. "Cofilin Phosphorylation by LIM–Kinase 1 and its Role in Rac–Mediated Actin Reorganization." Naturem. 1998. vol. 393, pp. 809–812.

International Search report dated Dec. 2, 2003.

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

16 Claims, 29 Drawing Sheets

```
   1 ATGCTGTTGG CTTCAGCCCC AAGAAGACGC CGCTTCCTCC AGAGGGCTAA
  51 GTGTTGTGAC TGCAGTGCCT CCCTGTCGCA CCAGTACTAT GAGAAGGATG
 101 GGCAGCTCTT CTGCAAGAAG GACTACTGGG CCCGCTATGG CGAGTCCTGC
 151 CATGGGTGCT CTGAGCAAAT CACCAAGGGA CTGGTTATGG TGGCTGGGGA
 201 GCTGAAGTAC CACCCCGAGT GTTTCATCTG CCTCACGTGT GGGACCTTTA
 251 TCGGTGACGG GGACACCTAC ACGCTGGTGG AGCACTCCAA GCTGTACTGC
 301 GGGCACTGCT ACTACCAGAC TGTGGTGACC CCCGTCATCG AGCAGATCCT
 351 GCCTGACTCC CCTGGCTCCC ACCTGCCCCA CACCGTCACC CTGGTGTCCA
 401 TCCCAGCCTC ATCTCATGGC AAGCGTGGAC TTTCAGTCTC CATTGACCCC
 451 CCGCACGGCC CACCGGGCTG TGGCACCGAG CACTCACACA CCGTCCGCGT
 501 CCAGGGAGTG GATCCGGGCT GCATGAGCCC AGATGTGAAG AATTCCATCC
 551 ACGTCGGAGA CCGGATCTTG GAAATCAATG GCACGCCCAT CCGAAATGTG
 601 CCCCTGGACG AGATTGACCT GCTGATTCAG GAAACCAGCC GCCTGCTCCA
 651 GCTGACCCTC GAGCATGACC CTCACGATAC ACTGGGCCAC GGGCTGGGGC
 701 CTGAGACCAG CCCCCTGAGC TCTCCGGCTT ATACTCCCAG CGGGGAGGCG
 751 GGCAGCTCTG CCCGGCAGAA ACCTGTCTTG AGGAGCTGCA GCATCGACAG
 801 GTCTCCGGGC GCTGGCTCAC TGGGCTCCCC GGCCTCCCAG CGCAAGGACC
 851 TGGGTCGCTC TGAGTCCCTC CGCGTAGTCT GCCGGCCACA CCGCATCTTC
 901 CGGCCGTCGG ACCTCATCCA CGGGGAGGTG CTGGGCAAGG GCTGCTTCGG
 951 CCAGGCTATC AAGGTGACAC ACCGTGAGAC AGGTGAGGTG ATGGTGATGA
1001 AGGAGCTGAT CCGGTTCGAC GAGGAGACCC AGAGGACGTT CCTCAAGGAG
1051 GTGAAGGTCA TGCGATGCCT GGAACACCCC AACGTGCTCA AGTTCATCGG
1101 GGTGCTCTAC AAGGACAAGA GGCTCAACTT CATCACTGAG TACATCAAGG
1151 GCGGCACGCT CCGGGGCATC ATCAAGAGCA TGGACAGCCA GTACCCATGG
1201 AGCCAGAGAG TGAGCTTTGC CAAGGACATC GCATCAGGGA TGGCCTACCT
1251 CCACTCCATG AACATCATCC ACCGAGACCT CAACTCCCAC AACTGCCTGG
1301 TCCGCGAGAA CAAGAATGTG GTGGTGGCTG ACTTCGGGCT GGCGCGTCTC
1351 ATGGTGGACG AGAAGACTCA GCCTGAGGGC CTGCGGAGCC TCAAGAAGCC
1401 AGACCGCAAG AAGCGCTACA CCGTGGTGGG CAACCCCTAC TGGATGGCAC
1451 CTGAGATGAT CAACGGCCGC AGCTATGATG AGAAGGTGGA TGTGTTCTCC
1501 TTTGGGATCG TCCTGTGCGA GATCATCGGG CGGGTGAACG CAGACCCTGA
1551 CTACCTGCCC CGCACCATGG ACTTTGGCCT CAACGTGCGA GGATTCCTGG
1601 ACCGCTACTG CCCCCCAAAC TGCCCCCCGA GCTTCTTCCC CATCACCGTG
1651 CGCTGTTGCG ATCTGGACCC CGAGAAGAGG CCATCCTTTG TGAAGCTGGA
1701 ACACTGGCTG GAGACCCTCC GCATGCACCT GGCCGGCCAC CTGCCACTGG
1751 GCCCACAGCT GGAGCAGCTG GACAGAGGTT TCTGGGAGAC CTACCGGCGC
1801 GGCGAGAGCG GACTGCCTGC CCACCCTGAG GTCCCCGACT GA   (SEQ ID NO:1)
```

FEATURES:
Start Codon: 1
Stop Codon: 1840

Homologous proteins:
<u>Top 10 BLAST Hits</u>

| | Score | E |
|---|---|---|
| CRA\|18000004927819 /altid=gi\|4505001 /def=ref\|NP_002305.1\| (NM_... | 1265 | 0.0 |
| CRA\|18000005039311 /altid=gi\|3915762 /def=sp\|P53667\|LIK1_HUMAN ... | 1264 | 0.0 |
| CRA\|18000005039312 /altid=gi\|1432165 /def=gb\|AAB17546.1\| (U6229... | 1264 | 0.0 |
| CRA\|60000046724506 /altid=gi\|13929022 /def=ref\|NP_113915.1\| (NM... | 1206 | 0.0 |
| CRA\|18000005009110 /altid=gi\|6754548 /def=ref\|NP_034847.1\| (NM_... | 1203 | 0.0 |
| CRA\|18000004977241 /altid=gi\|595790 /def=gb\|AAC52147.1\| (U14166... | 1200 | 0.0 |
| CRA\|18000004932934 /altid=gi\|2137473 /def=pir\|\|I49125 limk - mo... | 1188 | 0.0 |
| CRA\|224000022362238 /altid=gi\|19912219 /def=dbj\|BAB88398.1\| (AB... | 1045 | 0.0 |
| CRA\|18000005090462 /altid=gi\|2257461 /def=dbj\|BAA21488.1\| (AB00... | 869 | 0.0 |
| CRA\|18000004975714 /altid=gi\|1708823 /def=sp\|P53666\|LIK2_CHICK ... | 672 | 0.0 |

FIGURE 1A

Blast hits to dbEST:

| CRA Number | gi Number | Score | Expect |
|---|---|---|---|
| CRA\|158000041255634 | gi\|10990732 | 1453 bits (733) | 0.0 |
| CRA\|56000140040876 | gi\|14651066 | 1413 bits (713) | 0.0 |
| CRA\|225000000775189 | gi\|15492241 | 1374 bits (693) | 0.0 |
| CRA\|147000075477821 | gi\|15580946 | 1366 bits (689) | 0.0 |
| CRA\|223000003453028 | gi\|16042298 | 1352 bits (682) | 0.0 |
| CRA\|107000020219172 | gi\|9327826 | 1257 bits (634) | 0.0 |
| CRA\|11000545317047 | gi\|9134163 | 1247 bits (629) | 0.0 |
| CRA\|118000029444304 | gi\|10932273 | 1229 bits (620) | 0.0 |
| CRA\|36000074884881 | gi\|11100188 | 1217 bits (614) | 0.0 |
| CRA\|164000029941830 | gi\|11003193 | 1172 bits (591) | 0.0 |
| CRA\|11000545322294 | gi\|9134646 | 1172 bits (591) | 0.0 |
| CRA\|147000075485035 | gi\|15581205 | 1168 bits (589) | 0.0 |
| CRA\|225000015179653 | gi\|18519638 | 1112 bits (561) | 0.0 |
| CRA\|148000005476758 | gi\|8750745 | 1045 bits (527) | 0.0 |
| CRA\|225000015228570 | gi\|18524085 | 1031 bits (520) | 0.0 |
| CRA\|164000139375205 | gi\|12676216 | 955 bits (482) | 0.0 |
| CRA\|11000545309216 | gi\|9133441 | 924 bits (466) | 0.0 |
| CRA\|11000545345459 | gi\|9136803 | 910 bits (459) | 0.0 |
| CRA\|11000545318389 | gi\|9134287 | 844 bits (426) | 0.0 |
| CRA\|78000169224832 | gi\|14064335 | 775 bits (391) | 0.0 |
| CRA\|1000488774272 | gi\|5130935 | 773 bits (390) | 0.0 |

EXPRESSION INFORMATION FOR MODULATORY USE:
library source:

| gi Number | Organ | Tissue Type |
|---|---|---|
| gi\|10990732 | (none) | (none) |
| gi\|14651066 | brain | neuroblastoma |
| gi\|15492241 | brain | hypothalamus |
| gi\|15580946 | brain | hypothalamus |
| gi\|16042298 | liver | adenocarcinoma, cell line |
| gi\|9327826 | brain | neuroblastoma |
| gi\|9134163 | brain | neuroblastoma |
| gi\|10932273 | (none) | whole embryo, mainly head |
| gi\|11100188 | brain | neuroblastoma |
| gi\|11003193 | (none) | thyroid gland |
| gi\|9134646 | brain | neuroblastoma |
| gi\|15581205 | brain | hypothalamus |
| gi\|18519638 | uterus | leiomyosarcoma |
| gi\|8750745 | kidney | renal cell adenocarcinoma |
| gi\|18524085 | small intestine | duodenal adenocarcinoma, cell line |
| gi\|12676216 | kidney | hypernephroma, cell line |
| gi\|9133441 | brain | neuroblastoma |
| gi\|9136803 | brain | neuroblastoma |
| gi\|9134287 | brain | neuroblastoma |
| gi\|14064335 | eye | normal pigmented retinal epithelium |
| gi\|5130935 | Hip | Bone |

FIGURE 1B

```
  1 MLLASAPRRR RFLQRAKCCD CSASLSHQYY EKDGQLFCKK DYWARYGESC
 51 HGCSEQITKG LVMVAGELKY HPECFICLTC GTFIGDGDTY TLVEHSKLYC
101 GHCYYQTVVT PVIEQILPDS PGSHLPHTVT LVSIPASSHG KRGLSVSIDP
151 PHGPPGCGTE HSHTVRVQGV DPGCMSPDVK NSIHVGDRIL EINGTPIRNV
201 PLDEIDLLIQ ETSRLLQLTL EHDPHDTLGH GLGPETSPLS SPAYTPSGEA
251 GSSARQKPVL RSCSIDRSPG AGSLGSPASQ RKDLGRSESL RVVCRPHRIF
301 RPSDLIHGEV LGKGCFGQAI KVTHRETGEV MVMKELIRFD EETQRTFLKE
351 VKVMRCLEHP NVLKFIGVLY KDKRLNFITE YIKGGTLRGI IKSMDSQYPW
401 SQRVSFAKDI ASGMAYLHSM NIIHRDLNSH NCLVRENKNV VVADFGLARL
451 MVDEKTQPEG LRSLKKPDRK KRYTVVGNPY WMAPEMINGR SYDEKVDVFS
501 FGIVLCEIIG RVNADPDYLP RTMDFGLNVR GFLDRYCPPN CPPSFFPITV
551 RCCDLDPEKR PSFVKLEHWL ETLRMHLAGH LPLGPQLEQL DRGFWETYRR
601 GESGLPAHPE VPD  (SEQ ID NO:2)
```

FEATURES:
Functional domains and key regions:
<u>Prosite results:</u>

PDOC00004 PS00004 CAMP_PHOSPHO_SITE
cAMP- and cGMP-dependent protein kinase phosphorylation site
Number of matches: 2

| | | |
|---|---|---|
| 1 | 471-474 | KRYT |
| 2 | 559-562 | KRPS |

PDOC00005 PS00005 PKC_PHOSPHO_SITE
Protein kinase C phosphorylation site
Number of matches: 13

| | | |
|---|---|---|
| 1 | 164-166 | TVR |
| 2 | 212-214 | TSR |
| 3 | 253-255 | SAR |
| 4 | 279-281 | SQR |
| 5 | 289-291 | SLR |
| 6 | 323-325 | THR |
| 7 | 343-345 | TQR |
| 8 | 386-388 | TLR |
| 9 | 401-403 | SQR |
| 10 | 463-465 | SLK |
| 11 | 549-551 | TVR |
| 12 | 572-574 | TLR |
| 13 | 597-599 | TYR |

PDOC00006 PS00006 CK2_PHOSPHO_SITE
Casein kinase II phosphorylation site
Number of matches: 4

| | | |
|---|---|---|
| 1 | 91-94 | TLVE |
| 2 | 323-326 | THRE |
| 3 | 456-459 | TQPE |
| 4 | 491-494 | SYDE |

PDOC00007 PS00007 TYR_PHOSPHO_SITE
Tyrosine kinase phosphorylation site
Number of matches: 2

| | | |
|---|---|---|
| 1 | 392-398 | KSMDSQY |
| 2 | 511-518 | RVNADPDY |

FIGURE 2A

```
PDOC00008 PS00008 MYRISTYL
N-myristoylation site
Number of matches: 8
     1      34-39   GQLFCK
     2      81-86   GTFIGD
     3      143-148      GLSVSI
     4      158-163      GTEHSH
     5      169-174      GVDPGC
     6      275-280      GSPASQ
     7      385-390      GTLRGI
     8      502-507      GIVLCE

PDOC00009 PS00009 AMIDATION
Amidation site
            139-142      HGKR

PDOC00382 PS00478 LIM_DOMAIN_1
LIM domain signature
            50-84   CHGCSEQITKGLVMVAGELKYHPECFICLTCGTFI

PDOC00100 PS00107 PROTEIN_KINASE_ATP
Protein kinases ATP-binding region signature
            311-334      LGKGCFGQAIKVTHRETGEVMVMK
```

Membrane spanning structure and domains:

| Helix | Begin | End | Score | Certainty |
|---|---|---|---|---|
| 1 | 120 | 140 | 0.821 | Putative |

```
BLAST Alignment to Top Hit:
>CRA|18000004927819 /altid=gi|4505001 /def=ref|NP_002305.1|
          (NM_002314) LIM domain kinase 1 isoform 1; LIM
          motif-containing protein kinase [Homo sapiens] /org=Homo
          sapiens /taxon=9606 /div=PRI /dataset=nraa /length=647
         Length = 647

 Score = 1265 bits (3237), Expect = 0.0
 Identities = 596/597 (99%), Positives = 597/597 (99%)

Query: 17  KCCDCSASLSHQYYEKDGQLFCKKDYWARYGESCHGCSEQITKGLVMVAGELKYHPECFI 76
            +CCDCSASLSHQYYEKDGQLFCKKDYWARYGESCHGCSEQITKGLVMVAGELKYHPECFI
Sbjct: 51  RCCDCSASLSHQYYEKDGQLFCKKDYWARYGESCHGCSEQITKGLVMVAGELKYHPECFI 110

Query: 77  CLTCGTFIGDGDTYTLVEHSKLYCGHCYYQTVVTPVIEQILPDSPGSHLPHTVTLVSIPA 136
            CLTCGTFIGDGDTYTLVEHSKLYCGHCYYQTVVTPVIEQILPDSPGSHLPHTVTLVSIPA
Sbjct: 111 CLTCGTFIGDGDTYTLVEHSKLYCGHCYYQTVVTPVIEQILPDSPGSHLPHTVTLVSIPA 170

Query: 137 SSHGKRGLSVSIDPPHGPPGCGTEHSHTVRVQGVDPGCMSPDVKNSIHVGDRILEINGTP 196
            SSHGKRGLSVSIDPPHGPPGCGTEHSHTVRVQGVDPGCMSPDVKNSIHVGDRILEINGTP
Sbjct: 171 SSHGKRGLSVSIDPPHGPPGCGTEHSHTVRVQGVDPGCMSPDVKNSIHVGDRILEINGTP 230

Query: 197 IRNVPLDEIDLLIQETSRLLQLTLEHDPHDTLGHGLGPETSPLSSPAYTPSGEAGSSARQ 256
            IRNVPLDEIDLLIQETSRLLQLTLEHDPHDTLGHGLGPETSPLSSPAYTPSGEAGSSARQ
Sbjct: 231 IRNVPLDEIDLLIQETSRLLQLTLEHDPHDTLGHGLGPETSPLSSPAYTPSGEAGSSARQ 290

Query: 257 KPVLRSCSIDRSPGAGSLGSPASQRKDLGRSESLRVVCRPHRIFRPSDLIHGEVLGKGCF 316
            KPVLRSCSIDRSPGAGSLGSPASQRKDLGRSESLRVVCRPHRIFRPSDLIHGEVLGKGCF
Sbjct: 291 KPVLRSCSIDRSPGAGSLGSPASQRKDLGRSESLRVVCRPHRIFRPSDLIHGEVLGKGCF 350
```

FIGURE 2B

```
Query: 317 GQAIKVTHRETGEVMVMKELIRFDEETQRTFLKEVKVMRCLEHPNVLKFIGVLYKDKRLN 376
           GQAIKVTHRETGEVMVMKELIRFDEETQRTFLKEVKVMRCLEHPNVLKFIGVLYKDKRLN
Sbjct: 351 GQAIKVTHRETGEVMVMKELIRFDEETQRTFLKEVKVMRCLEHPNVLKFIGVLYKDKRLN 410

Query: 377 FITEYIKGGTLRGIIKSMDSQYPWSQRVSFAKDIASGMAYLHSMNIIHRDLNSHNCLVRE 436
           FITEYIKGGTLRGIIKSMDSQYPWSQRVSFAKDIASGMAYLHSMNIIHRDLNSHNCLVRE
Sbjct: 411 FITEYIKGGTLRGIIKSMDSQYPWSQRVSFAKDIASGMAYLHSMNIIHRDLNSHNCLVRE 470

Query: 437 NKNVVVADFGLARLMVDEKTQPEGLRSLKKPDRKKRYTVVGNPYWMAPEMINGRSYDEKV 496
           NKNVVVADFGLARLMVDEKTQPEGLRSLKKPDRKKRYTVVGNPYWMAPEMINGRSYDEKV
Sbjct: 471 NKNVVVADFGLARLMVDEKTQPEGLRSLKKPDRKKRYTVVGNPYWMAPEMINGRSYDEKV 530

Query: 497 DVFSFGIVLCEIIGRVNADPDYLPRTMDFGLNVRGFLDRYCPPNCPPSFFPITVRCCDLD 556
           DVFSFGIVLCEIIGRVNADPDYLPRTMDFGLNVRGFLDRYCPPNCPPSFFPITVRCCDLD
Sbjct: 531 DVFSFGIVLCEIIGRVNADPDYLPRTMDFGLNVRGFLDRYCPPNCPPSFFPITVRCCDLD 590

Query: 557 PEKRPSFVKLEHWLETLRMHLAGHLPLGPQLEQLDRGFWETYRRGESGLPAHPEVPD 613  (residues 17-
613 of SEQ ID NO:2)
           PEKRPSFVKLEHWLETLRMHLAGHLPLGPQLEQLDRGFWETYRRGESGLPAHPEVPD
Sbjct: 591 PEKRPSFVKLEHWLETLRMHLAGHLPLGPQLEQLDRGFWETYRRGESGLPAHPEVPD 647  (SEQ ID NO:4)
```

Hmmer search results (Pfam):

Scores for sequence family classification (score includes all domains):

| Model | Description | Score | E-value | N |
|---|---|---|---|---|
| pkinase | Protein kinase domain | 226.5 | 3.7e-64 | 1 |
| LIM | LIM domain | 81.9 | 1.3e-20 | 2 |
| PDZ | PDZ domain (Also known as DHR or GLGF). | 70.5 | 3.6e-17 | 1 |
| zf-PARP | Poly(ADP-ribose) polymerase and DNA-Ligase Z | -22.7 | 1.3 | 1 |

Parsed for domains:

| Model | Domain | seq-f | seq-t | | hmm-f | hmm-t | | score | E-value |
|---|---|---|---|---|---|---|---|---|---|
| LIM | 1/2 | 8 | 47 | .. | 1 | 61 | [] | 10.1 | 0.0032 |
| LIM | 2/2 | 50 | 109 | .. | 1 | 61 | [] | 80.0 | 4.8e-20 |
| zf-PARP | 1/1 | 42 | 117 | .. | 1 | 94 | [] | -22.7 | 1.3 |
| PDZ | 1/1 | 131 | 223 | .. | 1 | 83 | [] | 70.5 | 3.6e-17 |
| pkinase | 1/1 | 305 | 563 | .. | 1 | 269 | [. | 226.5 | 3.7e-64 |

Support for alt 5' end:

LTI:

>TA_5310385: /fpmclibrary=NFLHAL1 /fpmc=19600411981129
Length = 3026

Score = 5905 bits (2979), Expect = 0.0
Identities = 2995/3003 (99%)
Strand = Plus / Plus

```
Query: 1   gaagcagctggtctggccacccctgccctcccttagacctccagagcccccagtgtagcc 60
           ||||||||||||||||||||||||||||||||||||||||||||||||||||||||||||
Sbjct: 24  gaagcagctggtctggccacccctgccctcccttagacctccagagcccccagtgtagcc 83

Query: 61  acagaggatgctgttggcttcagccccaagaagacgccgcttcctccagagggctaagtg 120
           ||||||||||||||||||||||||||||||||||||||||||||||||||||||||||||
Sbjct: 84  acagaggatgctgttggcttcagccccaagaagacgccgcttcctccagagggctaagtg 143
```

FIGURE 2C

```
Query: 121  ttgtgactgcagtgcctccctgtcgcaccagtactatgagaaggatgggcagctcttctg 180
            ||||||||||||||||||||||||||||||||||||||||||||||||||||||||||||
Sbjct: 144  ttgtgactgcagtgcctccctgtcgcaccagtactatgagaaggatgggcagctcttctg 203

Query: 181  caagaaggactactgggcccgctatggcgagtcctgccatgggtgctctgagcaaatcac 240
            ||||||||||||||||||||||||||||||||||||||||||||||||||||||||||||
Sbjct: 204  caagaaggactactgggcccgctatggcgagtcctgccatgggtgctctgagcaaatcac 263

Query: 241  caagggactggttatggtggctggggagctgaagtaccaccccgagtgtttcatctgcct 300
            ||||||||||||||||||||||||||||||||||||||||||||||||||||||||||||
Sbjct: 264  caagggactggttatggtggctggggagctgaagtaccaccccgagtgtttcatctgcct 323

Query: 301  cacgtgtgggacctttatcggtgacggggacacctacacgctggtggagcactccaagct 360
            ||||||||||||||||||||||||||||||||||||||||||||||||||||||||||||
Sbjct: 324  cacgtgtgggacctttatcggtgacggggacacctacacgctggtggagcactccaagct 383

Query: 361  gtactgcgggcactgctactaccagactgtggtgacccccgtcatcgagcagatcctgcc 420
            ||||||||||||||||||||||||||||||||||||||||||||||||||||||||||||
Sbjct: 384  gtactgcgggcactgctactaccagactgtggtgacccccgtcatcgagcagatcctgcc 443

Query: 421  tgactcccctggctcccacctgccccacaccgtcaccctggtgtccatcccagcctcatc 480
            ||||||||||||||||||||||||||||||||||||||||||||||||||||||||||||
Sbjct: 444  tgactcccctggctcccacctgccccacaccgtcaccctggtgtccatcccagcctcatc 503

Query: 481  tcatggcaagcgtggactttcagtctccattgacccccgcacggcccaccgggctgtgg 540
            ||||||||||||||||||||||||||||||||||||||||||||||||||||||||||||
Sbjct: 504  tcatggcaagcgtggactttcagtctccattgacccccgcacggcccaccgggctgtgg 563

Query: 541  caccgagcactcacacaccgtccgcgtccagggagtggatccgggctgcatgagcccaga 600
            ||||||||||||||||||||||||||||||||||||||||||||||||||||||||||||
Sbjct: 564  caccgagcactcacacaccgtccgcgtccagggagtggatccgggctgcatgagcccaga 623

Query: 601  tgtgaagaattccatccacgtcggagaccggatcttggaaatcaatggcacgcccatccg 660
            ||||||||||||||||||||||||||||||||||||||||||||||||||||||||||||
Sbjct: 624  tgtgaagaattccatccacgtcggagaccggatcttggaaatcaatggcacgcccatccg 683

Query: 661  aaatgtgcccctggacgagattgacctgctgattcaggaaaccagccgcctgctccagct 720
            ||||||||||||||||||||||||||||||||||||||||||||||||||||||||||||
Sbjct: 684  aaatgtgcccctggacgagattgacctgctgattcaggaaaccagccgcctgctccagct 743

Query: 721  gaccctcgagcatgaccctcacgatacactgggccacgggctggggcctgagaccagccc 780
            ||||||||||||||||||||||||||||||||||||||||||||||||||||||||||||
Sbjct: 744  gaccctcgagcatgaccctcacgatacactgggccacgggctggggcctgagaccagccc 803

Query: 781  cctgagctctccggcttatactcccagcggggaggcgggcagctctgcccggcagaaacc 840
            ||||||||||||||||||||||||||||||||||||||||||||||||||||||||||||
Sbjct: 804  cctgagctctccggcttatactcccagcggggaggcgggcagctctgcccggcagaaacc 863
```

FIGURE 2D

```
Query: 841  tgtcttgaggagctgcagcatcgacaggtctccgggcgctggctcactgggctccccggc 900
            ||||||||||||||||||||||||||||||||||||||||||||||||||||||||||||
Sbjct: 864  tgtcttgaggagctgcagcatcgacaggtctccgggcgctggctcactgggctccccggc 923

Query: 901  ctcccagcgcaaggacctgggtcgctctgagtccctccgcgtagtctgccggccacaccg 960
            ||||||||||||||||||||||||||||||||||||||||||||||||||||||||||||
Sbjct: 924  ctcccagcgcaaggacctgggtcgctctgagtccctccgcgtagtctgccggccacaccg 983

Query: 961  catcttccggccgtcggacctcatccacggggaggtgctgggcaagggctgcttcggcca 1020
            ||||||||||||||||||||||||||||||||||||||||||||||||||||||||||||
Sbjct: 984  catcttccggccgtcggacctcatccacggggaggtgctgggcaagggctgcttcggcca 1043

Query: 1021 ggctatcaaggtgacacaccgtgagacaggtgaggtgatggtgatgaaggagctgatccg 1080
            ||||||||||||||||||||||||||||||||||||||||||||||||||||||||||||
Sbjct: 1044 ggctatcaaggtgacacaccgtgagacaggtgaggtgatggtgatgaaggagctgatccg 1103

Query: 1081 gttcgacgaggagacccagaggacgttcctcaaggaggtgaaggtcatgcgatgcctgga 1140
            ||||||||||||||||||||||||||||||||||||||||||||||||||||||||||||
Sbjct: 1104 gttcgacgaggagacccagaggacgttcctcaaggaggtgaaggtcatgcgatgcctgga 1163

Query: 1141 acaccccaacgtgctcaagttcatcggggtgctctacaaggacaagaggctcaacttcat 1200
            ||||||||||||||||||||||||||||||||||||||||||||||||||||||||||||
Sbjct: 1164 acaccccaacgtgctcaagttcatcggggtgctctacaaggacaagaggctcaacttcat 1223

Query: 1201 cactgagtacatcaagggcggcacgctccggggcatcatcaagagcatggacagccagta 1260
            ||||||||||||||||||||||||||||||||||||||||||||||||||||||||||||
Sbjct: 1224 cactgagtacatcaagggcggcacgctccggggcatcatcaagagcatggacagccagta 1283

Query: 1261 cccatggagccagagagtgagctttgccaaggacatcgcatcagggatggcctacctcca 1320
            ||||||||||||||||||||||||||||||||||||||||||||||||||||||||||||
Sbjct: 1284 cccatggagccagagagtgagctttgccaaggacatcgcatcagggatggcctacctcca 1343

Query: 1321 ctccatgaacatcatccaccgagacctcaactcccacaactgcctggtccgcgagaacaa 1380
            ||||||||||||||||||||||||||||||||||||||||||||||||||||||||||||
Sbjct: 1344 ctccatgaacatcatccaccgagacctcaactcccacaactgcctggtccgcgagaacaa 1403

Query: 1381 gaatgtggtggtggctgacttcgggctggcgcgtctcatggtggacgagaagactcagcc 1440
            ||||||||||||||||||||||||||||||||||||||||||||||||||||||||||||
Sbjct: 1404 gaatgtggtggtggctgacttcgggctggcgcgtctcatggtggacgagaagactcagcc 1463

Query: 1441 tgagggcctgcggagcctcaagaagccagaccgcaagaagcgctacaccgtggtgggcaa 1500
            ||||||||||||||||||||||||||||||||||||||||||||||||||||||||||||
Sbjct: 1464 tgagggcctgcggagcctcaagaagccagaccgcaagaagcgctacaccgtggtgggcaa 1523
```

FIGURE 2E

```
Query: 1501 cccctactggatggcacctgagatgatcaacggccgcagctatgatgagaaggtggatgt 1560
            ||||||||||||||||||||||||||||||||||||||||||||||||||||||||||||
Sbjct: 1524 cccctactggatggcacctgagatgatcaacggccgcagctatgatgagaaggtggatgt 1583

Query: 1561 gttctcctttgggatcgtcctgtgcgagatcatcgggcgggtgaacgcagaccctgacta 1620
            ||||||||||||||||||||||||||||||||||||||||||||||||||||||||||||
Sbjct: 1584 gttctcctttgggatcgtcctgtgcgagatcatcgggcgggtgaacgcagaccctgacta 1643

Query: 1621 cctgccccgcaccatggactttggcctcaacgtgcgaggattcctggaccgctactgccc 1680
            ||||||||||||||||||||||||||||||||||||||||||||||||||||||||||||
Sbjct: 1644 cctgccccgcaccatggactttggcctcaacgtgcgaggattcctggaccgctactgccc 1703

Query: 1681 cccaaactgcccccgagcttcttccccatcaccgtgcgctgttgcgatctggaccccga 1740
            ||||||||||||||||||||||||||||||||||||||||||||||||||||||||||||
Sbjct: 1704 cccaaactgcccccgagcttcttccccatcaccgtgcgctgttgcgatctggaccccga 1763

Query: 1741 gaagaggccatcctttgtgaagctggaacactggctggagaccctccgcatgcacctggc 1800
            ||||||||||||||||||||||||||||||||||||||||||||||||||||||||||||
Sbjct: 1764 gaagaggccatcctttgtgaagctggaacactggctggagaccctccgcatgcacctggc 1823

Query: 1801 cggccacctgccactgggcccacagctggagcagctggacagaggtttctgggagaccta 1860
            ||||||||||||||||||||||||||||||||||||||||||||||||||||||||||||
Sbjct: 1824 cggccacctgccactgggcccacagctggagcagctggacagaggtttctgggagaccta 1883

Query: 1861 ccggcgcggcgagagcggactgcctgcccaccctgaggtccccgactgagccagggccac 1920
            ||||||||||||||||||||||||||||||||||||||||||||||||||||||||||||
Sbjct: 1884 ccggcgcggcgagagcggactgcctgcccaccctgaggtccccgactgagccagggccac 1943

Query: 1921 tcagctgcccctgtccccacctctggagaatccacccccaccagattcctccgcgggagg 1980
            ||||||||||||||||||||||||||||||||||||||||||||||||||||||||||||
Sbjct: 1944 tcagctgcccctgtccccacctctggagaatccacccccaccagattcctccgcgggagg 2003

Query: 1981 tggccctcagctgggacagtggggacccaggcttctcctcagagccaggccctgacttgc 2040
            ||||||||||||||||||||||||||||||||||||||||||||||||||||||||||||
Sbjct: 2004 tggccctcagctgggacagtggggacccaggcttctcctcagagccaggccctgacttgc 2063

Query: 2041 cttctcccaccccgtggaccgcttcccctgccttctctctgccgtggcccagagccggcc 2100
            ||||||||||||||||||||||||||||||||||||||||||||||||||||||||||||
Sbjct: 2064 cttctcccaccccgtggaccgcttcccctgccttctctctgccgtggcccagagccggcc 2123

Query: 2101 cagctgcacacacacaccatgctctcgccctgctgtaacctctgtcttggcagggctgtc 2160
            ||||||||||||||||||||||||||||||||||||||||||||||||||||||||||||
Sbjct: 2124 cagctgcacacacacaccatgctctcgccctgctgtaacctctgtcttggcagggctgtc 2183

Query: 2161 ccctcttgcttctccttgcatgagctggagggcctgtgtgagttacgcccctttccacac 2220
            ||||||||||||||||||||||||||||||||||||||||||||||||||||||||||||
Sbjct: 2184 ccctcttgcttctccttgcatgagctggagggcctgtgtgagttacgcccctttccacac 2243
```

FIGURE 2F

```
Query: 2221 gccgctgccccagcaaccctgttcacgctccacctgtctggtccatagctccctggaggc 2280
            ||||||||||||||||||||||||||||||||||||||||||||||||||||||||||||
Sbjct: 2244 gccgctgccccagcaaccctgttcacgctccacctgtctggtccatagctccctggaggc 2303

Query: 2281 tgggccaggaggcagcctccgaaccatgccccatataacgcttgggtgcgtgggagggcg 2340
            ||||||||||||||||||||||||||||||||||||||||||||||||||||||||||||
Sbjct: 2304 tgggccaggaggcagcctccgaaccatgccccatataacgcttgggtgcgtgggagggcg 2363

Query: 2341 cacatcagggcagaggccaagttccaggtgtctgtgttcccaggaaccaaatggggagtc 2400
            ||||||||||||||||||||||||||||||||||||||||||||||||||||||||||||
Sbjct: 2364 cacatcagggcagaggccaagttccaggtgtctgtgttcccaggaaccaaatggggagtc 2423

Query: 2401 tggggcccgttttcccccccagggggtgtctaggtagcaacaggtatcgaggactctccaa 2460
            ||||||||||||||||||||||||||||||||||||||||||||||||||||||||||||
Sbjct: 2424 tggggcccgttttcccccccagggggtgtctaggtagcaacaggtatcgaggactctccaa 2483

Query: 2461 acccccaaagcagagagagggctgatcccatggggcggaggtccccagtggctgagcaaa 2520
            ||||||||||||||||||||||||||||||||||||||||||||||||||||||||||||
Sbjct: 2484 acccccaaagcagagagagggctgatcccatggggcggaggtccccagtggctgagcaaa 2543

Query: 2521 cagccccttctctcgctttgggtcnnnnnnnngtttctttcttaaagccactttagtgag 2580
            ||||||||||||||||||||||||        ||||||||||||||||||||||||||||
Sbjct: 2544 cagccccttctctcgctttgggtcttttttttgtttctttcttaaagccactttagtgag 2603

Query: 2581 aagcaggtaccaagcctcagggtgaagggggtcccttgagggagcgtggagctgcggtgc 2640
            ||||||||||||||||||||||||||||||||||||||||||||||||||||||||||||
Sbjct: 2604 aagcaggtaccaagcctcagggtgaagggggtcccttgagggagcgtggagctgcggtgc 2663

Query: 2641 cctggccggcgatggggaggagccggctccggcagtgagaggataggcacagtggaccgg 2700
            ||||||||||||||||||||||||||||||||||||||||||||||||||||||||||||
Sbjct: 2664 cctggccggcgatggggaggagccggctccggcagtgagaggataggcacagtggaccgg 2723

Query: 2701 gcaggtgtccaccagcagctcagcccctgcagtcatctcagagccccttcccgggcctct 2760
            ||||||||||||||||||||||||||||||||||||||||||||||||||||||||||||
Sbjct: 2724 gcaggtgtccaccagcagctcagcccctgcagtcatctcagagccccttcccgggcctct 2783

Query: 2761 cccccaaggctccctgcccctcctcatgcccctctgtcctctgcgtttttttctgtgtaat 2820
            ||||||||||||||||||||||||||||||||||||||||||||||||||||||||||||
Sbjct: 2784 cccccaaggctccctgcccctcctcatgcccctctgtcctctgcgtttttttctgtgtaat 2843

Query: 2821 ctattttttaagaagagtttgtattattttttcatacggctgcagcagcagctgccaggg 2880
            ||||||||||||||||||||||||||||||||||||||||||||||||||||||||||||
Sbjct: 2844 ctattttttaagaagagtttgtattattttttcatacggctgcagcagcagctgccaggg 2903
```

FIGURE 2G

```
Query: 2881 gcttgggattttatttttgtggcgggcgggggtgggagggccattttgtcactttgcctc 2940
            ||||||||||||||||||||||||||||||||||||||||||||||||||||||||||||
Sbjct: 2904 gcttgggattttatttttgtggcgggcgggggtgggagggccattttgtcactttgcctc 2963

Query: 2941 agttgagcatctaggaagtattaaaactgtgaagctttctcagtgcactttgaacctgga 3000
            ||||||||||||||||||||||||||||||||||||||||||||||||||||||||||||
Sbjct: 2964 agttgagcatctaggaagtattaaaactgtgaagctttctcagtgcactttgaacctgga 3023

Query: 3001 aaa 3003  (SEQ ID NO:5)
            |||
Sbjct: 3024 aaa 3026  (SEQ ID NO:6)

CHGI:
>CRA|232000027972124 /altid=TA|1219172 /dataset=chgi_v5 /def=NOT
          ASSIGNED /taxon=9606 /org=Homo sapiens
          /fasta_sequence_orientation_wrt_asm=Forward
          /predicted_transcript_orientation_wrt_asm=Forward
         Length = 1226

 Score = 1493 bits (753), Expect = 0.0
 Identities = 814/824 (98%), Gaps = 9/824 (1%)
 Strand = Plus / Plus

Query: 1    gaagcagctggtctggccacccctgccctcccttagacctccagagcccccagtgtagcc 60
            ||||||||||||||||||||||||||||||||||||||||||||||||||||||||||||
Sbjct: 24   gaagcagctggtctggccacccctgccctcccttagacctccagagcccccagtgtagcc 83

Query: 61   acagaggatgctgttggcttcagccccaagaagacgccgcttcctccagagggctaagtg 120
            ||||||||||||||||||||||||||||||||||||||||||||||||||||||||||||
Sbjct: 84   acagaggatgctgttggcttcagccccaagaagacgccgcttcctccagagggctaagtg 143

Query: 121  ttgtgactgcagtgcctccctgtcgcaccagtactatgagaaggatgggcagctcttctg 180
            ||||||||||||||||||||||||||||||||||||||||||||||||||||||||||||
Sbjct: 144  ttgtgactgcagtgcctccctgtcgcaccagtactatgagaaggatgggcagctcttctg 203

Query: 181  caagaaggactactgggcccgctatggcgagtcctgccatgggtgctctgagcaaatcac 240
            ||||||||||||||||||||||||||||||||||||||||||||||||||||||||||||
Sbjct: 204  caagaaggactactgggcccgctatggcgagtcctgccatgggtgctctgagcaaatcac 263

Query: 241  caagggactggttatggtggctggggagctgaagtaccaccccgagtgtttcatctgcct 300
            ||||||||||||||||||||||||||||||||||||||||||||||||||||||||||||
Sbjct: 264  caagggactggttatggtggctggggagctgaagtaccaccccgagtgtttcatctgcct 323

Query: 301  cacgtgtgggacctttatcggtgacggggacacctacacgctggtggagcactccaagct 360
            ||||||||||||||||||||||||||||||||||||||||||||||||||||||||||||
Sbjct: 324  cacgtgtgggacctttatcggtgacggggacacctacacgctggtggagcactccaagct 383
```

FIGURE 2H

```
Query: 361 gtactgcgggcactgctactaccagactgtggtgaccccgtcatcgagcagatcctgcc 420
           ||||||||||||||||||||||||||||||||||||||||||||||||||||||||||||
Sbjct: 384 gtactgcgggcactgctactaccagactgtggtgaccccgtcatcgagcagatcctgcc 443

Query: 421 tgactcccctggctcccacctgccccacaccgtcaccctggtgtccatcccagcctcatc 480
           ||||||||||||||||||||||||||||||||||||||||||||||||||||||||||||
Sbjct: 444 tgactcccctggctcccacctgccccacaccgtcaccctggtgtccatcccagcctcatc 503

Query: 481 tcatggcaagcgtggactttcagtctccattgacccccgcacggcccaccgggctgtgg 540
           |||||||||||||||||||||||||||||||||||||||||||||||||||||||||||
Sbjct: 504 tcatggcaagcgtggactttcagtctccattgacccccgcacggcccaccgggctgtgg 563

Query: 541 caccgagcactcacacaccgtccgcgtccagggagtggatccgggctgcatgagcccaga 600
           ||||||||||||||||||||||||||||||||||||||||||||||||||||||||||||
Sbjct: 564 caccgagcactcacacaccgtccgcgtccagggagtggatccgggctgcatgagcccaga 623

Query: 601 tgtgaagaattccatccacgtcggagaccggatcttggaaatcaatggcacgcccatccg 660
           ||||||||||||||||||||||||||||||||||||||||||||||||||||||||||||
Sbjct: 624 tgtgaagaattccatccacgtcggagaccggatcttggaaatcaatggcacgcccatccg 683

Query: 661 aaatgtgcccctggacgagattgacctgctgattcaggaaaccagccgc-ctgctccag- 718
           |||||||||||||||||||||||| |||||||||||||||||||||||| |||||||||
Sbjct: 684 aaatgtgcccctggacgagattga-ctgctgattcaggaaaccagccgcactgctccaga 742

Query: 719 ctgaccctcgagcatgaccctcacgatac-actgggccacg--ggctggggcc-tgagac 774
           ||||||||||||||||||||||||||||| |||||| ||||  |||||||||| ||||||
Sbjct: 743 ctgaccctcgagcatgaccctcacgatacaactgggacacggcggctggggccttgagac 802

Query: 775 cag-ccccctgag-ctctccggcttatactcccagcggggaggc 816   (SEQ ID NO:7)
           ||| ||||||||| ||||||||||||||||||||||||||||||
Sbjct: 803 cagcccccctgagactctccggcttatactcccagcggggaggc 846   (SEQ ID NO:8)
```

FIGURE 2I

1 CAAAGTGCTG GGATTACAGG CGTGAGCCAC CGTGCCCGGC AATATTAAAG
51 CGATTTTAAG GCCAAGGCTG GTAACTCACG CCTGTAATCC CAGCACTTTG
101 GGAGGCTGAG GCAGGAGGAC TGCTTGAGGC CAGGAGTTTG AGATCAACCT
151 AGGCAACATA GTGAGACTCC ATCTCTACAA AAAAATTAGC CAGGCGTGGT
201 GGTGCGTACC TGTAGTCCCA GCTACTCAGG AGGCTGAGAT GGGAGGATCA
251 TTTGAACCCA GGATGTCGAA GCTGCAGTGA GCTGTGATCA CGCCACTGCA
301 CTCTGGCCTG GGCAACAGAG CGAGACACTG TCTCAAATTT TTAAAAAGCG
351 ATTTTACAAA TGAGGTGCAG AGTTCAGTCA CTTGCCAAAA GTCTCACAGC
401 GCGTGAGGAG TAGAATCAGG ACTCGAACCG AGGCAGCCTG GCTTCAGAGC
451 CTACAGTGTA ACCACAGCTT AGTCCCACAC CTCCCAGACC AACAGGGTCC
501 CTGCCTTCTA GTGGGCAAGA CACTCAGTGA ACAAATGTAG TGTCAGGTAT
551 TGGGGGACAG CACTCTCAGG AAGTGATGTT TAAGGGACAG AATTGAAGGG
601 AGCAGTGTTT AGAGGATGTC GGGGGTAGGG CCGGTGCATG TGCAAAGGCC
651 TTGGGGTGGG AATGTGCTTG GCACAACTGA GGACCACAAA GCCAGCGTGC
701 GGGAGTGCAG TCAGTGGCCA GGGGTGCATA GAGCCTTGTG GGCCCCGTGG
751 AAGGTGCCGT TGGCTGTACA GCTTTTTTTT TTTTTTTTTT TTTTTTTTTT
801 TGAGACAGAG TCTCGCTTTT GTTGCCCAGG CTGGAGTGCA GTGGCGTGAT
851 CTCAGCTCAC TGCAACCTCC GCCTCCCGGG TTCAAGCGAT TCTCCTGCCT
901 CAGCTTCCTG GTAGCTGGGA CTACAGGCGC CCACCACCAC ACCTGGCTAA
951 TTTTTGTGTT TTTAATAGAG ACGGGGTTTC ACCATGTTAG CCAGGCTGGC
1001 CTCAAACTCC TGACCTCAAG CGATCTGTCT ACCTCAGCCT CCCAAAGTGC
1051 TGGGGTTACA GGCATGAGCC ACTGCGCACA GGCAGCTGTG CATCTTTGAA
1101 TGTCATAACC TGAGCATCTG AGAGCTGCTC CTGTCCCCTG GCCCCTGCTC
1151 TTGAGGAAGT CCCACGCTGA TAGGACAGAC AGGGTCATAA GTGCTGTGAT
1201 GGGGGCCTGC AGGCTGCTGG AGGGCTCAGC CGGGACCAGA TGCTGCCCCT
1251 CTTTGTAGAG TGGGACAATT GCTGCAGGCC CATGGGACCT CTGGTATTAG
1301 CCCTGAGGGT TGTCACTCCG GGGCCTGCCC CTTTCTGTGT TCTGACCTCC
1351 CAGCCCCTTG CAGGCCCCGC CTCCCGGAAG GTTATGACCA GGCTTGGACT
1401 GGTCCAGGCT TCCCTTTGGC TCACATACTG CCTCTGCGAG GTCCCCTCCA
1451 GGAAGCCTCC TGTGCACAAC CCCCAGGGCT GCCGCATCCC TGGTAGCATC
1501 TCCTTGGCAG CTGGGTGGGC TGGCCCTGGG CAAGGAGGGC TGAGCATGCT
1551 GCTGGCCTGT GGGGTTGGAG CAGCGGCGGG ATGCAACCTC CCTTTCTTCA
1601 GGGGACCTTT TTGGCGAAGA CAAACTGTCC ATAGGAAGTC GACCTCTGTT
1651 CCCTTGGGGG CAGCAGTGGA AGAGGCAGCT GCTTTTGAGC TTGTCCCTGT
1701 CCCCAGAGAA GCCTGAGGCC TTCAGTGCCG TTGCCAGGGC CGAGGCTGAG
1751 GAGCCTACAG CGTGTGTTCA GGACTGAGGG CCAGGGACGG GCCACAGGCT
1801 CCCTGCCTGG GGTCCAAGCC TAGATCGCTC GCTCCCCACC CGCACCAAAG
1851 CCCAGGCAAA GGGTGCTTCA GCCACTTCCT GTTGCAGGCT CAGACCAAGT
1901 CCCCTGGCAC CCACGCGGCT GCAGCCTCCT CCTGTGCGCT GCAGCCACGC
1951 TGGCCCCACC CTCTGCAGCC TCCAATCCTG AGCCCCTGAG GGAGGATGGG
2001 GAAGCAGCTG GTCTGGCCAC CCCTGCCCTC CCTTAGACCT CCAGAGCCCC
2051 CAGTGTAGCC ACAGAGGATG CTGTTGGCTT CAGCCCCAAG AAGACGCCGC
2101 TTCCTCCAGA GGGCTAAGTA AGTGGGAATC CCCCTCCCTA CTTGTCCTGG
2151 GCTCCAGGCA GGGCCCCTGG TGTAAGGCCT GGGGCTGGAA GCCGACCCAC
2201 CTAGGTCCAG GCTCTGGGGC AGAACTGAAA CTCCTTGGTT ACTGTCGGCT
2251 GCAGCCTGGG AGCAGGCCAC TGCCAAAGCT GTGGGTCCTT CCAGGACAGT
2301 CTCCCCATGA GGCCGGTCCT CCACCTGCTG TTTCTTCACA CCTGGTGGCC
2351 AGGGATGTGG CCCTGGGTAG AACGATGATT CTCCACTCCT GTCATTATGG
2401 AAGCCACCGC TGTCTCCCAG CCCAGCCAGC CACCTGGGCT GCAGAGCACC
2451 CCTTTCATGC CCTCCGGGTG CCTCCCCCTT CTCCTGCCCC AGCCTGGCTT
2501 TGTCCTACCC TGCTCTCAGG GAGGGGTACC CTGGAGTGGG GCCAGGGCAT
2551 GGCTCTCCCC CGAGGGAGTT CCTCTCTGGC TGTCCCCAGG GCAGCTCTGC
2601 ACAGCCTCAG TACCTGGCGC ACCTCCCTTG ACATCCTTCT TAGGGACAGT
2651 CAGGCACTCT GTGTGGGGCA CTCAAGAGAG CCAGGCCCGT CAGCCTCTAG
2701 CTCCTGCCAG AATGCAGGCC TGAGGGGTGA GGGGCGGGGC AGGGGCAGGG
2751 GCAGGGACAG GAACTCCGGC GTGCTCTCCA TCCGCAAAGG TTCACTGAGG
2801 CCCCGAGCCC CAGCCACTGA GCCACCAAGT CAGCCTGGGC CAGGCCTGGG
2851 TGCCCTGTCT GCAATGGAGG CAGAGACGGG GTCTCGGGGC AGTTCTGAGG
2901 ATGCTGGGTG CACAGCGGGG GCCTCGCCGG CAGGAATCAC TTATGCTCTC

FIGURE 3A

2951 TCCTGGGCCA AGCTTTGTGG ATGCCCAGCC TGGGGCCGCG GGGAGCTGGC
3001 AGGTCAGTGG CAGACACTGG TGGGCAGACC TAGTGTCTGG TAGAACAGGC
3051 ATCAAGGAAG TGGTGACCGG AGGGAAGCCA AGTGCACTCA AACCCTCGGG
3101 TGAGTCATCA CCGCCGGGTC TTTCACAGCT GCTGAAAGTG AGCAACAGTG
3151 ATGAAGGTTT GTGAGTTTCT GCGTGAGCGA GTGAATGGAC CAGTAGCAGT
3201 TTCCAGGTTG TGGAAGAGCG TTCCCTCCCC GGGATGGGGA CACTTGGTTA
3251 CAGCAATTCC TAATCCCCCA CCCACCCACC GCCCACTGCA GAGGTATGCG
3301 GGGGCCCTGC TTCCTGCAGG CAGGAGTGAG GGGCACTCCT GTGATGTGGC
3351 ACCCCTGTGA CCGAGGTCAT GTGTGATCGG TGTAAGGGCA GGAAGCGAGT
3401 CATTGGTCTG CACCAGGCGT GGGGGCTTCT GCGAGGGCAG GACCCAAAGT
3451 CGGCCTGGCC TCCCGGCTGC AGCACTCCTT TCCCTTTCGA ATTAGGTTAG
3501 AGCCCTGGGA CGGGAGGTGC CCTGTAGACC ACCCCCCTCA CCAACTTCCG
3551 TCCTCCGCCC CACCCCCGCG GTGATCCGGT GAACTGCCGG CCCCCTGCTG
3601 TGCACCGAGT GGGGCAGTGA CCCTGACGTG GCGTCTCCTG CCGCCCCTGC
3651 CACCGCCACC ACCTCCGGTG GCCCAGCCTC CGCATTCCCC ACCCCCATGG
3701 AGGAATGCAC CAGGCCTCCC TTCCTGGATG CACCCCTCAC CCACATGCTT
3751 CCAAACCCTG GCATTTTCTG CTCCCCCTTT ACTCCCACCC CTTCCCCTAG
3801 GCTCCCAGAC AAAGGGGAAG TGGCTGGATC CTCTTAAAGG GACAGTGTCC
3851 CACCAGCTTA CTGCTGAACT CCCCTCCTCA ACCCCAGTTC CCTAGTTACA
3901 GTTAATTAGC ATTAGCAGAC AGCCCATGAG TGATACCCAT GCAGGCCCCA
3951 GGCTGTGGAG AGTTTCCTGG GTAGGAAACA GCCCTTAAGG TCCCTCATCT
4001 CATCCAGGTC CCAGTCTTTC CTACCTGCCT CTCTCCTAGA TTGTGGCCCT
4051 TTGGAGCCTG GTTCTTCTGT CCCTGTGTGA CCGACACATA GCACCCAAAC
4101 AGTGGCAGAG CGGGACGGAC CCCCTAGCCT GTTCTCTGTG TGGGTCTGTA
4151 CCCTGACCCA GACATGCCCC CCCACAGCAG GACCCAGGGG GGCACATGTG
4201 TGCCTGCGGG TTCACTGGGG CACCCGCATT TGGTTTATTT TATTTTTTAG
4251 AGAGAGGGTC TTGCTGTGTC ACCCAGCTGG AGTGCAGTGG TGTAATCATA
4301 GCACACTGCA GCCTTCAACT CCTGGGCTCA AGCGATCCTC CCTCCCCAGC
4351 CTCCCTAGTA GCTGGGAGTA CAGGACCCAC TGTATCCTGG CTAATTTTTT
4401 AATAATTTTT TAAGAGATGG GGTCTTACTG TGTTGCCCAG GCTGGCCTCA
4451 AACCTCTGGC CTCAAGTGAT CCTCCCACCT TCGCCTCCTG AAGTGCTGAG
4501 ATTACAGGCA TGAGCCACCA TGCCCATCCC AGACTGACAT TTCTATATTT
4551 GTTCATCCTG GCTGGGCAGG GCTGCTGGTC CCCACCCCAC CGGGATGCTT
4601 GGCTGGGAAA AAGCCGGGAA TGTAGGTCTA ACCCTGGCCT GTGTTGTGGC
4651 ACCTACAGCC TGGCATTCCT CCCCATCTGC CCTTCAAGGC CCCACCAACC
4701 AGGCCTCCTT GGTAGCCTCT AGTGAGGAAA CAGGCGAACC GTGGCTTTGA
4751 TGACCCTGCA CACCTGGGGA TTCTCCTCTA TTTTTCTTTT TCTTTTTTTT
4801 TTTTTTGGAG ACAGAGTCTC ACTCTGTCGC CAGGCTGGAG TGCAGTGGCA
4851 CAATTTTGGC TCACTGCAAC CTCTGCCTCC CAGGTTCAAG CGATTCTTCT
4901 GCCTCAGCCT CCCGAGTAGC TGGGATTACA GGTGCCCACC ACCATGCCTG
4951 GCTAGTTTTT GTATTTTTAG TGGAGACTGG GTTTTGCCAT GTTGGCCAGG
5001 CTGGTCTCAG ACTCCTGACC CCAAGTGATC TGCCCACCTC GGCCTCCCAA
5051 AGTGCTGGGA TTACAGGTGT GAGCCACCGC TTTGGGAGGC CGAGGTGGGC
5101 GGATCACGAG GTCAAGAGCT CAAGACCATC CTGGCCAAGA TGGTGAAACC
5151 CCATCTCTAC TAAAAATACA AAAAATTAGC TGGGCATGGT GGTGTGTGCC
5201 TGTAGTCCCA GCTACTCAGG AGGCTGAGGC AGGAGGATCA CTTGAACCTG
5251 GAAGGCAGAG GTTGCAGTGA GCCGAGATCG AGCCACTGCA CTGCAGCCTG
5301 GCGACAGAGC AAGACTCCGT CTCAAAAAAC AAACAAAAAG AAAACTTGTT
5351 CTAATTCTTA CAAAGGTGCC TGTAGCCGAG GCAGGGGCCC AGGTGAGGTG
5401 GAGGAGGGCG GGAGTGGACG TCTCAGCCCG GCCCCTCTCC TGCAGGTGTT
5451 GTGACTGCAG TGCCTCCCTG TCGCACCAGT ACTATGAGAA GGATGGGCAG
5501 CTCTTCTGCA AGAAGGACTA CTGGGCCCGC TATGGCGAGT CCTGCCATGG
5551 GTGCTCTGAG CAAATCACCA AGGGACTGGT TATGGTGAGC GCCCCCTGCC
5601 TTGCACACTC ACCTGGGGTG GGGGTATCCA AGCAGACCCC ATGCTCCAGG
5651 TCTCTCTCCC ATCATTGTCT CTCCTGGTCT CCTTTTTGCT GGTCTTTGGA
5701 GCTGCTTTCT GAGCCTGACT GTCTGTCTGT ATCCCTCAGC GCCCCCATCT
5751 ATGGAGCCAG CTCTGTCCAG GAGCTCAGCA GCTGGCCAGC CGGGTCCCTG
5801 CAGTTGTTTT TTTGGTGACA CCCTTGGAAG AGGCCTAGGG GAGGATCTGT
5851 GGGGGTTGTT GGGTCTGCTG AGCTGGGCTG TTCCCTCCTC ACCCCCGCAC

FIGURE 3B

5901 CAGGTGGCTG GGGAGCTGAA GTACCACCCC GAGTGTTTCA TCTGCCTCAC
5951 GTGTGGGACC TTTATCGGTG ACGGGGACAC CTACACGCTG GTGGAGCACT
6001 CCAAGCTGTA CTGGTGAGTG CCTTGGCCCC TCCCTGAGCC TAGGAGGCCC
6051 ACCTGTGTCA CAGATCTGCA AGGGTGCTGA CTCTCCCACA CCCGGGCCTC
6101 CTGCCCTTTC CCATGGGGTG AGGTTTGTTG GGGCAAATGT TCATATCTCC
6151 TTTCCCATCC CGGCATGGAA ACAAGTGAGA AATAACACAC AGAAGTCAGT
6201 GTGAAAAAGC CTCAGACGGC CAGGCATGCT GGCTCACGCC TGTAAACCCA
6251 GCACTTTGGG ATTCCGAGGT GGGTGGATCC CTTGAGGCTA GGAGTTCAAG
6301 ACCAGCCTGG CCAACATGGT GGAACCCCAT CTCTATTAAA AATACAAAAA
6351 TTAACCAGGT GTGGTGGCGG GTGCCTGTAA TCCCAGCTAC TCAGGAGGCT
6401 GAGGCAGGAG ACTCTCTTGA ACCTGGGAGG TGGAAGTTGC AGTGAGCCAA
6451 GATTGCACCA CTGCCCTCCA GCCTAGGCAA CAGAGCAAGA CTCTGTCTCA
6501 AAACAGAAAA CCTCAGACGT CAGCTTTCTT ACTGGCCATG ACTGCAGCAT
6551 GGTGCTGGCA CAAACCACCA GAGGTGGGGT GGATGCCACA AGTTAAGGAC
6601 ACCATCCCCA GCATAACTGC TCCCTCTTTA GACACCAGCC ACAAGTTCAG
6651 GGGTCCCCAA CCCACTCACA CTTCTGACCG ACTGGCTACA AATTCAGGGA
6701 CTCCCAAGAC CCTGCCAAGT TTGATCGTTT GCTAACAGAC TCACAGAACT
6751 CAGGAAATCC TCCATTTTTA TCCCAGTTTT ATTATGAAGG ACACAGCTCA
6801 GGTCCGACCA AATGAAGAAG CATCTCCCCT CCCTCCCCTA GCACATCAAT
6851 GTGATCACCA ACCAGGAAGC TTCACTGAGC TTCAGCAGCC AGAGTTTTTA
6901 TTGGGATTTC ATTACATCGT CATGACTGAT TGAGTCATTG GCCGTATGAT
6951 CAAGCTTAGT CTCTAGCCCC CGTTCTTGGA GGTCAGGCTG GATGAAAGCT
7001 GCAACCCTCT TCAAATCACA TGATGTATCT TTGCGGGGCT GAGTCATCTC
7051 ATTAGTATCA ACTCAGGAAT AGTCTGAGGG GCTCATGAAT AACAAAGATA
7101 CCCCATTCCA AGGACTTAGA GTCTCCCTCC CAGGAATCAG GACAAAACCC
7151 AGACAGATTC TTTCTTATAC AACACTGATC AAGCTGGATT AGAGGACAAC
7201 GTGGCTTGAT CCCAGATGGG CTTTTAATGA CTTCCTCCTG AACTGGATTT
7251 ATCCTCAGGC CTTGTCCTGG CCGCCTTACA GGATCACAGC GAGTAGACAG
7301 ACCCGAATGA CTCAGAGGGA CGAGGGCTGG CTGGGCACGC ACAGTTCCTG
7351 CTCCCAGTTC CATAGGAAGA GTGAAAGAAA AGAAAGCTGG CCAGGTGCAG
7401 TGGCTCACCC CTATAATCCC AGCACTTTGG GAGGCCAAGG CAGGCAGATC
7451 ACCTGAGGTC TGGAGTTTGA GGCCAGCCTG GCCAACATGG TGAAACCGTC
7501 TCTACTAAAA ATAAGAAATT AGCCAGGCAT GGTGGTGCGT GCCCGTAATC
7551 CCAGCTACTC AGGAGGCTGA GGCAGGAGAA TCGCTTGAAC CCAGGAGGCG
7601 GAGGTTACAG TGAGCCAAGA TCACACCACT GCACTTTTGG ACAATTGCTA
7651 GCTTTCCTTT TCTTTTGAGA CAGAGTCTTG CTTTGTCACC CAGGCTGGGG
7701 TGCAGTGTTG TAATCAACAG AGTGAGACTC CATCTCAAAA AAAAAAAAAA
7751 AAAGGAAGGG ATTGGGGGAA GAGCCTGGGG CTGGGGGCTG CAGAGATGCT
7801 GAAATTGATG ACGCCCTTGA CACTCTTTTC TTCCCACCCC GGCGGCTCTT
7851 GCAGCGGGCA CTGCTACTAC CAGACTGTGG TGACCCCCGT CATCGAGCAG
7901 ATCCTGCCTG ACTCCCCTGG CTCCCACCTG CCCCACACCG TCACCCTGGT
7951 GTCCATCCCA GCCTCATCTC ATGGCAAGCG TGGACTTTCA GTCTCCATTG
8001 ACCCCCCGCA CGGCCCACCG GGCTGTGGCA CCGAGCACTC ACACACCGTC
8051 CGCGTCCAGG GGTGAGTGGC CGGCCTGCCG AGGCTGCCGT CGGTGTGGCT
8101 ATGGCTGTTG ATGTGGGTGG CAGAGTCTGG CACTGGGGGC CCTGAAAATG
8151 AATGGGCGAG TGTTTGGGTA CAGATGGGGC CCAGTTCTGA CAACCTGGTT
8201 TGCCAGATTT CTGGCCCAGT CATTCCTCTG AATACCATTA CAAATGCCAG
8251 ATACAATAAA AAGACATTTT CAACCGGGCA TGGTGGCCCA CACCTGTAAT
8301 CTCAGCACTT CGGGAGGCCG AAGTGGGTGG ATCACCTGAG GTCAGGAGTT
8351 CGAGACCAGC CTGGGCAATG TGGTGAAACC CCGTCTCTAC TAAAAATACA
8401 AACGTAGCCA GGCATGGTAG TGTGTGCCTA TAGTGCCAGC TGCTTGGGAG
8451 GCTGAGGCAG GAGAATCACT TGAACCCAGG AGGTGGAGGT TTCAGTGAGC
8501 CCCGACTGCC ATTGCACTCC AGGCTGGGCA ACAAGAGTGT AACTCTGTAT
8551 CAAAAAAATA AAAATAAAAA AAACACACTC AAAAAATAAA AAGACATTTT
8601 CTTTAGTCCA TGTCTGATCC AACAAGAAAG AGGAGGAACC AAGTCAAGAA
8651 TGAGTGAAGA AGCTGGGCGC AGTAACTCAC ACCTGTAATC TCAGCACTTT
8701 GGGAGGCCAA AGTGAGAGGA TCACTTAAGG CCAGAAGTTT GAGACCAGCT
8751 TGGGCAACAT AGCGAGACCT GCATGTCTAC AAAAAAAAAA AAAAAATTAA
8801 AAATTAGCCA GGCATGGTGA AATCACTGAA CACATAAAGG CTGGGCATGG

FIGURE 3C

8851 TTGCTCACAC TTATAATCGA AACACTTTGG GAGGCTGAGA TGGGAGGATC
8901 ACTTGAGGCC AGGAGTTCGA AACCAGCCTG GGAAACATTG TAGTCACAGC
8951 TACTTGGGAG GCTGAGGCAG AAGGATCTCT TGAGCCCAGG AAGTGGCTAC
9001 AGTGAGCTAT AATTGCACGA CTGCACTCTA GGCTGGGCAA TGGAGCAAAA
9051 CCCTGTCTCA AAAAAATGGG GCAGGGCTGA TAAAGATTAG ATTACTGTGT
9101 GACTTTGAGC AGCTGCTTTC TCTCTAGGCT TTGGGGGTCT GTTTGAACAA
9151 TGAGGGAGTT GGATACCTTG GAGCTTTCTA AGATTTCTGT GGCGCCTTTA
9201 TTGACACCTT GAGAAGTAGC ATGCAGTGTT TCTACTTTTG GGCAATTGGT
9251 CACTTCTTTT TTTTTGAGAC AGTCTCACTC TGTCGCCCAG TCTGGGGTGC
9301 AGTGGTGTGA TACCAGCTCA CTGCAACCTC CACCCACAAG GTTCAAGCAA
9351 TTCTTGCACC TCAGCCCCCT GAGTAGCTGG GACTACAGGT GACCACATGT
9401 GGCTAATTTT TGTATTTTTA GTAAAGACAG GGTTTCACCA TGTTGGCCAG
9451 GCTCGTTTCA AACTCCTGGG CTCAAGTGAT CCTCCCTTCT CGGCCTCCCA
9501 AAGTGCCGGG ATTACAGGTG TGAGCCACCG TGCCCGGCCC AAGTGCTAGC
9551 TTTCTCTCTC TCTTTTTTTT TTTTTCGAGA CGGAGTCTCG CTCTGTCGCC
9601 CAGGCTGGAG TGCAGTGGTG TGGTCTCGGC TCACTGCAAG CCCCGCCTCC
9651 TGGGTTCACG CCATTCTCCT GCCTCAGCCT CCCGAGTAGC TGGGACTACA
9701 GGCACCTGCC ACCATGCCCG GCTAATTTTT TTTTTATATT TAGTAGAGAC
9751 AGGGTTTCAC CATATTAGGC AGGATGGTCT CGATCTCCTG ACCTCGTGAT
9801 CCGCCCGTCT CGGCCTCCCA AAGTGCTGCG ATTACAGGCA TGAGCCACCA
9851 CGCCCGGCCC TACCAAGTGC TAGCTTTCAT TTGACGCAGT GAATGTTTCT
9901 TGTACACCTG GCAGGTGCCT GGCACTGCAT AGGCACTGTT GAGATGTGAA
9951 GGTGGCCCTG GGGACAGAAA ATTATACTGG GCTTGACTGT GTGTCTCCAT
10001 CCCTTGACAT CAGCCAAGCC AGCAGCTGCT TTACATACAT GATGAGCAGA
10051 CAGCTGCTTG AAAGAGATGA GGAAACTCCC AGACCAACGG CTCTTACCAG
10101 AGGGCCAAGG GAGGTCCCCA CAGAGTCAGA GGCTGCAGCT GGTCCCTGAA
10151 ATCCAGGCAG AATTTTAGAA ATGAAGACAG TCAGCTGGGT GCAGCGGCTC
10201 ATGCCTGTTA TCTCAGCCAC TTCGGAGGGC TGAGGTGAGA GGATTGCTTG
10251 AGCCCAGGAG GTGGAGGCTG CAGCAAGCTA TGATGACACC ATGCATTCCA
10301 GCTTGGGCGA CAGAGCGAGA CCCTATCTCT AAAATAAAAA TGAAGAAGAC
10351 AGTTAATGAC GTCTCCTCCC TGTCTGCCTC ACTGGGTAAG CATTCGCCCA
10401 GCCAACATCT GGAACATCCC AGTTCTGCAA AGAGCCACAC CCTTCCCAGA
10451 AAGAGCCCAA CTTGCCAAAG ATTTACTTAT TTGTTTTAAA CTGGTTTTAG
10501 TTGACCGCTT TTCATTTTGT GTATAGCAGC GTTTTAAGGA AGGTCTAATT
10551 TATCCAGGCC ACCTGCTGCT TTAGCAAACC AAGGGAGAGG ATGTGAGATT
10601 CTAAGGAATT TACATATGTA TGTCATATAT ATATATATAT ATATAGACAC
10651 ACAATTTTTT TTTGAGACAG GGTCTTGCTC TGTCATACAG GCTGGAGTGC
10701 AGTGGCACAA TCATAGCTCA CTATAGCCTC AGATGCCTGT GCTCAAGCAA
10751 TCCACTCACC TCGGCCTCCT GAGTAGTGAG ACTACAGGCA CACACCACCA
10801 CACCCAGCTA ATTTTTTAAT TTTTTGTAGA GACTGAGTCT TGCTGTGTCG
10851 CCCAGGCTAG TCTTGAACTC CTGGGCTCAA GCAATCCTCC CACATTGGCT
10901 TCCCAAAGTG CTAGGATTAC AAGCGTGAGC CACTATGCCT GGCTTATTTT
10951 TAAGGTTATA TGCATGCAAA GCCTGTATCA ATGAAAATAT TTTCTTTGGT
11001 TTTTTTCAAC TTTTCATCTT CGCATTTTGC AGATTTATAG AAAATTTGCT
11051 AAAATAATAA GTCCATTGAA TACATACACA CCCTTCACCA AGGTTCACCA
11101 ATTCGTAACT GCCATATTTG GGAGTTATAT GTGTGTCTCT CTATATATAC
11151 ATATATGGAT ACAGATACAT ATACATGTTT AGTGACTTGT TTATATTTGT
11201 ACATACATGT ACATGTTGTT ATTTATTGAT CGTTTGGGAG TAAGTTGCAG
11251 GGATCATTGA CTCCCCCACA ATTATGCTAG ATATTCTCAA AAGAAGGACC
11301 TTCTCTTTTT TTTTTTTTTT TTTTTTTTGG AGACAGGGTA TCACTGTCAT
11351 TGAGGCTGGA GTGCAGTGAT GCGATCACAG CTCACTGCAG CCTCAACCTC
11401 CCAGGCTCAA GTGATCCTCC CACCTCTGCC TCCCAAGTAG CTGGGACTAC
11451 AGGCACGGGC CACCACGCCT GGCTAGGCAT TCTGTTATGT AATTATCAAT
11501 TGTATCTTAT AGTTCAGTGA TCACATTTTG GAAATGTAAC ATTGATACCA
11551 TTATCTAATA CACAGACCAT ATTCAAATTT TGCCTATTGT CTCTATACTG
11601 AACTACTGAG CTGTCCTTTA TAGCAATCTC CCCCTCATCC ACAGTCCAGT
11651 CCATGATCAA CATTGCATTT AATCGTCATG TGTCATCAGT ATCTTTTTTT
11701 TTTTTTTTTT TGAGACGGAA TTTTGCTCTT GTTGCCCAGG TTGGAGCGCA
11751 ATGGCGCAAT CTTGGCTTAT TGCAACCTCC GCCTTTGGGC TTAAGTGATT

FIGURE 3D

```
11801 CTCCTGCCTC AGCCTCCTAA GTAGCTGAGA TTACAGGCGT GCACCATTAT
11851 GCATGCCTAA TTTTTGTATT TTTATTAGAG ACGGGGTTTT ACCATGTTGC
11901 CCTGGCTGGT CTTGAACTCC TGACCTCAAA TGATCCACCC ACCTCAGCCT
11951 CCCAAAATGC TGGGTTTACA GGCATGAGCC ACTGCGTCTG GCCATTTCCT
12001 CAGCCTTTCA TTGCCCTTCA TGATCTTGAC ATTTTTGAAG TGTACAGGCC
12051 AGTCATTAAA GTAAAATGTT TTTCCTTTTT TTTTTTTTTT TTTTTAAAAA
12101 GAGACAGGGT CTCACTGTGT TGCCCAGGCT GGTCTCAGAC TCCTAGGCTC
12151 AAGTGATCCT CCCGCCTCAG CTTCCCAAAG TGCTGGGATT ACAGGCGTGA
12201 GCCATCGTAC CTGCCCTCGC ATTTGGGTTT GACTGATGTT TCCTCTTAGG
12251 GAGACAGGCT CTGCAGGTTT GGCCTGATAC TGCATAAGTG ATCCTCTGTC
12301 CTTCCGAGTG GATCTTGCCA GGAGACATAT GATGTCAGTG TGCCCTTTGC
12351 TGAGGATGTT CACTTTGATT ACTTGTTTTT TCTGTACTGT AAGGATTTTT
12401 TTCCCTTTGT CATCAATAAA CCATTTGTGA GATTTGAGTC TGTAAATATC
12451 CTGTTCCCAA AAACCCTTCC CCAAATGATT TGAGCATCTA TTGATGATTC
12501 TTGCCTGTAG CGATTATTAC TAGGGTGGCT ACCAAATGCT GAATTTCTAA
12551 CTCTGTTCTT CCTTCTGCAT TTGTTACTGT AAGGAAGAGC TTCTCCCCCA
12601 TACGAGAATA GTCTTTTTGT TTGCTTGGTT GTTTTTTTGA GATAGGGTCT
12651 CACTCTGTTG CCCAGGCTGG AGTGCAGTGA CATGATCATA GCTCACTGCA
12701 GCCTCGACCT CATGGGCTCA AGCGATCCTC CTGCCTCAGC CTCTCGAGTA
12751 GCTGGGACTA CAGGCAGCAC CACCATGCCT GGCTAATTTT TTATTTTTTG
12801 TAATGGTGAG GTCTCACTAT TTTGCTCAGG CTGGTCTCGA ACTCCTGACC
12851 TCAAGTGATC TTCCCACCTC AGCCTCCCAA ATAGCTGGGA TTACAGGAGT
12901 GTGCCACCAT GCTCAGCTAA TTTTCTGTAA AAAATGTCAT AGAGATGGGG
12951 TCTTGCTATG CTGCCCAGGC TGGTCTCAAA CCCCTAGTCT CAAGCAATCC
13001 TCCCACCTTG GCCTCCCAAA GTGCTGGGAT TCCAGGCATG AGCCACCACA
13051 CCTGGCCCTG TTTTTCTTAA AGTTCTCAGT CTCCTCTCTG CCTTACCCCC
13101 ATCCCCTTTT CCATCTCCAG GACCTAGGGC AGAGACAAAG TGAGCATTCC
13151 CTAAAAAGCT TTTATGAGGC AAAATGAAAA CCAGCTCACG CCTATAATCC
13201 CAGCACTTTG GGAGGCCAAG GTGGGTGGAT TACCTGAGGT CAGGAGTTCA
13251 AGACCAGCCT GACCAACATA GAGAAACCCC ATCTGTACTA AAAATACAAA
13301 ATTAGCCAGG CATGGTGGCA CATGCCTGTA ATCCCAGCTA CTCAGGAGCC
13351 TGAGGCAAGA GAATCACTTG AACCTGGGAG GCGGAAGTTG CAATGAGCCG
13401 AGATCACTCC ATTGCACTCC AGCCTGGGCA ACAAGAGCAA AACTCTGTCT
13451 CAAAAAAAAA AAAGAAAAGA AAAGAAAACC AGGTCCCTAA CACCGAAGAG
13501 TTAAAAGAAA TAAGTAAATT TGGCAAATTG GTCTTTTTGT GAGTTAGCTT
13551 ATAGGCAACT GATCGAGGGT CTCTTTCCCG TCTTCACCCT GCAATTGTGG
13601 CTCAGGGCAA GCTGCCAGCT CCCTCCTGCC AATGCAGGAG CAATAGAGCT
13651 TGGCCTCCTC TTGCAGGGCG AGTTTGGGAG TCAGATATGA AGCCACTAAT
13701 CCGGGACCTT TTTGGGACCC AAGGCACTCA TCTGCCCCAA GCATACCAGG
13751 CAGGCCAGGT GCAATGACTC ATGTCTGTAA TCCTAGCACT TTGTTTTTGC
13801 GACGGAGTCT CGCTCTGTCC ACCCAGGCTG GAGTGCAGTG GCAGAATCTT
13851 GACTCACTGC AACCTCCACC TCCCAGGTTC AAGCAATTCC TGCCTCAGCC
13901 TCCCAAGTAG CTAGGACTAC AGGCGCCCAC TGCCACGCTC GGCTAATTTT
13951 TGTATTTTCA GTAGAGACGG CGTTTCACCA TGTTGGCCAG GCTGGTCTCA
14001 AACTCCTGAC TTCAAGTAAT CCATCCACCT TGGCCTCCCC AACTGTTGGG
14051 ATTACAGGTG TGAGCCACTG CGCCCGGCCA GTCCTAGCCC TTTGGGAGGC
14101 TAAGGCGGGC GGATTGCATG AGCTCAGGAG TTCGAGACCA GCCTGGGAAA
14151 TGTGGTGTAA CCCCGTCTCT ACTAAAAATA CAAAAAAAAT TAGCTGGGTG
14201 TGGTGGTGTG CACCTGTAAT CCCAGCTACT CAGGAGGCTG AGGTACGAGA
14251 ATCGCTTGAA CTCAGGAGGC AGAGGCTGCA GTGAGCTGAG ATTGTGCCAT
14301 TGCACTCCAG CCTGGGTAAC AGAGTGAGAT TCTGTCTCCA AAAAAAAAAA
14351 AAAAAAAAAT TCGAGACCAA ACATACCTGG GATTTGGAAG GATAGATCTG
14401 TTCCCCCAGG GTGGAGACAA TGGTCCATTG AATGGGAACA GCTGAGCATC
14451 TTGTGTGGGT GGCCAGTGCC TACAAGCGTG CCACCTTTCT CCAGCTCACA
14501 CCTGTGGCAG ACATCAGTAA TTGATTACAG AATTCCTCCC CTGAAACCAG
14551 AACTCGGTGT TCTGGCCATC TGCTACTTCC CAGTCACACG AAGTAGAATC
14601 CTCCACCTGC TCACCCTGGA TCTGGTGCCC TTCGCCTTGG TTTCCTGTTG
14651 GGGCTCTGAG GGACAGGTGG GCACTGGCCT GACCCCTGCC TTACCCACAG
14701 AGTGGATCCG GGCTGCATGA GCCCAGATGT GAAGAATTCC ATCCACGTCG
```

FIGURE 3E

```
14751 GAGACCGGAT CTTGGAAATC AATGGCACGC CCATCCGAAA TGTGCCCCTG
14801 GACGAGGTAC GGTCCTGAGT CTGTGGGGCA GGACGGGAGG TAGTGCCTTC
14851 ATGCCTAGCC CCCTCCCCAC TCCACCCCCA TTCACATGCC TGCTGTCCCC
14901 AGATTGACCT GCTGATTCAG GAAACCAGCC GCCTGCTCCA GCTGACCCTC
14951 GAGCATGACC CTCACGATAC ACTGGGCCAC GGGCTGGGGC CTGAGACCAG
15001 CCCCCTGAGC TCTCCGGCTT ATACTCCCAG CGGGGAGGCG GGCAGCTCTG
15051 CCCGGCAGAA ACCTGTCTTG TAAGTCAGCC TGCTCCTCGG TTCAGCTGGG
15101 TGCTTTCACT CCTGCTGGGG CTCAGGGGCT GTGGGACCTA GGTCGGGGAG
15151 CCAGCCCTGC ACAAATGCAG CCCAGGCTTG AGCCAGGGAG GTGGAGGCTG
15201 CAGTAAGCTG TCATCACACC ACTGCTCTCC AGCTTGGGTG ACAAAACAAG
15251 ACCCACTCTC AAAAAAAAAG AGGAAACACA CATTTTTTAA AAAGCCGGGG
15301 ACGGGGCCAG GCGTGGTGGC TCATGCCTGT AATCCCAGCA CTTTGGGAGG
15351 CCGAGGCAGG TGGATCACCT GAGGTCAGGA GTTCAAGACC AGCCTGGCCA
15401 ACATGGGAAA CCTCATCTTT ACTGAAAATA CAAAAATTAG CCGGGCTTGG
15451 TGGCAGGTGC CTGTAGTCCC AGCTACTCAG GAGGCTGAGG CAGATGAATC
15501 ACTTGAACCC AGGAGATGGA GGTTGCAGTG AGCCAAGGTC ACGCCACTAT
15551 ACTCCAGCCT GGGCAACAGT GTGAGACTCT GTCTCAAAAA AAAAGAGGAT
15601 GACAGAGCAG GATCTGAGGG GTTGAGGGGA GCTGGGGGCT GCCACTAGAG
15651 CCAGGATAGG CCGAGACACT GGGATGGGCA GCCTTTGGAC TGTCCCAGGC
15701 GGGCCCTCCC AAAGCAGGGG GTGATTGCAT AGACTGGCAT GGACAGGGGC
15751 ATGCAGGCAG GAGGAGGAAG GGGCAGGGCC TTGGCCGGGT GCTACCTGTC
15801 CCCCGGTGGC ACTTGGCACC ATGTGTGCCC CCCAGGAGGA GCTGCAGCAT
15851 CGACAGGTCT CCGGGCGCTG GCTCACTGGG CTCCCCGGCC TCCCAGCGCA
15901 AGGACCTGGG TCGCTCTGAG TCCCTCCGCG TAGTCTGCCG GCCACACCGC
15951 ATCTTCCGGC CGTCGGACCT CATCCACGGG GAGGTGCTGG GCAAGGGCTG
16001 CTTCGGCCAG GCTATCAAGG TACAGAGCAT GCCAGGGTCT CAGGGGACAG
16051 TCTGGGTGGG ACCCCTCCAT CCTCCTTCCT TCCCAGTCTA TGGAAACACA
16101 GTGGAAGGGG TATCTGGCTT CCAGACTCCC TGGCCAGTGC CCTCTCCTCC
16151 CTTGGCCTCC TGGAGCTAAT TAGGAACAGG GGACCTCCTA CAGGTAGACT
16201 GAGACCTTAT GTGCGGGAGG TCATTGAAAG GTGGCTCCTA GCCAGGCACA
16251 GTAGTTTATC CCTGTAATCC CAGCACCATG AGAGGCTAAG GCTGTAGGAT
16301 CGCTTGAGCC CAGGAATTCA AGACCAGCCT TGACATCATC TCTACAAAAA
16351 ATTTAAAAAT TAATTGGGTA TAGTGGTGCA TGCCTGTGGT CCCAGCTACT
16401 TGGGAGGCTT AGGCAGGAGG ATTGTGAGCC AGGAGTTCAA GGCTGCAGTG
16451 AGCTATGATC ATGCCACAGC ACTCCAGCCT GGGCAATAGA GCAAGACCCC
16501 ATCTCAAAAA AAAAAAAAAA AAGACAAGGG ATTAATACAT CCCATCCACT
16551 TGGGTATTTG GGAACATCCC ATGCACAGCC TAGAGTATGA AGCCATCTGC
16601 ACATCTCCCT GGCAGTCCTG GGGTGGAGAT GGGGCTTCCT AGAAGGCGGG
16651 CTTACAGCAG AGCTTCTGTC TTCACACCTC TGTGTCCCAC ACGCAGGTGA
16701 CACACCGTGA GACAGGTGAG GTGATGGTGA TGAAGGAGCT GATCCGGTTC
16751 GACGAGGAGA CCCAGAGGAC GTTCCTCAAG GAGGTCAGTG AGCGGAATGC
16801 CCTCTTCCCT CCAGAGGGAC TTCCAGGTGC TCACCCCTGC CCCATCAACA
16851 CAGGTCGGAA AAGGGCTCTG GGAACCATTG AAAGAAGAGC GAGCAGGCCA
16901 GGCATAGTGG CTCACGCCTG TAATCCCAAC ACTTTGGGAG GTTAAGGAGA
16951 GAGGATACTT TGAGACCAAC CTGGGCAACA TAGCAAGACC CCGTCTCTAC
17001 AAAAAAATTT TAAATTAACC GAGCTTGGCA ATGTGCACCT GTCATCCCAG
17051 CTACTCGGGG GGCTGAGGTG GGAGGCTCGC TTGAGCCCAG GAGTTGGAGG
17101 CTGCAATGAG CCATGATCGC ACCACTGCAC TCCAGCCTGG GGAACAAGGC
17151 AAGACCCTGT GTCCAAAAAA AATAAAAGTA ACTGCATTGG TCGGGCATAG
17201 TGGCTCACGC CTGTAATCCC AGCACTTTGG GAGGCTGAGC CGGGCGGATC
17251 ACCTGAGGTC AGGAGTTCGA GACTACCCTG GCCAACATGG CAAAACCCCG
17301 TCTCTACTAA AAATACAAAA ATTAGCCCAG CATGATGGTG GTGAGTGCCT
17351 GTCATCCAGG CTACTCAGGA GGCTGAGGCA GGAGAATTTC TTGAACTCAG
17401 GAGGCGGAGG TTGCAGTGAG CCAAGATCGT GCCGCTGCCC TCCAGCCTGG
17451 GCGACAGAGT GAGACTCCTT CTCAAAAAAA AAAAAAAGAA AAGAAAAAAG
17501 AAAGTAACTG CAGGCAGGGG ACTGGGAAAA AGAGCATCGC TGGGGGTGGG
17551 GGCAGCTCAA GCAGAGGGCA CAGGACGCCA GAGGGTGTGG CAGAGGCAGG
17601 AGAGGGGAGC TGGGGGTTCC GTATCTTTGA GACCGCCTAC AGCCCCTGGT
17651 GGGATGGAAA AGGGAGAAGC AGACCCAAGC ACAGCTGGGA CCACACAGAG
```

FIGURE 3F

17701 CCCGGGCCCA GCCTGTTTGT GCCCCGCCAG GTGAAGGTCA TGCGATGCCT
17751 GGAACACCCC AACGTGCTCA AGTTCATCGG GGTGCTCTAC AAGGACAAGA
17801 GGCTCAACTT CATCACTGAG TACATCAAGG GCGGCACGCT CCGGGGCATC
17851 ATCAAGAGCA TGGTGAGTCC TGGGCAGAGC CAGCCACCCC CGCTGTGCGG
17901 CCCCGGGCAA AGCAGCTCCC TCTGTGAGCC TCAGTCTCAT CTCTTCAATG
17951 GGGGGAAGCC ACAGGGGTCT CAAAGGCCCT CTGAACCCTG ATTCCTAATC
18001 AAAAAGGGGA GCGACTGACT CCATCTAAAG CTAGGAAAGG CCAGGTACAA
18051 TGGTGCACAC CTGTTATTCT GGCACTTTGG GAGCCCAAGG CAAGAGGATC
18101 ACTCGAGGCC AGGAATTCAA GGCTGCAGTG AGCTGTGATC TCACCACTGC
18151 ACTCCAGCCT GGACCACACA GCAAGACCCT ATCTCAAAAA CTAAAATAAA
18201 ATTCAGAGCT TTCCTTAAGG ATTTGAATAA AATTACAAAT CCATCTTTAG
18251 AAATAAAGTG CTCAGGCCAG GTGCAGTGGC TCATGCCTAT AATCTCAGCA
18301 CTTTCAGAGG CTGAGGCCAG CAGATCACCT GAGGTCAGGA GTCCAAGACC
18351 AGCCTGGCCA ACATGGTGAA ACCCCGTCTC TACTAAAAAT ACAAAAATTA
18401 GCTGGGCCTG GTGGCAGGCA CCTGTAATCC CAGCACTTTG GGAGACTGAG
18451 GTTGGCAGAT CACCTGAGGT CAGGAGTTCG AGACCATCCT GGTAACCCGT
18501 CTCTACTAAA AATACAAAAA ATTAGCCGGG CAAGGTGGCA GGTGCCTGTA
18551 GTCCCAGCTA CTCGGGAGAC TGAAGCAGGA GAATGGCGTT GAACCCAGGG
18601 GGCAGAGCCT GCAGTGAGCC AAGATCGCAC CACTGCGCTC TAGCCTGGGT
18651 GACAGCGAGA TTCCGTCTCA AAAAAAAAGC ACTTGGAGGA AGCCTCACAG
18701 AGTCCTGTGC TGGACCACAC CCTGGGGATC CAGTCCTGGC CTCCAGCCCC
18751 ATTTCTGTAC CACCCTGAGA CCATGGGATC TTCCTCAGGT TGGATTACCT
18801 TGTATCCAAG GTGTGGACCC TATGGGCTCC TGCTAGGTGT AACTTGACAC
18851 AACGGGTTCC GTTGTCAGGT GCAATTTAGA AACTCTGGGC TAGGCCAAGC
18901 GCAGTGGCTC ACACCTGAAT TCCCAAACTT TGGAAGGCCG AGGCAGGAGG
18951 GTCACTAGAG GTCAGGAGGT CAAGACCAGC TTGGACAACA TAATGAGATC
19001 CCAATCCCAT CTCTACAAAA AAAATTAAAA AATTAGCCAA ATGTGGTGAC
19051 ACATGCCTGT GGTTCCAGCT CCACAGGAGG CTGAGGCAGA AGGATCACTT
19101 GAGCACAGGA GGTCGAGGCT GCACTCCAGC CTGGGTGATA GAGTGAGACC
19151 CTGTCTCAAT AAAAAATAAA GATCTCCAAG GGGATGAGGT TTGAGAATGA
19201 GGCGTCTCCC CCAAATGATT TGAGCCCAAA GCCCCGTTCT CCTGGCATGG
19251 CTCAGTGCTG CCACTGCGCA GGTGACCTTG CTGGGCCCTT CTACCTCTTA
19301 CCTGTCTGTG AAAGTAGGTT CTAATTTTTT AAAAACCTAG AAAGATGAGT
19351 TTTTTGTTTT TGTTTTTGTT TTTCCCGAGA TGGAGTTTTG CTCTTACTGT
19401 CCAGCCTGAA GTGCAATGGC GTGATCTCGG CTCACTGCAA CCTCCACCTC
19451 CCAGGTTCAA TCGATTCTGC CTCAGCCTCC CGAGTAGCTG GGATTACAGG
19501 AGCCCACCAC CACACCCGGC TAATTTTTGC GTTTTTAGTA GAGACAGGGT
19551 TTCACCATGT TGGTCAGGCT GGTCTCAAAC TCCTGACCTC GTGATCCAAC
19601 CACTCTGACC TCCCAAAGTG TTGGGATTAC AGGCGTGAGC CACCACACCT
19651 GACAGAAAGA TGAGATTTTA TAGAAAATAA ATATAGCTTG TTTTCTCAGA
19701 GGAGGCAGAT TGGGAGCTAT AGAGGAATAT CCCTGCTTAG AGTTTGAAAT
19751 CAGTTCTGTT AGGAAATAAT GTTTGTAGGG GCCGGGTGCG GTGGCTCACG
19801 CCTGTAATGC CAGCACTTTG GGAGGCTGAG GCAGGTGGAT CACTTGAGGT
19851 TAGGAGTTTG AGAACAGCCT GGCCAACATG GTGAAACCCT GTCTCTACTA
19901 AAACTACAAA AATTAGCTGG GTTTGGTGGT GGACACCTGT AATCCCAGCT
19951 ACTTGGGAGG CTGAGGCGAG AGAATTGCTT GAGGCCGGGT GCAGTGGCTC
20001 ATGCCTGTAA TCCCAACACT GGGAGGCCAA GGTGGGCAGA TCACCTGAGG
20051 TAAGGAGTTC AAGACCAGCC TGACCAACAT GGTGAAACCC CGTCTCTACT
20101 AAAAATACAA AAAATTAGCT GGGTGTGGTG GCGCATGCCC ATAGTCCCAG
20151 CTACTCAGGA GGCTGAGACA CAAGAATCAC TTGAGCCCCG GAGGCGAAGG
20201 TTGTAGGGAG CTGAGATGGT ACCACTGCAC TCCACCCTGG GTGACAGAGT
20251 GAGACTCCAT CTAAAGAAAA AAAAAAAAGG AAATAATGTC TGTGAGCTGT
20301 GTTGACTCAT ACTCCTTAGA AGCAGACAGT TGTGGGTGCC CGAAGAAATC
20351 GGGGTGTTGG GGAGCCCAGG GACCCTCTAG GACGCTTGCC TCTTCCTGCC
20401 TCTGTCTCAT GCAACCATCC CTGCCATCGG GGCCCCCACC GGCCCCACCC
20451 TGGCCATTCT TTCTCCATCC CAGGACAGCC AGTACCCATG GAGCCAGAGA
20501 GTGAGCTTTG CCAAGGACAT CGCATCAGGG ATGGTGAGTG AGCCGGGTGC
20551 TCTAGCTCCA TTCATAATCC CACCAGGAAT TTGCAAACAG AACCCACAAA
20601 GAAGCTTTGA AAGAGGGCAG AGGGGGTCGA TGGGAGAGTG GGAAGAATCG

FIGURE 3G

20651 TCCCGACTGG CCTGATTGGG GTGGGAGCAG AGGGAGTTCC TGGGGAGCCA
20701 GGATGGGCTG GGGTCCCTCT GCACAGCTGC CCCCTGACTC CCGTGTCCCC
20751 GTCCCTAGGC CTACCTCCAC TCCATGAACA TCATCCACCG AGACCTCAAC
20801 TCCCACAACT GCCTGGTCCG CGAGGTGAGT ACCAGGGCCC CACGTGGCTG
20851 GGTGTCAGGA GACAGCAGGA GCCCATCCAA CCCCAGCCTC AGGGCCTTCC
20901 CAGAACTGGA GGCCCCTCCA TGTTGCCTCC ATGACTTCAA TTTGAGGTGG
20951 GGGTGGGGGG CAGCAGCCCG TGGGGAAGAG CGCAGGGTCA GGAGGCAGAC
21001 AGACCTGGGT TTGAGTCCTG TCTCTGCCAC TGACTCATGG TGGACCATCA
21051 GAGTCCCAGG CTGGTAGGAG GGTCTCATAA ATCAATGAAG GAGAAAGTGA
21101 CATGTAAGCT ACAAAGGACC AGGACCGTGG TCTTCATAGA GCACAGCCCA
21151 TGGCAGAGTG GCCATGGGCT ACACCAGACA GCACCAGCAT CTGGGGGCCA
21201 CAGAGTGGGG GCATAGGCGT ATGGGCTGGA GTGGTCAGGG CAGGCTTCCT
21251 GAAAGAGGAG GCTTGGCCAG ACACAGTGGC TCACACCTGT AATCCCAGCA
21301 CTTTGGGAGG CCGAGGCAGG CGGATCACGA GGTCAGGAGA TCGAGACCGT
21351 CCTGGCTAAC ATGGGCACTG TGGCTCACAC CTACAATCCC AACACTTTGG
21401 GAGGCCGAGG TGGGTGGATC ACTTGAAGCC AGGAGTTCAA GACCAGCCTG
21451 GCCAACATGG CTAACACGGT GAAACCCCAT CTCTACTAAA AATATAAAAA
21501 ATTAGCCGGG CGTGGTGGCA GGTGCCTGTA GTCCCAACTA CTTGGGAGGC
21551 TGAAGCAGGA GAATGGTGTG AACCCGGGAG GCGGAACTTG CAGTGAGCCA
21601 AGATCGCGCC ACCGCACTCC AGCCTGGGTG ACAGAGCGAG ACTCCATCTC
21651 AAAAAAAAAA AGAGGAGGCT TTAGGTGGAT ATTTAAGCAG GGGACGGGCA
21701 GGCAAAGAGC CCAGTGTCTA AGGATTGTCA AGGGAGGAGA GCCCGGTTCT
21751 CCACCAAAAG CACAGGAGCG AGTAACCATG CCCATCTGGA GAGGTGGTGT
21801 ATTCGTGTCC TGGGGCTGCC ATCATGAAGT ACTGTGAACC AGATGGCTCA
21851 AAACAACAGA AATGTGCTGG GCACAGTGGC TCACACCTAA AATCCCAGCA
21901 ATTTGGGAGG CCAAGGCAGG TGGATTGCTT GAGCTCAGGA GTTTGAGACC
21951 AGCCTGGGCA ACATTACGAA AGCCCATCTC TGCCAAAAAT ACAAAACGGA
22001 ATAGCCAGCC GTGGTGGCAT AAGCCTATGG TCCCAACTAC CTGGGAGGCT
22051 GAGGTGGGAG GATCACTTGA GCCTGGGAGG TAGAGGTTGC AGTGAGCCAA
22101 GATTGTGCTA CTCTACTCCA GCCTGGGAGA CAGAGCCAGA CCCTGTCTCA
22151 AAAAAACAAA ACAAAACAAG GCCAGGCACT GTGGCTCACG CCTGTAATCC
22201 CAGCACTTTG GGAGGCCGAA GTGGGTGGAT CACTTGAAGC CAGGAGTTCA
22251 AGACCAGCCT GGCCAACATG GCAAAACCCT GTTTCTACTA AAAATTCAAA
22301 AATTAGCAGG CATGGTGGCG CATGCCTGTA ATCCCAGCTA CTCGGGAGGC
22351 TGAGGCAGGA GAATTGCTTG AACCCAGGAG GCAGAGGTTG TAGTGAGCTG
22401 AGATTATGCC ACTGCACTCC AGCCTGGGTG ATAGAGTCAG ACACCGTCTC
22451 AAAAAAAAAA AAGCATCACA TGGCAAGAGG GGCTGACAAG AGACCCCCAA
22501 ACTGACCATT ATACAGACCC ACTCTTGTGA TAACTAACCT GGTCCCTCAA
22551 TAACCCATTA ATCTGTTAAT TCATACAGAG CCCTCATGAC CCAATCACCT
22601 CTTACAGGCC CTGCCTCTTA ATACCGTTAG AGTCAGGCCA GGCATGGTGA
22651 CATGGGCCTG TAGTCCCAGC TAGTTGGAAG GCTAGGTGGG AGGATCCCTT
22701 GAGTCCAGGA GGTAAATGTT ACAGTGAGCT CTGATTGTGT CACTGCACTC
22751 CAGCCTGGGC AACAGAGCGA GCCCCTGTTT TTAAAACAGC AACAAGCCAG
22801 GCACAGTGGC TCACGCCTGT AATCCCAACA CTTTGGGAGA CTGAGGCAGG
22851 CAGATCACTT GAGGTCAGGA GTTCAAGACC AGCCTCACCA ACACAGTGAG
22901 ACCCCTCTCT ACTAAAAATA CAAAAATTAG CTGGGCGTGG TGGTGGGTGC
22951 CTGTAGTCTC AGCTACTCAT GAGACTGAGG CAGAATTGCT TGAACCCGGG
23001 AGGTGGAGGT TGCTGTGAGC CGAGATCACG TCACTGCACT CCAGCAACAG
23051 AGTGGGACTC CATCTCAAAA AAAATAAAAA ATAACAGAGA TCTGTGTTGG
23101 CTTACACCTG TAATCCCAGC ACTTTGGGAG TCCAAGGTGG GCAGATTGCT
23151 TGAGCCCAGG AGTTTGAGAC CAGCCAGGCA ACATGGCAAA AAAATAAAAA
23201 AATTTGTCTC TACAAAAAAA TTAAAAAATT AGCTGGCATG GTGGTGAGTA
23251 TCTATAGTAC CAGCTACTCA GGAGGTGGAG GTGGGAGGAT CGCTTGAGCC
23301 TGGGAAGTTG AGGCTGCAAT GAGCTGTGTT CGTGCCACTG CACTCCAGCC
23351 TGGGCCACGG GAGGGAGACT CTGCCTCAAA AAAAAAAAAA AAAAATCAAA
23401 CCCGAAAAGC AAAAAACATA GACCTCACCT GCTTATTGGG AATATTCAAG
23451 ATAAAATTAG GCCAGGCACG GTGGCTCACG CCTGTAATCC CAGCACTTTG
23501 GGAGGCCGAC GTGGGCGGAT CACGAGGTCA GGAGATCGAG ACCATCCTGG
23551 CTAACACGGT GAAACCCCGT CTCTACTAAA AATACAAAAA ATTAGCTGGG

FIGURE 3H

23601 CATGGTGGCA GGCGCCTGTA GTCCCAGCTA CTTGGGAGGC TGAGGCAGGA
23651 GAATGGCGTG AACCTGGGAG GCAGAGCTTG CAGTGAGCTG AGATCGTGCC
23701 ACTGCACTTC AACCTGGGCA ATAGAGCAAG ACTCCAACTC AAAAAAAAAA
23751 AAAAAAAGAT AAAATTGGGC CAGGTATGGT GGCTTACTCC TGTAATCCCA
23801 GCACTTTGAA AGGCTGAGGC AGGTGGACCA CTTGAGGCCA GAAGTTGAAG
23851 ACCAGTCTGG GCAACATAGC AAGACCCTAT CTCAATCAGT CAATCAACCT
23901 AAATAAATAG TAAATCTGGT GGCATGCCAA GCACAGGACC TGGGTCTATA
23951 ATCAAAATTC CTGTCTTGAT GGGCACAGTG GCTCACACCT GTAATCCCAG
24001 CACTTTGGTA GGCCACAGTG GGTGGATCAC CTGAGATCAG GAGTTCGAAA
24051 CCTGCCTAGC CAAGTATGGT GAAACCCGTC TTTACTAAAA ATACAAAAAT
24101 TAGCCAGGCA TGGTGGCAGG CGCCTGTAAT CCCAGCTACT CGGGAGGGTG
24151 AGGCAGGAGA ATCGCTTGAA CCTGGGAGGC GGAGGTTGCA GTGAGCCGAG
24201 ATCATGCCAC TGCGCTCCAG CCTGGGTGAC AGAGCAAGAC TCCGTCTGAA
24251 AAAAAAAACA AAAGAATTCC TGTCTTCTCT CCGAAACAAA GCAGCATCAG
24301 TGCCCCCGCA GGTGGGAGGG AGCGCTTGCA GGAGGGAGCA GTGGGTCCGC
24351 CACGACGGTC TGGGGAGCAG GTGGGGAGGG GGCAGAGGGT GCAGCGTGTG
24401 GTGGGAGGGA GGAAGCCACA CTGCTATCTT CAGGTGCTTC CCGCAGCTCC
24451 ATTTGCAAAG AGCGGATGGG TTTGGGGAAG GAAGGGGTCC CCACCCTGTG
24501 CCAATACAGC GTATCAGAGG TATGTTCTCT GGGCTGTCTA CGGGTTGGCT
24551 TGGGGTCCTG GGGAGGGGCA GGCCAAGCGG GCAGTACTAG GATCGGGTCC
24601 CAGCATGACC CGGCTTCACC TTCCCAGAAC AAGAATGTGG TGGTGGCTGA
24651 CTTCGGGCTG GCGCGTCTCA TGGTGGACGA GAAGACTCAG CCTGAGGGCC
24701 TGCGGAGCCT CAAGAAGCCA GACCGCAAGA AGCGCTACAC CGTGGTGGGC
24751 AACCCCTACT GGATGGCACC TGAGATGATC AACGGTGAGT GGTTCAGCCC
24801 TGCCCATCAT GGCCCTCACG GGAAGCCATG GGGGAGCCCA GGAGAGCTGT
24851 AACCTCCCAA GCCCCTGGCC CCTCCCAGCC TCCTTGGCTC TTCAGTTACC
24901 CTGTGGGTCC TGTTGCTCCT ATAACACACT TAGTGGCAGC CAGGCACGGT
24951 GGCTCACGCC TGTAATCCCA GCACTTTGGG AGGCTGAGGT GAGTGGATCA
25001 CCTGAGGTCA GTAGTTGGAG ACCAGCCTAG CCAACATGGT GAAACCCCCA
25051 TTCTTTACTA AAAATACAAA AATTAGCTGG GCATGGTGGC GGGTGCCTGT
25101 AATCCCAGCT ACTAGGGAAG CTGAGGCAGG AGAATCGCTT GAACCTGGGA
25151 GGCAGAGGTT GCAGTGAGCC GAGATCGCGC CATTGCACTC CAGCCTGGGT
25201 GACGAGCGAA ACTCCATCTC AAAAAATAAA TAAATAGAAG ACACTTAGTG
25251 GCTTAAATAA ATGATCATAC AGTTCTGGAG TCTGAAGTCC AGCGTCAGCC
25301 TCACCGGGCT GAAATCAAGG CGCCGGTAGG GTGAGCTCCT TCTGCAGGCT
25351 CCGGGGCACC TGTTTCCTGA CCTTTTCTGG CTCGTGGAGG CTTCCTCATT
25401 CCTCCTGTTG CTGCCCCCTC CTCTGTCTTC AGGGCTGGCT GCAAAGCATC
25451 TTCTCTTCTC TGATCTCTGC ATCCATCCCC GCATCTCTTT CCCTGGCTCT
25501 AACCTTCCTC CTTTTTTTTT TTTTTTTTAA AGAGGGTCTC GCTCTGTTAC
25551 TCAGGCTGGA GTGCAGTGGT GCCACCATAG CTCACTGCAG CCTCAACCTT
25601 CTGGGCTCAA ACTGTCATCC CACCCCAGCC TCCTGAATAG CTGGGACCAC
25651 AGGCATGCAA CACCACACCC AGCTAATTTT TTTATTTTTT ATTTTTTATT
25701 TTTTTTTGAG ACAGAGTCTC GCTGTGTCTC CCAGGCTAGA GTGCAGTGGC
25751 GTGATCTCAG CTCACTGCAA GCTCCGCCTC CTGGGTTCAC GCCATTCTCC
25801 TGCCTCAGCC TCCCGAGTAG CTGGGACTAC AGGCGCCCGC CAACACGCCT
25851 GGCTAATTTT TTGTATTTTT AGTAGAAACG GGGTTTCACC GTGTTAGCCA
25901 AGATGGTGTC GATCTCCTGA CCTCGTGATC CGCCCGTCTC GGCCTCCCAA
25951 AGTGCTGGGA TTACAGGCGT GAGCCACCGC GCCTGGCCAA TTTTTTAAAT
26001 TTTTAATAGA GACGGGGGTA TCACTATGTT GCCCAGGCTG GTCTCAAACT
26051 CCTGGCTTCA GGCGATCCTC CTGCCTTGAC CTTTCAAAGT GCTGGGATTC
26101 CAGGCATGAG CCACCATGGC CCTCCATCCT TCTGATAGGG ACCCTTACGG
26151 TGACATTGGG CCCACCTGGA TAATCCAAAA GCAGCCCTCC ATCTCAAGAC
26201 CCTCAACTTA ATCCCATCTG CAGAGTCCGA TGGAAGGTGG GACGTATACA
26251 AGTCCCAGGG ATCAGGACGC AGTCATCTTT GGGGATCATA GTTCTGCCTC
26301 CCACAGGGTC TGCTTCCCTC AGTCCATTTC TTTGCTGTCA ATGGTCCTAT
26351 ATATGCCCAG ATTATAGGTT ATAAAGTCCT TCTACAAGCA GGTGACACAT
26401 GAACACAGGT TCAGGGCAGG CAGACCCCAG CCATCACCTC ATCATAGTTA
26451 ACCTAGTTAA ATTAGCCTGG CATGTGGCGT GGTGCCTAAT GCCTGTGGTC
26501 CCAGCTACTC AGGAAGCCAA AGCGGGAGAT TTACTTGAGC CAAGGAGATC

FIGURE 3I

26551 AAGGCTGCAG TGAGCTATGA TCATACCACT GCCTTCTAGC CTGGGCAACG
26601 GAGTGAGACC CTGTCTCAAG AAAACAAAAA ATAGGCCAGG CACAGTGGCT
26651 CACACCTGTA ATTCCAGCAC TTTGGGAGGC TGAAGCAGGC GGATTGCTTG
26701 AGGCCAGGAG TTCGAGACCA GCCTGGCCAA CATGGTGAAA CGCTGTCTCT
26751 ACTGAAAATA CAAAAATTAC CCGGGTGTGG TGGCACAGCT ACTAGGGAGG
26801 CTGAGGCAGG AGAATCACTT GAACCCAGGA GCAGAGGTTA CATTGGGCCA
26851 AGATTGCACC ACTGCACTCC AGCCTGGGCA ACAGAGGAAG ACTGTGTCTC
26901 AAAAAGAAAA AAAAAAAAAC CTTCCTGTAA TCCCAGCACT TTGGGAGGCT
26951 GAGGTGGGCG GATCACGAGG TCAAGAGATT GAGACCATCC TGGTCAACAT
27001 GATGAAACCC CATCTCTACT AAAAATACAA AAAAATTAGC TGGGCGTGGT
27051 TGCACGCGTC TGTAGTCCCA GCTACCCGGG AGGCTGGGGC AGGAGAATGA
27101 TGTGAACCCA GGAGGCGGAG CTTGCAGTGA GCCGAGATCG CACCACTGTA
27151 CTCCAGCCTG ACGACAGAGT GGGACTCTGT GTCAAACACA CACACACACA
27201 CACACACACA CACACACACA CACACACACA CACACAGAGT TAACATAGCC
27251 CGCAAAGAAG ACTATAAAAC AGTCTTAGTG GCCGGGCGCA GTGGTTCACG
27301 CTTGTAATCC CAGCACTTTG GGAGGCCGAG GCAGGTGGAT CATGAGGTCA
27351 GGAGTTTGAG ACCAGCCTGG CCAACACAGT GAAACCCCAT CTCTACTAAA
27401 AATACAAAAA TTAGCTGGAC ATGGTTTCGG GCGCCCGTAA TCCCAGCTAC
27451 TCAGGAGGCT GAGGCAGGAG AGTTGCTTGA ACCCAGGAGG CAGAGGCAGG
27501 AGAGTTGCTT GAACCCAGGA GGCAGAGGTT GCAGTGGGCG ACAGAGCAAG
27551 ACTCTGTCTC AAAAAACAAA AAAGTCTTAG TGTTTCCTAT GTTTAGGGAT
27601 TAGTGTGAGG ATTAAAGGTT GTAAACTCAT TTCCACCTAG TTGGCATTCA
27651 GTAAATGAGA ATTGACATTT AGTACTAATT GTTTCGGGTA TTTTGTTTTT
27701 TGTTTTTTGT TTTTTGTTTT TTCTGAGACC GAGTCTTGCT CTGTCATCCA
27751 GGCTAGAATG CATGGTGCGA TCTCGGCTCA CTGCAAGCTC CGCCTCCCGG
27801 GTTCACACCA TTCTCCTGCC TCAGCCTCCC ACGTAGCTGG GACTACAGGC
27851 GCCCGCCACC ACGCCTGGCT AATTTTTTGT ATTTTTAGTA GAGACGGGGT
27901 TTCACCATGA TCTCGATCTC CTGACCTCGT GATCCACCCG CCTCAGCCTC
27951 CCAAAGTGCT GGGATTACAG GTGTGAGCCA CCGTGCCCGG CCAGTTTTTT
28001 GTTTTTGAGA TGGAGTCTTG CATTGTCACC CAGGCTGGAG TACAGTGGCG
28051 TGATCTCGGC TCACTGCAAC CTCCACCTCC TGGGTTCAAG TGATTCTCCT
28101 GCCTCAGTTT CCCTAGTAGC TGGGATTACA GGCACCTGCC ACCATGCCTG
28151 GCTAATTTTT CTATTTTTAG TAGAGATGGG GTTTCACCAT GTTGGCCAGG
28201 CTGATCTTGA ACTCCTGACC TCAGGTGATC CACCCGCCTC GGCCTCCCAA
28251 AGTGCTGGGA TTACAGGTGT GAACCACTGT GCCCGGCCAT GTACCGATTA
28301 TTTTTAACAT CATTAAGTAG CTGGTATCAT TCCCATTTTA CAATAAGGAA
28351 ACTGAGGCTC AGAGAGTCTG TGTCAGTTTC CTGAGGTTGC TGTAATAAAT
28401 TGTTAGAAAC TTGATTATTT AAAACAGCAG AAAATGGTCA GGCACAGTGG
28451 CTCACACCTG TAATCCCAGC ACTTTGGGAG GCCGAGGCGG GCAGATCACT
28501 GGAGGTCAGG AGTTCGAGAC CAGCCTGGCC AACATGGTGA AACACCATCT
28551 CTACTAAAAG TACAAAAATT AGCTGGGCAT GGTGGCAGGC GCCTGTAATC
28601 CCAGCTACTC GGGAAATTGA GGCAGGAGAA TCGCTTGAAC CCAGGAGGCA
28651 GAGGTTGCAG TGAGCCACAA TCGTACCACT GCACTCTTGC CTGGACAACA
28701 AAGCAAGACT CCATCTCAAG ATAAAATAAA CAGCAGAAAT TTATTCCCTC
28751 TTAGTTTTGG AAGCCAGAAG GTTGAAATCC AACAGGGCTG CGCTCCCTCC
28801 AGGGCGATCT AGGGGAGAAT GCATTCCTTG CCTCTTCCAC CTTCTGGTTG
28851 TTTTGCATTC CTGGGCTTGT GGCCGCATCA CTCCAGTCTC CACCCCTGTC
28901 TTCACAGGGC CACCTCCTCC TCTTCTGCTG TGTCTTCTCT GTGTCTCTCT
28951 CAAGAGGGCA TTTGCAGTGG CATTTGGGGC CCACCCAGAT CATCCAGCAT
29001 CATCTCATCT CCAGATCCTT AACTTAATCC CATCTGCAAA AGACCCTTTT
29051 TCTGACCCAG TAACATTCAC AGATTCCAGA GACCTGACAT GGTTCCCTTT
29101 TGGGACCAGC ACAGAGTTCA TGACTTGTGC AAAGTCACGC AGCTGATCGG
29151 TGCCTCGAAC TCCTTGTCCA GGGCTCTGCC CCTTGCTCCT CAGAGCTCCC
29201 AAAGGCTTGC TCAGACCTGG TGGGGTTGGG GGAAAGAGCC TAAGCCTGGG
29251 TTCCCATAGA GGTTGCCGGC ATCTGCCTCC TGGGCCTGGA CCTCCCGGCC
29301 GGGGCATCCT CCCAGCTGGC CTGGTCCCCT GCCTTTTGGC ATCCCTGGCA
29351 CCCCCATGTG TTCATCTGCT GACAGTCGGT CTCTTTATCC AGGCCGCAGC
29401 TATGATGAGA AGGTGGATGT GTTCTCCTTT GGGATCGTCC TGTGCGAGGT
29451 AGGTCCAGGG TTGGGTAGCA GCGGTGTTGA GGCCTGGGCT CCTCCCCACT

FIGURE 3J

29501 CACCCAGGCT GCAGGCTCAG CATCTGCAGG GGCCTCATGC CAGGAAGCCT
29551 GCCCACAGCA AGGCATGGGC TGGCCCCCAT GGGGTACTGC AGTCAGGCTG
29601 CAGCCAGGCC CAGTGCCACC TGCCCTCAAA CCACCTGGAT GGCACCCAGA
29651 TGCCCAGGCT GAGGGCCCCC TGGAGTAACT GCCGGGCCTT GTACTGGACA
29701 GATCATCGGG CGGGTGAACG CAGACCCTGA CTACCTGCCC CGCACCATGG
29751 ACTTTGGCCT CAAGGTGCGA GGATTCCTGG ACCGCTACTG CCCCCCAAAC
29801 TGCCCCCCGA GCTTCTTCCC CATCACCGTG CGCTGTTGCG ATCTGGACCC
29851 CGAGAAGAGG TGAGTGGGGT GGGGCCCTGG CCTGGGAGAC GGTGGGGCCG
29901 ATTCCCGGGA CAGCCAGACC CACCGTTCCC CACCCACCTG TCACCCAGGC
29951 CATCCTTTGT GAAGCTGGAA CACTGGCTGG AGACCCTCCG CATGCACCTG
30001 GCCGGCCACC TGCCACTGGG CCCACAGCTG GAGCAGCTGG ACAGAGGTTT
30051 CTGGGAGACC TACCGGCGCG GCGAGAGCGG ACTGCCTGCC CACCCTGAGG
30101 TCCCCGACTG AGCCAGGGCC ACTCAGCTGC CCCTGTCCCC ACCTCTGGAG
30151 AATCCACCCC CACCAGATTC CTCCGCGGGA GGTGGCCCTC AGCTGGGACA
30201 GTGGGGACCC AGGCTTCTCC TCAGAGCCAG GCCCTGACTT GCCTTCTCCC
30251 ACCCCGTGGA CCGCTTCCCC TGCCTTCTCT CTGCCGTGGC CCAGAGCCGG
30301 CCCAGCTGCA CACACACACC ATGCTCTCGC CCTGCTGTAA CCTCTGTCTT
30351 GGCAGGGCTG TCCCCTCTTG CTTCTCCTTG CATGAGCTGG AGGGCCTGTG
30401 TGAGTTACGC CCCTTTCCAC ACGCCGCTGC CCCAGCAACC CTGTTCACGC
30451 TCCACCTGTC TGGTCCATAG CTCCCTGGAG GCTGGGCCAG GAGGCAGCCT
30501 CCGAACCATG CCCCATATAA CGCTTGGGTG CGTGGGAGGG CGCACATCAG
30551 GGCAGAGGCC AAGTTCCAGG TGTCTGTGTT CCCAGGAACC AAATGGGGAG
30601 TCTGGGGCCC GTTTTCCCCC CAGGGGGTGT CTAGGTAGCA ACAGGTATCG
30651 AGGACTCTCC AAACCCCCAA AGCAGAGAGA GGGCTGATCC CATGGGGCGG
30701 AGGTCCCCAG TGGCTGAGCA AACAGCCCCT TCTCTCGCTT TGGGTCTTTT
30751 TTTTGTTTCT TTCTTAAAGC CACTTTAGTG AGAAGCAGGT ACCAAGCCTC
30801 AGGGTGAAGG GGGTCCCTTG AGGGAGCGTG GAGCTGCGGT GCCCTGGCCG
30851 GCGATGGGGA GGAGCCGGCT CCGGCAGTGA GAGGATAGGC ACAGTGGACC
30901 GGGCAGGTGT CCACCAGCAG CTCAGCCCCT GCAGTCATCT CAGAGCCCCT
30951 TCCCGGGCCT CTCCCCCAAG GCTCCCTGCC CCTCCTCATG CCCCTCTGTC
31001 CTCTGCGTTT TTTCTGTGTA ATCTATTTTT TAAGAAGAGT TTGTATTATT
31051 TTTTCATACG GCTGCAGCAG CAGCTGCCAG GGGCTTGGGA TTTTATTTTT
31101 GTGGCGGGCG GGGGTGGGAG GGCCATTTTG TCACTTTGCC TCAGTTGAGC
31151 ATCTAGGAAG TATTAAAACT GTGAAGCTTT CTCAGTGCAC TTTGAACCTG
31201 GAAAACAATC CCAACAGGCC CGTGGGACCA TGACTTAGGG AGGTGGGACC
31251 CACCCACCCC CATCCAGGAA CCGTGACGTC CAAGGAACCA AACCCAGACG
31301 CAGAACAATA AAATAAATTC CGTACTCCCC ACCCAGGTCC TGCGTGGCGA
31351 TGTGTGTCTG GGGCCCTGGG GAAATAGTCA AGGTAAGAGG AGTTAGTCTT
31401 CCCTGACCAG AAGACAAGGA TGAGTGTGGT GGCTCATGCC TGTGATCCCA
31451 GCACTCTGGG AGGCTGAGAC AGGACGATCC CTTAAGCCCA GGAGTTCAAG
31501 ACCAGTCTGG ACAACATAGT GAGATCCTGT CTCTACAAAA ATTTTTTTTT
31551 AATTAGTTGG GCAGAGGCCA GGTGTGGTGG CTCATGCCTG TAATCCCAGC
31601 ACTTTGGGAG GCAGAGGCGG GTGGATCACC TGAAGTTAGG AGTTCAAGAC
31651 CAGTCTGGCC AACATGGTGA AAACTCGTCT CTACTAAAAA TACAAAAATT
31701 AGCCGGGCGT GGTGGCACAT GCCTGTAGTC CTAGCTACTT GGGAGACTGA
31751 GGCAGGAGAA TCGCTTGAAC CCGAAAGGCA GAGGTTGCAG TGAGCCGAGG
31801 TGGTGCCATT CCACTCCAGC CTGGGAAAGA GCGAGACTTT GTCTCCAAAA
31851 AAAAAAAAAA AAAAAATTGG CAGGCCAGGC ACAGTGGCTC ACACCTGTAA
31901 TCCCAGCCCT CTGGGAGGCC GAGGCAGGAG GATCTCCTGA GGTCAGGAGT
31951 TTGAGAACAG CCTGACTGAC ATAGTGAAAC CCCATCTCTA CTAACAATAC
32001 AAAATTAGCC AGGTGTGATG GCACATGCCT GAAATCCCAG CTACTTGGGG
32051 GGTTGAGGCA GGAGAATTGC TTGAACCCAG GAGGCAGAGG TTGCAGTGAG
32101 CCGAGATTGC ACCATTGCAC CCCAGCCTGG GCAACAAGAG CGAAACTCCA
32151 TCTCAAAAAA AAAAAAAAAA ATTAGTTGGG CATGGTGGCA TGCACCTATA
32201 GTCCCAGCTA CTCAGGAGGC TGAGGTGGGA GGATCCTTTG AGCCCAAGAG
32251 ATCAAGGCTG CAGTGAGCCA TGTTTGCACC ACTGCACTCC AGCCTGGGCA
32301 ACAAAACAAG ACTCTGTCTC AAAAAAAAAA AAAAAAAAAA AAAGGCAGGG
32351 ATGGAGGGGG GAAGAGAACA CAGCCCAGTT TTAGGTGGAG CTGAGGTGGT
32401 GGCCCAGCCA GGACAAGTGA AGAGTCTTCA GAGGCTGGGT TTGGAGGGCC

FIGURE 3K

32451 GTGCATATTC CGGAGGTACT GCTTTCATAC TTAAATGTTT TCTTGTAAAA
32501 CTCACACCTG TAATCCCAGC ACTTTGGGAG GCCAAGGTGG GCGGATCATC
32551 TGAGGTCGGG GGTTCAAGAC CAACCTGACC AACATGGAGA AACCCCGTCT
32601 ACTAAAAATA CAAAAAATTA GCCAGGTGTG GTGACACATG CCTGTAATCC
32651 CAGCTACTCG GGAGGCTGAG GTAGGAGAAT TGCTTGAACC TGGGAGGCGG
32701 AAGTTGTGGT GAGCTGAGAT CGTGCCATTA CACTTCAGCC TGGGCAACAA
32751 GAGCAAAACT CCATCTCAAA CAAAACTAAA CTAAACTAAA CTAAAGGGTT
32801 CTATCGAGAA GATGGGCTGC ACGTGATGGC TCACACCTAG ACTCCCAGCG
32851 CTTCAGGAGG CCGAGGTGGA AGGATCACTT GAGGCCAGGA GTTCAAGATC
32901 TGCCTGGGCA ACATAGCAAG ACCCTGTTTT TACCCAAAAA ATAAAAAAAT
32951 TACCCAGATG CTGTGGTGTG TGCCTGTAGT ACCAGCTACT GAGAGGCTGA
33001 GGCAGGAGGA CCGCTTGAGC CTGGGAGGTC AAGGCTGCAG TGAGCTGTGA
33051 TCGTGCCACT GCACTCCAGC CTGGGTGACA CAGCAAGACC TTGTCTCAAA
33101 AATAAATAAA AC (SEQ ID NO:3)

FEATURES:
<u>Genewise results:</u>
Start: 2068
Exon: 2068-2117
Exon: 5446-5584
Exon: 5904-6013
Exon: 7855-8061
Exon: 14701-14806
Exon: 14903-15069
Exon: 15836-16019
Exon: 16697-16783
Exon: 17731-17862
Exon: 20474-20533
Exon: 20759-20824
Exon: 24628-24784
Exon: 29393-29448
Exon: 29702-29859
Exon: 29949-30108
Stop: 30109

<u>Sim4 results:</u>
Exon: 2068-2117, (Transcript Position: 1-50)
Exon: 5446-5584, (Transcript Position: 51-189)
Exon: 5904-6013, (Transcript Position: 190-299)
Exon: 7855-8061, (Transcript Position: 300-506)
Exon: 14701-14806, (Transcript Position: 507-612)
Exon: 14903-15069, (Transcript Position: 613-779)
Exon: 15836-16019, (Transcript Position: 780-963)
Exon: 16697-16783, (Transcript Position: 964-1050)
Exon: 17731-17862, (Transcript Position: 1051-1182)
Exon: 20474-20533, (Transcript Position: 1183-1242)
Exon: 20759-20824, (Transcript Position: 1243-1308)
Exon: 24628-24784, (Transcript Position: 1309-1465)
Exon: 29393-29448, (Transcript Position: 1466-1521)
Exon: 29702-29859, (Transcript Position: 1522-1679)
Exon: 29949-30111, (Transcript Position: 1680-1842)

CHROMOSOME MAP POSITION:
chromosome 7

FIGURE 3L

ALLELIC VARIANTS (SNPs):

| DNA Position | Major | Minor | Domain |
|---|---|---|---|
| 2822 | - | C | Intron |
| 3820 | G | C | Intron |
| 5385 | G | C | Intron |
| 6666 | T | A | Intron |
| 7498 | G | A | Intron |
| 7539 | G | T | Intron |
| 7557 | A | - | Intron |
| 8781 | - | A | Intron |
| 9303 | G | T | Intron |
| 9860 | A | G C | Intron |
| 11629 | A | G T | Intron |
| 12044 | A | G | Intron |
| 12348 | T | G | Intron |
| 13479 | G | A C | Intron |
| 14360 | G | A T | Intron |
| 14371 | A | G | Intron |
| 14383 | T | G | Intron |
| 17112 | T | C | Intron |
| 18360 | - | A | Intron |
| 18679 | A | G | Intron |
| 18703 | T | C | Intron |
| 24472 | T | C | Intron |
| 24542 | G | A | Intron |
| 24900 | C | T | Intron |
| 31542 | A | T | Intron |
| 32344 | T | A G C | Intron |

Context:

DNA
Position

2822
AGGGGTACCCTGGAGTGGGGCCAGGGCATGGCTCTCCCCCGAGGGAGTTCCTCTCTGGCT
GTCCCCAGGGCAGCTCTGCACAGCCTCAGTACCTGGCGCACCTCCCTTGACATCCTTCTT
AGGGACAGTCAGGCACTCTGTGTGGGGCACTCAAGAGAGCCAGGCCCGTCAGCCTCTAGC
TCCTGCCAGAATGCAGGCCTGAGGGGTGAGGGGCGGGGCAGGGGCAGGGGCAGGGACAGG
AACTCCGGCGTGCTCTCCATCCGCAAAGGTTCACTGAGGCCCCGAGCCCCAGCCACTGAG
[-,C]
CACCAAGTCAGCCTGGGCCAGGCCTGGGTGCCCTGTCTGCAATGGAGGCAGAGACGGGGT
CTCGGGGCAGTTCTGAGGATGCTGGGTGCACAGCGGGGGCCTCGCCGGCAGGAATCACTT
ATGCTCTCTCCTGGGCCAAGCTTTGTGGATGCCCAGCCTGGGGCCGCGGGGAGCTGGCAG
GTCAGTGGCAGACACTGGTGGGCAGACCTAGTGTCTGGTAGAACAGGCATCAAGGAAGTG
GTGACCGGAGGGAAGCCAAGTGCACTCAAACCCTCGGGTGAGTCATCACCGCCGGGTCTT

3820
CCCTGTAGACCACCCCCCTCACCAACTTCCGTCCTCCGCCCCACCCCCCGCGGTGATCCGG
TGAACTGCCGGCCCCCTGCTGTGCACCGAGTGGGGCAGTGACCCTGACGTGGCGTCTCCT
GCCGCCCCTGCCACCGCCACCACCTCCGGTGGCCCAGCCTCCGCATTCCCCACCCCCATG
GAGGAATGCACCAGGCCTCCCTTCCTGGATGCACCCCTCACCCACATGCTTCCAAACCCT
GGCATTTTCTGCTCCCCCTTTACTCCCACCCCTTCCCCTAGGCTCCCAGACAAAGGGGAA
[G,C]
TGGCTGGATCCTCTTAAAGGGACAGTGTCCCACCAGCTTACTGCTGAACTCCCCTCCTCA
ACCCCAGTTCCCTAGTTACAGTTAATTAGCATTAGCAGACAGCCCATGAGTGATACCCAT
GCAGGCCCCAGGCTGTGGAGAGTTTCCTGGGTAGGAAACAGCCCTTAAGGTCCCTCATCT
CATCCAGGTCCCAGTCTTTCCTACCTGCCTCTCTCCTAGATTGTGGCCCTTTGGAGCCTG
GTTCTTCTGTCCCTGTGTGACCGACACATAGCACCCAAACAGTGGCAGAGCGGGACGGAC

FIGURE 3M

5385 GGAGGCCGAGGTGGGCGGATCACGAGGTCAAGAGCTCAAGACCATCCTGGCCAAGATGGT
GAAACCCCATCTCTACTAAAAATACAAAAAATTAGCTGGGCATGGTGGTGTGTGCCTGTA
GTCCCAGCTACTCAGGAGGCTGAGGCAGGAGGATCACTTGAACCTGGAAGGCAGAGGTTG
CAGTGAGCCGAGATCGAGCCACTGCACTGCAGCCTGGCGACAGAGCAAGACTCCGTCTCA
AAAAACAAACAAAAAGAAAACTTGTTCTAATTCTTACAAAGGTGCCTGTAGCCGAGGCAG
[G,C]
GGCCCAGGTGAGGTGGAGGAGGGCGGGAGTGGACGTCTCAGCCCGGCCCCTCTCCTGCAG
GTGTTGTGACTGCAGTGCCTCCCTGTCGCACCAGTACTATGAGAAGGATGGGCAGCTCTT
CTGCAAGAAGGACTACTGGGCCCGCTATGGCGAGTCCTGCCATGGGTGCTCTGAGCAAAT
CACCAAGGGACTGGTTATGGTGAGCGCCCCCTGCCTTGCACACTCACCTGGGGTGGGGGT
ATCCAAGCAGACCCCATGCTCCAGGTCTCTCTCCCATCATTGTCTCTCCTGGTCTCCTTT

6666 GGCGGGTGCCTGTAATCCCAGCTACTCAGGAGGCTGAGGCAGGAGACTCTCTTGAACCTG
GGAGGTGGAAGTTGCAGTGAGCCAAGATTGCACCACTGCCCTCCAGCCTAGGCAACAGAG
CAAGACTCTGTCTCAAAACAGAAAACCTCAGACGTCAGCTTTCTTACTGGCCATGACTGC
AGCATGGTGCTGGCACAAACCACCAGAGGTGGGGTGGATGCCACAAGTTAAGGACACCAT
CCCCAGCATAACTGCTCCCTCTTTAGACACCAGCCACAAGTTCAGGGGTCCCCAACCCAC
[T,A]
CACACTTCTGACCGACTGGCTACAAATTCAGGGACTCCCAAGACCCTGCCAAGTTTGATC
GTTTGCTAACAGACTCACAGAACTCAGGAAATCCTCCATTTTTATCCCAGTTTTATTATG
AAGGACACAGCTCAGGTCCGACCAAATGAAGAAGCATCTCCCCTCCCTCCCCTAGCACAT
CAATGTGATCACCAACCAGGAAGCTTCACTGAGCTTCAGCAGCCAGAGTTTTTATTGGGA
TTTCATTACATCGTCATGACTGATTGAGTCATTGGCCGTATGATCAAGCTTAGTCTCTAG

7498 AACGTGGCTTGATCCCAGATGGGCTTTTAATGACTTCCTCCTGAACTGGATTTATCCTCA
GGCCTTGTCCTGGCCGCCTTACAGGATCACAGCGAGTAGACAGACCCGAATGACTCAGAG
GGACGAGGGCTGGCTGGGCACGCACAGTTCCTGCTCCCAGTTCCATAGGAAGAGTGAAAG
AAAAGAAAGCTGGCCAGGTGCAGTGGCTCACCCCTATAATCCCAGCACTTTGGGAGGCCA
AGGCAGGCAGATCACCTGAGGTCTGGAGTTTGAGGCCAGCCTGGCCAACATGGTGAAACC
[G,A]
TCTCTACTAAAAATAAGAAATTAGCCAGGCATGGTGGTGCGTGCCCGTAATCCCAGCTAC
TCAGGAGGCTGAGGCAGGAGAATCGCTTGAACCCAGGAGGCGGAGGTTACAGTGAGCCAA
GATCACACCACTGCACTTTTGGACAATTGCTAGCTTTCCTTTTCTTTTGAGACAGAGTCT
TGCTTTGTCACCCAGGCTGGGGTGCAGTGTTGTAATCAACAGAGTGAGACTCCATCTCAA
AAAAAAAAAAAAAAAGGAAGGGATTGGGGGAAGAGCCTGGGGCTGGGGGCTGCAGAGATG

7539 TGAACTGGATTTATCCTCAGGCCTTGTCCTGGCCGCCTTACAGGATCACAGCGAGTAGAC
AGACCCGAATGACTCAGAGGGACGAGGGCTGGCTGGGCACGCACAGTTCCTGCTCCCAGT
TCCATAGGAAGAGTGAAAGAAAAGAAAGCTGGCCAGGTGCAGTGGCTCACCCCTATAATC
CCAGCACTTTGGGAGGCCAAGGCAGGCAGATCACCTGAGGTCTGGAGTTTGAGGCCAGCC
TGGCCAACATGGTGAAACCGTCTCTACTAAAAATAAGAAATTAGCCAGGCATGGTGGTGC
[G,T]
TGCCCGTAATCCCAGCTACTCAGGAGGCTGAGGCAGGAGAATCGCTTGAACCCAGGAGGC
GGAGGTTACAGTGAGCCAAGATCACACCACTGCACTTTTGGACAATTGCTAGCTTTCCTT
TTCTTTTGAGACAGAGTCTTGCTTTGTCACCCAGGCTGGGGTGCAGTGTTGTAATCAACA
GAGTGAGACTCCATCTCAAAAAAAAAAAAAAAAAGGAAGGGATTGGGGGAAGAGCCTGG
GCTGGGGGCTGCAGAGATGCTGAAATTGATGACGCCCTTGACACTCTTTTCTTCCCACCC

7557 AGGCCTTGTCCTGGCCGCCTTACAGGATCACAGCGAGTAGACAGACCCGAATGACTCAGA
GGGACGAGGGCTGGCTGGGCACGCACAGTTCCTGCTCCCAGTTCCATAGGAAGAGTGAAA
GAAAAGAAAGCTGGCCAGGTGCAGTGGCTCACCCCTATAATCCCAGCACTTTGGGAGGCC
AAGGCAGGCAGATCACCTGAGGTCTGGAGTTTGAGGCCAGCCTGGCCAACATGGTGAAAC
CGTCTCTACTAAAAATAAGAAATTAGCCAGGCATGGTGGTGCGTGCCCGTAATCCCAGCT
[A,-]
CTCAGGAGGCTGAGGCAGGAGAATCGCTTGAACCCAGGAGGCGGAGGTTACAGTGAGCCA
AGATCACACCACTGCACTTTTGGACAATTGCTAGCTTTCCTTTTCTTTTGAGACAGAGTC
TTGCTTTGTCACCCAGGCTGGGGTGCAGTGTTGTAATCAACAGAGTGAGACTCCATCTCA
AAAAAAAAAAAAAAAAGGAAGGGATTGGGGGAAGAGCCTGGGGCTGGGGGCTGCAGAGAT
GCTGAAATTGATGACGCCCTTGACACTCTTTTCTTCCCACCCCGGCGGCTCTTGCAGCGG

FIGURE 3N

8781 AGGTGGAGGTTTCAGTGAGCCCCGACTGCCATTGCACTCCAGGCTGGGCAACAAGAGTGT
AACTCTGTATCAAAAAAATAAAAATAAAAAAAACACACTCAAAAAATAAAAAGACATTTT
CTTTAGTCCATGTCTGATCCAACAAGAAAGAGGAGGAACCAAGTCAAGAATGAGTGAAGA
AGCTGGGCGCAGTAACTCACACCTGTAATCTCAGCACTTTGGGAGGCCAAAGTGAGAGGA
TCACTTAAGGCCAGAAGTTTGAGACCAGCTTGGGCAACATAGCGAGACCTGCATGTCTAC
[-,A]
AAAAAAAAAAAAAAATTAAAAATTAGCCAGGCATGGTGAAATCACTGAACACATAAAGGC
TGGGCATGGTTGCTCACACTTATAATCGAAACACTTTGGGAGGCTGAGATGGGAGGATCA
CTTGAGGCCAGGAGTTCGAAACCAGCCTGGGAAACATTGTAGTCACAGCTACTTGGGAGG
CTGAGGCAGAAGGATCTCTTGAGCCCAGGAAGTGGCTACAGTGAGCTATAATTGCACGAC
TGCACTCTAGGCTGGGCAATGGAGCAAAACCCTGTCTCAAAAAAATGGGGCAGGGCTGAT

9303 TGAGCTATAATTGCACGACTGCACTCTAGGCTGGGCAATGGAGCAAAACCCTGTCTCAAA
AAAATGGGGCAGGGCTGATAAAGATTAGATTACTGTGTGACTTTGAGCAGCTGCTTTCTC
TCTAGGCTTTGGGGGTCTGTTTGAACAATGAGGGAGTTGGATACCTTGGAGCTTTCTAAG
ATTTCTGTGGCGCCTTTATTGACACCTTGAGAAGTAGCATGCAGTGTTTCTACTTTTGGG
CAATTGGTCACTTCTTTTTTTTTTGAGACAGTCTCACTCTGTCGCCCAGTCTGGGGTGCAG
[G,T]
GGTGTGATACCAGCTCACTGCAACCTCCACCCACAAGGTTCAAGCAATTCTTGCACCTCA
GCCCCCTGAGTAGCTGGGACTACAGGTGACCACATGTGGCTAATTTTTGTATTTTTAGTA
AAGACAGGGTTTCACCATGTTGGCCAGGCTCGTTTCAAACTCCTGGGCTCAAGTGATCCT
CCCTTCTCGGCCTCCCAAAGTGCCGGGATTACAGGTGTGAGCCACCGTGCCCGGCCCAAG
TGCTAGCTTTCTCTCTCTCTTTTTTTTTTTTTTCGAGACGGAGTCTCGCTCTGTCGCCCAG

9860 CTCTTTTTTTTTTTTTTCGAGACGGAGTCTCGCTCTGTCGCCCAGGCTGGAGTGCAGTGGT
GTGGTCTCGGCTCACTGCAAGCCCCGCCTCCTGGGTTCACGCCATTCTCCTGCCTCAGCC
TCCCGAGTAGCTGGGACTACAGGCACCTGCCACCATGCCCGGCTAATTTTTTTTTTTATAT
TTAGTAGAGACAGGGTTTCACCATATTAGGCAGGATGGTCTCGATCTCCTGACCTCGTGA
TCCGCCCGTCTCGGCCTCCCAAAGTGCTGCGATTACAGGCATGAGCCACCACGCCCGGCC
[A,G,C]
TACCAAGTGCTAGCTTTCATTTGACGCAGTGAATGTTTCTTGTACACCTGGCAGGTGCCT
GGCACTGCATAGGCACTGTTGAGATGTGAAGGTGGCCCTGGGGACAGAAAATTATACTGG
GCTTGACTGTGTGTCTCCATCCCTTGACATCAGCCAAGCCAGCAGCTGCTTTACATACAT
GATGAGCAGACAGCTGCTTGAAAGAGATGAGGAAACTCCCAGACCAACGGCTCTTACCAG
AGGGCCAAGGGAGGTCCCCACAGAGTCAGAGGCTGCAGCTGGTCCCTGAAATCCAGGCAG

11629 GGAGACAGGGTATCACTGTCATTGAGGCTGGAGTGCAGTGATGCGATCACAGCTCACTGC
AGCCTCAACCTCCCAGGCTCAAGTGATCCTCCCACCTCTGCCTCCCAAGTAGCTGGGACT
ACAGGCACGGGCCACCACGCCTGGCTAGGCATTCTGTTATGTAATTATCAATTGTATCTT
ATAGTTCAGTGATCACATTTTGGAAATGTAACATTGATACCATTATCTAATACACAGACC
ATATTCAAATTTTGCCTATTGTCTCTATACTGAACTACTGAGCTGTCCTTTATAGCAATC
[A,G,T]
CCCCCTCATCCACAGTCCAGTCCATGATCAACATTGCATTTAATCGTCATGTGTCATCAG
TATCTTTTTTTTTTTTTTTTTTTTTGAGACGGAATTTTGCTCTTGTTGCCCAGGTTGGAGCGC
AATGGCGCAATCTTGGCTTATTGCAACCTCCGCCTTTGGGCTTAAGTGATTCTCCTGCCT
CAGCCTCCTAAGTAGCTGAGATTACAGGCGTGCACCATTATGCATGCCTAATTTTTGTAT
TTTTATTAGAGACGGGGTTTTACCATGTTGCCCTGGCTGGTCTTGAACTCCTGACCTCAA

12044 GAGCGCAATGGCGCAATCTTGGCTTATTGCAACCTCCGCCTTTGGGCTTAAGTGATTCTC
CTGCCTCAGCCTCCTAAGTAGCTGAGATTACAGGCGTGCACCATTATGCATGCCTAATTT
TTGTATTTTTATTAGAGACGGGGTTTTACCATGTTGCCCTGGCTGGTCTTGAACTCCTGA
CCTCAAATGATCCACCCACCTCAGCCTCCCAAAATGCTGGGTTTACAGGCATGAGCCACT
GCGTCTGGCCATTTCCTCAGCCTTTCATTGCCCTTCATGATCTTGACATTTTTGAAGTGT
[A,G]
CAGGCCAGTCATTAAAGTAAAATGTTTTTCCTTTTTTTTTTTTTTTTTTTTTTAAAAAGAGA
CAGGGTCTCACTGTGTTGCCCAGGCTGGTCTCAGACTCCTAGGCTCAAGTGATCCTCCCG
CCTCAGCTTCCCAAAGTGCTGGGATTACAGGCGTGAGCCATCGTACCTGCCCTCGCATTT
GGGTTTGACTGATGTTTCCTCTTAGGGAGACAGGCTCTGCAGGTTTGGCCTGATACTGCA

FIGURE 3O

TAAGTGATCCTCTGTCCTTCCGAGTGGATCTTGCCAGGAGACATATGATGTCAGTGTGCC

12348 GCCAGTCATTAAAGTAAAATGTTTTTCCTTTTTTTTTTTTTTTTTTTTTAAAAAGAGACAG
GGTCTCACTGTGTTGCCCAGGCTGGTCTCAGACTCCTAGGCTCAAGTGATCCTCCCGCCT
CAGCTTCCCAAAGTGCTGGGATTACAGGCGTGAGCCATCGTACCTGCCCTCGCATTTGGG
TTTGACTGATGTTTCCTCTTAGGGAGACAGGCTCTGCAGGTTTGGCCTGATACTGCATAA
GTGATCCTCTGTCCTTCCGAGTGGATCTTGCCAGGAGACATATGATGTCAGTGTGCCCTT
[T,G]
GCTGAGGATGTTCACTTTGATTACTTGTTTTTTCTGTACTGTAAGGATTTTTTTCCCTTT
GTCATCAATAAACCATTTGTGAGATTTGAGTCTGTAAATATCCTGTTCCCAAAAACCCTT
CCCCAAATGATTTGAGCATCTATTGATGATTCTTGCCTGTAGCGATTATTACTAGGGTGG
CTACCAAATGCTGAATTTCTAACTCTGTTCTTCCTTCTGCATTTGTTACTGTAAGGAAGA
GCTTCTCCCCCATACGAGAATAGTCTTTTTGTTTGCTTGGTTGTTTTTTTGAGATAGGGT

13479 AACCAGCTCACGCCTATAATCCCAGCACTTTGGGAGGCCAAGGTGGGTGGATTACCTGAG
GTCAGGAGTTCAAGACCAGCCTGACCAACATAGAGAAACCCCATCTGTACTAAAAATACA
AAATTAGCCAGGCATGGTGGCACATGCCTGTAATCCCAGCTACTCAGGAGCCTGAGGCAA
GAGAATCACTTGAACCTGGGAGGCGGAAGTTGCAATGAGCCGAGATCACTCCATTGCACT
CCAGCCTGGGCAACAAGAGCAAAACTCTGTCTCAAAAAAAAAAAAGAAAAGAAAAGAAAA
[G,A,C]
CAGGTCCCTAACACCGAAGAGTTAAAAGAAATAAGTAAATTTGGCAAATTGGTCTTTTTG
TGAGTTAGCTTATAGGCAACTGATCGAGGGTCTCTTTCCCGTCTTCACCCTGCAATTGTG
GCTCAGGGCAAGCTGCCAGCTCCCTCCTGCCAATGCAGGAGCAATAGAGCTTGGCCTCCT
CTTGCAGGGCGAGTTTGGGAGTCAGATATGAAGCCACTAATCCGGGACCTTTTTGGGACC
CAAGGCACTCATCTGCCCCAAGCATACCAGGCAGGCCAGGTGCAATGACTCATGTCTGTA

14360 GTGAGCCACTGCGCCCGGCCAGTCCTAGCCCTTTGGGAGGCTAAGGCGGGCGGATTGCAT
GAGCTCAGGAGTTCGAGACCAGCCTGGGAAATGTGGTGTAACCCCGTCTCTACTAAAAAT
ACAAAAAAAATTAGCTGGGTGTGGTGGTGTGCACCTGTAATCCCAGCTACTCAGGAGGCT
GAGGTACGAGAATCGCTTGAACTCAGGAGGCAGAGGCTGCAGTGAGCTGAGATTGTGCCA
TTGCACTCCAGCCTGGGTAACAGAGTGAGATTCTGTCTCCAAAAAAAAAAAAAAAAAAA
[G,A,T]
TCGAGACCAAACATACCTGGGATTTGGAAGGATAGATCTGTTCCCCCAGGGTGGAGACAA
TGGTCCATTGAATGGGAACAGCTGAGCATCTTGTGTGGGTGGCCAGTGCCTACAAGCGTG
CCACCTTTCTCCAGCTCACACCTGTGGCAGACATCAGTAATTGATTACAGAATTCCTCCC
CTGAAACCAGAACTCGGTGTTCTGGCCATCTGCTACTTCCCAGTCACACGAAGTAGAATC
CTCCACCTGCTCACCCTGGATCTGGTGCCCTTCGCCTTGGTTTCCTGTTGGGGCTCTGAG

14371 CGCCCGGCCAGTCCTAGCCCTTTGGGAGGCTAAGGCGGGCGGATTGCATGAGCTCAGGAG
TTCGAGACCAGCCTGGGAAATGTGGTGTAACCCCGTCTCTACTAAAAATACAAAAAAAAT
TAGCTGGGTGTGGTGGTGTGCACCTGTAATCCCAGCTACTCAGGAGGCTGAGGTACGAGA
ATCGCTTGAACTCAGGAGGCAGAGGCTGCAGTGAGCTGAGATTGTGCCATTGCACTCCAG
CCTGGGTAACAGAGTGAGATTCTGTCTCCAAAAAAAAAAAAAAAAAAAAATTCGAGACCAA
[A,G]
CATACCTGGGATTTGGAAGGATAGATCTGTTCCCCCAGGGTGGAGACAATGGTCCATTGA
ATGGGAACAGCTGAGCATCTTGTGTGGGTGGCCAGTGCCTACAAGCGTGCCACCTTTCTC
CAGCTCACACCTGTGGCAGACATCAGTAATTGATTACAGAATTCCTCCCCTGAAACCAGA
ACTCGGTGTTCTGGCCATCTGCTACTTCCCAGTCACACGAAGTAGAATCCTCCACCTGCT
CACCCTGGATCTGGTGCCCTTCGCCTTGGTTTCCTGTTGGGGCTCTGAGGGACAGGTGGG

14383 CCTAGCCCTTTGGGAGGCTAAGGCGGGCGGATTGCATGAGCTCAGGAGTTCGAGACCAGC
CTGGGAAATGTGGTGTAACCCCGTCTCTACTAAAAATACAAAAAAAATTAGCTGGGTGTG
GTGGTGTGCACCTGTAATCCCAGCTACTCAGGAGGCTGAGGTACGAGAATCGCTTGAACT
CAGGAGGCAGAGGCTGCAGTGAGCTGAGATTGTGCCATTGCACTCCAGCCTGGGTAACAG
AGTGAGATTCTGTCTCCAAAAAAAAAAAAAAAAAAAAATTCGAGACCAAACATACCTGGGA
[T,G]
TTGGAAGGATAGATCTGTTCCCCCAGGGTGGAGACAATGGTCCATTGAATGGGAACAGCT
GAGCATCTTGTGTGGGTGGCCAGTGCCTACAAGCGTGCCACCTTTCTCCAGCTCACACCT
GTGGCAGACATCAGTAATTGATTACAGAATTCCTCCCCTGAAACCAGAACTCGGTGTTCT

FIGURE 3P

GGCCATCTGCTACTTCCCAGTCACACGAAGTAGAATCCTCCACCTGCTCACCCTGGATCT
GGTGCCCTTCGCCTTGGTTTCCTGTTGGGGCTCTGAGGGACAGGTGGGCACTGGCCTGAC

17112 CAGAGGGACTTCCAGGTGCTCACCCCTGCCCCATCAACACAGGTCGGAAAAGGGCTCTGG
GAACCATTGAAAGAAGAGCGAGCAGGCCAGGCATAGTGGCTCACGCCTGTAATCCCAACA
CTTTGGGAGGTTAAGGAGAGAGGATACTTTGAGACCAACCTGGGCAACATAGCAAGACCC
CGTCTCTACAAAAAAATTTTAAATTAACCGAGCTTGGCAATGTGCACCTGTCATCCCAGC
TACTCGGGGGGCTGAGGTGGGAGGCTCGCTTGAGCCCAGGAGTTGGAGGCTGCAATGAGC
[T,C]
ATGATCGCACCACTGCACTCCAGCCTGGGGAACAAGGCAAGACCCTGTGTCCAAAAAAAA
TAAAAGTAACTGCATTGGTCGGGCATAGTGGCTCACGCCTGTAATCCCAGCACTTTGGGA
GGCTGAGCCGGGCGGATCACCTGAGGTCAGGAGTTCGAGACTACCCTGGCCAACATGGCA
AAACCCCGTCTCTACTAAAAATACAAAAATTAGCCCAGCATGATGGTGGTGAGTGCCTGT
CATCCAGGCTACTCAGGAGGCTGAGGCAGGAGAATTTCTTGAACTCAGGAGGCGGAGGTT

18360 CCTGTTATTCTGGCACTTTGGGAGCCCAAGGCAAGAGGATCACTCGAGGCCAGGAATTCA
AGGCTGCAGTGAGCTGTGATCTCACCACTGCACTCCAGCCTGGACCACACAGCAAGACCC
TATCTCAAAAACTAAAATAAAATTCAGAGCTTTCCTTAAGGATTTGAATAAAATTACAAA
TCCATCTTTAGAAATAAAGTGCTCAGGCCAGGTGCAGTGGCTCATGCCTATAATCTCAGC
ACTTTCAGAGGCTGAGGCCAGCAGATCACCTGAGGTCAGGAGTCCAAGACCAGCCTGGCC
[-,A]
ACATGGTGAAACCCCGTCTCTACTAAAAATACAAAAATTAGCTGGGCCTGGTGGCAGGCA
CCTGTAATCCCAGCACTTTGGGAGACTGAGGTTGGCAGATCACCTGAGGTCAGGAGTTCG
AGACCATCCTGGTAACCCGTCTCTACTAAAAATACAAAAAATTAGCCGGGCAAGGTGGCA
GGTGCCTGTAGTCCCAGCTACTCGGGAGACTGAAGCAGGAGAATGGCGTTGAACCCAGGG
GGCAGAGCCTGCAGTGAGCCAAGATCGCACCACTGCGCTCTAGCCTGGGTGACAGCGAGA

18679 TCTACTAAAAATACAAAAATTAGCTGGGCCTGGTGGCAGGCACCTGTAATCCCAGCACTT
TGGGAGACTGAGGTTGGCAGATCACCTGAGGTCAGGAGTTCGAGACCATCCTGGTAACCC
GTCTCTACTAAAAATACAAAAAATTAGCCGGGCAAGGTGGCAGGTGCCTGTAGTCCCAGC
TACTCGGGAGACTGAAGCAGGAGAATGGCGTTGAACCCAGGGGGCAGAGCCTGCAGTGAG
CCAAGATCGCACCACTGCGCTCTAGCCTGGGTGACAGCGAGATTCCGTCTCAAAAAAAAA
[A,G]
CACTTGGAGGAAGCCTCACAGAGTCCTGTGCTGGACCACACCCTGGGGATCCAGTCCTGG
CCTCCAGCCCCATTTCTGTACCACCCTGAGACCATGGGATCTTCCTCAGGTTGGATTACC
TTGTATCCAAGGTGTGGACCCTATGGGCTCCTGCTAGGTGTAACTTGACACAACGGGTTC
CGTTGTCAGGTGCAATTTAGAAACTCTGGGCTAGGCCAAGCGCAGTGGCTCACACCTGAA
TTCCCAAACTTTGGAAGGCCGAGGCAGGAGGGTCACTAGAGGTCAGGAGGTCAAGACCAG

18703 TGGGCCTGGTGGCAGGCACCTGTAATCCCAGCACTTTGGGAGACTGAGGTTGGCAGATCA
CCTGAGGTCAGGAGTTCGAGACCATCCTGGTAACCCGTCTCTACTAAAAATACAAAAAAT
TAGCCGGGCAAGGTGGCAGGTGCCTGTAGTCCCAGCTACTCGGGAGACTGAAGCAGGAGA
ATGGCGTTGAACCCAGGGGGCAGAGCCTGCAGTGAGCCAAGATCGCACCACTGCGCTCTA
GCCTGGGTGACAGCGAGATTCCGTCTCAAAAAAAAAGCACTTGGAGGAAGCCTCACAGAG
[T,C]
CCTGTGCTGGACCACACCCTGGGGATCCAGTCCTGGCCTCCAGCCCCATTTCTGTACCAC
CCTGAGACCATGGGATCTTCCTCAGGTTGGATTACCTTGTATCCAAGGTGTGGACCCTAT
GGGCTCCTGCTAGGTGTAACTTGACACAACGGGTTCCGTTGTCAGGTGCAATTTAGAAAC
TCTGGGCTAGGCCAAGCGCAGTGGCTCACACCTGAATTCCCAAACTTTGGAAGGCCGAGG
CAGGAGGGTCACTAGAGGTCAGGAGGTCAAGACCAGCTTGGACAACATAATGAGATCCCA

24472 CTGGGAGGCGGAGGTTGCAGTGAGCCGAGATCATGCCACTGCGCTCCAGCCTGGGTGACA
GAGCAAGACTCCGTCTGAAAAAAAAAACAAAAGAATTCCTGTCTTCTCTCCGAAACAAAG
CAGCATCAGTGCCCCCGCAGGTGGGAGGGAGCGCTTGCAGGAGGGAGCAGTGGGTCCGCC
ACGACGGTCTGGGGAGCAGGTGGGGAGGGGGCAGAGGGTGCAGCGTGTGGTGGGAGGGAG
GAAGCCACACTGCTATCTTCAGGTGCTTCCCGCAGCTCCATTTGCAAAGAGCGGATGGGT
[T,C]
TGGGGAAGGAAGGGGTCCCCACCCTGTGCCAATACAGCGTATCAGAGGTATGTTCTCTGG
GCTGTCTACGGGTTGGCTTGGGGTCCTGGGGAGGGGCAGGCCAAGCGGGCAGTACTAGGA

FIGURE 3Q

TCGGGTCCCAGCATGACCCGGCTTCACCTTCCCAGAACAAGAATGTGGTGGTGGCTGACT
TCGGGCTGGCGCGTCTCATGGTGGACGAGAAGACTCAGCCTGAGGGCCTGCGGAGCCTCA
AGAAGCCAGACCGCAAGAAGCGCTACACCGTGGTGGGCAACCCCTACTGGATGGCACCTG

24542 CCGTCTGAAAAAAAAAACAAAAGAATTCCTGTCTTCTCTCCGAAACAAAGCAGCATCAGT
GCCCCCGCAGGTGGGAGGGAGCGCTTGCAGGAGGGAGCAGTGGGTCCGCCACGACGGTCT
GGGGAGCAGGTGGGGAGGGGGCAGAGGGTGCAGCGTGTGGTGGGAGGGAGGAAGCCACAC
TGCTATCTTCAGGTGCTTCCCGCAGCTCCATTTGCAAAGAGCGGATGGGTTTGGGGAAGG
AAGGGGTCCCCACCCTGTGCCAATACAGCGTATCAGAGGTATGTTCTCTGGGCTGTCTAC
[G,A]
GGTTGGCTTGGGGTCCTGGGGAGGGGCAGGCCAAGCGGGCAGTACTAGGATCGGGTCCCA
GCATGACCCGGCTTCACCTTCCCAGAACAAGAATGTGGTGGTGGCTGACTTCGGGCTGGC
GCGTCTCATGGTGGACGAGAAGACTCAGCCTGAGGGCCTGCGGAGCCTCAAGAAGCCAGA
CCGCAAGAAGCGCTACACCGTGGTGGGCAACCCCTACTGGATGGCACCTGAGATGATCAA
CGGTGAGTGGTTCAGCCCTGCCCATCATGGCCCTCACGGGAAGCCATGGGGGAGCCCAGG

24900 CCAGCATGACCCGGCTTCACCTTCCCAGAACAAGAATGTGGTGGTGGCTGACTTCGGGCT
GGCGCGTCTCATGGTGGACGAGAAGACTCAGCCTGAGGGCCTGCGGAGCCTCAAGAAGCC
AGACCGCAAGAAGCGCTACACCGTGGTGGGCAACCCCTACTGGATGGCACCTGAGATGAT
CAACGGTGAGTGGTTCAGCCCTGCCCATCATGGCCCTCACGGGAAGCCATGGGGGAGCCC
AGGAGAGCTGTAACCTCCCAAGCCCCTGGCCCCTCCCAGCCTCCTTGGCTCTTCAGTTAC
[C,T]
CTGTGGGTCCTGTTGCTCCTATAACACACTTAGTGGCAGCCAGGCACGGTGGCTCACGCC
TGTAATCCCAGCACTTTGGGAGGCTGAGGTGAGTGGATCACCTGAGGTCAGTAGTTGGAG
ACCAGCCTAGCCAACATGGTGAAACCCCCATTCTTTACTAAAAATACAAAAATTAGCTGG
GCATGGTGGCGGGTGCCTGTAATCCCAGCTACTAGGGAAGCTGAGGCAGGAGAATCGCTT
GAACCTGGGAGGCAGAGGTTGCAGTGAGCCGAGATCGCGCCATTGCACTCCAGCCTGGGT

31542 GGTGGGACCCACCCACCCCCATCCAGGAACCGTGACGTCCAAGGAACCAAACCCAGACGC
AGAACAATAAAATAAATTCCGTACTCCCCACCCAGGTCCTGCGTGGCGATGTGTGTCTGG
GGCCCTGGGGAAATAGTCAAGGTAAGAGGAGTTAGTCTTCCCTGACCAGAAGACAAGGAT
GAGTGTGGTGGCTCATGCCTGTGATCCCAGCACTCTGGGAGGCTGAGACAGGACGATCCC
TTAAGCCCAGGAGTTCAAGACCAGTCTGGACAACATAGTGAGATCCTGTCTCTACAAAAA
[A,T]
TTTTTTTTAATTAGTTGGGCAGAGGCCAGGTGTGGTGGCTCATGCCTGTAATCCCAGCAC
TTTGGGAGGCAGAGGCGGGTGGATCACCTGAAGTTAGGAGTTCAAGACCAGTCTGGCCAA
CATGGTGAAAACTCGTCTCTACTAAAAATACAAAAATTAGCCGGGCGTGGTGGCACATGC
CTGTAGTCCTAGCTACTTGGGAGACTGAGGCAGGAGAATCGCTTGAACCCGAAAGGCAGA
GGTTGCAGTGAGCCGAGGTGGTGCCATTCCACTCCAGCCTGGGAAAGAGCGAGACTTTGT

32344 CTTGGGGGGTTGAGGCAGGAGAATTGCTTGAACCCAGGAGGCAGAGGTTGCAGTGAGCCG
AGATTGCACCATTGCACCCCAGCCTGGGCAACAAGAGCGAAACTCCATCTCAAAAAAAAA
AAAAAAAATTAGTTGGGCATGGTGGCATGCACCTATAGTCCCAGCTACTCAGGAGGCTGA
GGTGGGAGGATCCTTTGAGCCCAAGAGATCAAGGCTGCAGTGAGCCATGTTTGCACCACT
GCACTCCAGCCTGGGCAACAAAACAAGACTCTGTCTCAAAAAAAAAAAAAAAAAAAAAAA
[T,A,G,C]
GCAGGGATGGAGGGGGGAAGAGAACACAGCCCAGTTTTAGGTGGAGCTGAGGTGGTGGCC
CAGCCAGGACAAGTGAAGAGTCTTCAGAGGCTGGGTTTGGAGGGCCGTGCATATTCCGGA
GGTACTGCTTTCATACTTAAATGTTTTCTTGTAAAACTCACACCTGTAATCCCAGCACTT
TGGGAGGCCAAGGTGGGCGGATCATCTGAGGTCGGGGGTTCAAGACCAACCTGACCAACA
TGGAGAAACCCCGTCTACTAAAAATACAAAAAATTAGCCAGGTGTGGTGACACATGCCTG

FIGURE 3R

SEQUENCE LISTING

```
<160> NUMBER OF SEQ ID NOS: 8

<210> SEQ ID NO 1
<211> LENGTH: 1842
<212> TYPE: DNA
<213> ORGANISM: Homo sapiens

<400> SEQUENCE: 1

atgctgttgg cttcagcccc aagaagacgc cgcttcctcc agagggctaa gtgttgtgac     60

tgcagtgcct ccctgtcgca ccagtactat gagaaggatg ggcagctctt ctgcaagaag    120

gactactggg cccgctatgg cgagtcctgc catgggtgct ctgagcaaat caccaaggga    180

ctggttatgg tggctgggga gctgaagtac caccccgagt gtttcatctg cctcacgtgt    240

gggaccttta tcggtgacgg ggacacctac acgctggtgg agcactccaa gctgtactgc    300

gggcactgct actaccagac tgtggtgacc cccgtcatcg agcagatcct gcctgactcc    360

cctggctccc acctgcccca caccgtcacc ctggtgtcca tcccagcctc atctcatggc    420

aagcgtggac tttcagtctc cattgacccc ccgcacggcc caccgggctg tggcaccgag    480

cactcacaca ccgtccgcgt ccagggagtg gatccgggct gcatgagccc agatgtgaag    540

aattccatcc acgtcggaga ccggatcttg gaaatcaatg gcacgcccat ccgaaatgtg    600

cccctggacg agattgacct gctgattcag gaaaccagcc gcctgctcca gctgaccctc    660

gagcatgacc ctcacgatac actgggccac gggctggggc ctgagaccag ccccctgagc    720

tctccggctt atactcccag cggggaggcg ggcagctctg cccggcagaa acctgtcttg    780

aggagctgca gcatcgacag gtctccgggc gctggctcac tgggctcccc ggcctcccag    840

cgcaaggacc tgggtcgctc tgagtccctc cgcgtagtct gccggccaca ccgcatcttc    900

cggccgtcgg acctcatcca cggggaggtg ctgggcaagg gctgcttcgg ccaggctatc    960

aaggtgacac accgtgagac aggtgaggtg atggtgatga aggagctgat ccggttcgac   1020

gaggagaccc agaggacgtt cctcaaggag gtgaaggtca tgcgatgcct ggaacacccc   1080

aacgtgctca agttcatcgg ggtgctctac aaggacaaga ggctcaactt catcactgag   1140

tacatcaagg gcggcacgct ccggggcatc atcaagagca tggacagcca gtacccatgg   1200

agccagagag tgagctttgc caaggacatc gcatcaggga tggcctacct ccactccatg   1260

aacatcatcc accgagacct caactcccac aactgcctgg tccgcgagaa caagaatgtg   1320

gtggtggctg acttcgggct ggcgcgtctc atggtggacg agaagactca gcctgagggc   1380

ctgcggagcc tcaagaagcc agaccgcaag aagcgctaca ccgtggtggg caacccctac   1440

tggatggcac ctgagatgat caacggccgc agctatgatg agaaggtgga tgtgttctcc   1500

tttgggatcg tcctgtgcga gatcatcggg cgggtgaacg cagaccctga ctacctgccc   1560

cgcaccatgg actttggcct caacgtgcga ggattcctgg accgctactg ccccccaaac   1620
```

-continued

```
tgcccccga gcttcttccc catcaccgtg cgctgttgcg atctggaccc cgagaagagg   1680

ccatcctttg tgaagctgga acactggctg gagaccctcc gcatgcacct ggccggccac   1740

ctgccactgg gcccacagct ggagcagctg gacagaggtt tctgggagac ctaccggcgc   1800

ggcgagagcg gactgcctgc ccaccctgag gtccccgact ga                     1842
```

<210> SEQ ID NO 2
<211> LENGTH: 613
<212> TYPE: PRT
<213> ORGANISM: Homo sapiens

<400> SEQUENCE: 2

```
Met Leu Leu Ala Ser Ala Pro Arg Arg Arg Arg Phe Leu Gln Arg Ala
 1               5                  10                  15

Lys Cys Cys Asp Cys Ser Ala Ser Leu Ser His Gln Tyr Tyr Glu Lys
            20                  25                  30

Asp Gly Gln Leu Phe Cys Lys Lys Asp Tyr Trp Ala Arg Tyr Gly Glu
        35                  40                  45

Ser Cys His Gly Cys Ser Glu Gln Ile Thr Lys Gly Leu Val Met Val
    50                  55                  60

Ala Gly Glu Leu Lys Tyr His Pro Glu Cys Phe Ile Cys Leu Thr Cys
65                  70                  75                  80

Gly Thr Phe Ile Gly Asp Gly Asp Thr Tyr Thr Leu Val Glu His Ser
                85                  90                  95

Lys Leu Tyr Cys Gly His Cys Tyr Tyr Gln Thr Val Val Thr Pro Val
            100                 105                 110

Ile Glu Gln Ile Leu Pro Asp Ser Pro Gly Ser His Leu Pro His Thr
        115                 120                 125

Val Thr Leu Val Ser Ile Pro Ala Ser Ser His Gly Lys Arg Gly Leu
    130                 135                 140

Ser Val Ser Ile Asp Pro Pro His Gly Pro Pro Gly Cys Gly Thr Glu
145                 150                 155                 160

His Ser His Thr Val Arg Val Gln Gly Val Asp Pro Gly Cys Met Ser
                165                 170                 175

Pro Asp Val Lys Asn Ser Ile His Val Gly Asp Arg Ile Leu Glu Ile
            180                 185                 190

Asn Gly Thr Pro Ile Arg Asn Val Pro Leu Asp Glu Ile Asp Leu Leu
        195                 200                 205

Ile Gln Glu Thr Ser Arg Leu Leu Gln Leu Thr Leu Glu His Asp Pro
    210                 215                 220

His Asp Thr Leu Gly His Gly Leu Gly Pro Glu Thr Ser Pro Leu Ser
225                 230                 235                 240

Ser Pro Ala Tyr Thr Pro Ser Gly Glu Ala Gly Ser Ser Ala Arg Gln
                245                 250                 255

Lys Pro Val Leu Arg Ser Cys Ser Ile Asp Arg Ser Pro Gly Ala Gly
            260                 265                 270

Ser Leu Gly Ser Pro Ala Ser Gln Arg Lys Asp Leu Gly Arg Ser Glu
        275                 280                 285

Ser Leu Arg Val Val Cys Arg Pro His Arg Ile Phe Arg Pro Ser Asp
    290                 295                 300

Leu Ile His Gly Glu Val Leu Gly Lys Gly Cys Phe Gly Gln Ala Ile
305                 310                 315                 320

Lys Val Thr His Arg Glu Thr Gly Glu Val Met Val Met Lys Glu Leu
                325                 330                 335
```

-continued

```
Ile Arg Phe Asp Glu Glu Thr Gln Arg Thr Phe Leu Lys Glu Val Lys
            340                 345                 350

Val Met Arg Cys Leu Glu His Pro Asn Val Leu Lys Phe Ile Gly Val
        355                 360                 365

Leu Tyr Lys Asp Lys Arg Leu Asn Phe Ile Thr Glu Tyr Ile Lys Gly
    370                 375                 380

Gly Thr Leu Arg Gly Ile Ile Lys Ser Met Asp Ser Gln Tyr Pro Trp
385                 390                 395                 400

Ser Gln Arg Val Ser Phe Ala Lys Asp Ile Ala Ser Gly Met Ala Tyr
                405                 410                 415

Leu His Ser Met Asn Ile Ile His Arg Asp Leu Asn Ser His Asn Cys
            420                 425                 430

Leu Val Arg Glu Asn Lys Asn Val Val Val Ala Asp Phe Gly Leu Ala
        435                 440                 445

Arg Leu Met Val Asp Glu Lys Thr Gln Pro Glu Gly Leu Arg Ser Leu
    450                 455                 460

Lys Lys Pro Asp Arg Lys Lys Arg Tyr Thr Val Val Gly Asn Pro Tyr
465                 470                 475                 480

Trp Met Ala Pro Glu Met Ile Asn Gly Arg Ser Tyr Asp Glu Lys Val
                485                 490                 495

Asp Val Phe Ser Phe Gly Ile Val Leu Cys Glu Ile Ile Gly Arg Val
            500                 505                 510

Asn Ala Asp Pro Asp Tyr Leu Pro Arg Thr Met Asp Phe Gly Leu Asn
        515                 520                 525

Val Arg Gly Phe Leu Asp Arg Tyr Cys Pro Pro Asn Cys Pro Pro Ser
    530                 535                 540

Phe Phe Pro Ile Thr Val Arg Cys Cys Asp Leu Asp Pro Glu Lys Arg
545                 550                 555                 560

Pro Ser Phe Val Lys Leu Glu His Trp Leu Glu Thr Leu Arg Met His
                565                 570                 575

Leu Ala Gly His Leu Pro Leu Gly Pro Gln Leu Glu Gln Leu Asp Arg
            580                 585                 590

Gly Phe Trp Glu Thr Tyr Arg Arg Gly Glu Ser Gly Leu Pro Ala His
        595                 600                 605

Pro Glu Val Pro Asp
    610
```

<210> SEQ ID NO 3
<211> LENGTH: 33112
<212> TYPE: DNA
<213> ORGANISM: Homo sapiens

<400> SEQUENCE: 3

```
caaagtgctg ggattacagg cgtgagccac cgtgcccggc aatattaaag cgattttaag     60

gccaaggctg gtaactcacg cctgtaatcc cagcactttg ggaggctgag gcaggaggac    120

tgcttgaggc caggagtttg agatcaacct aggcaacata gtgagactcc atctctacaa    180

aaaaattagc caggcgtggt ggtgcgtacc tgtagtccca gctactcagg aggctgagat    240

gggaggatca tttgaaccca ggatgtcgaa gctgcagtga gctgtgatca cgccactgca    300

ctctggcctg ggcaacagag cgagacactg tctcaaattt ttaaaaagcg attttacaaa    360

tgaggtgcag agttcagtca cttgccaaaa gtctcacagc gcgtgaggag tagaatcagg    420

actcgaaccg aggcagcctg gcttcagagc ctacagtgta accacagctt agtcccacac    480

ctcccagacc aacagggtcc ctgccttcta gtgggcaaga cactcagtga acaaatgtag    540
```

-continued

```
tgtcaggtat tgggggacag cactctcagg aagtgatgtt taagggacag aattgaaggg    600
agcagtgttt agaggatgtc gggggtaggg ccggtgcatg tgcaaaggcc ttggggtggg    660
aatgtgcttg gcacaactga ggaccacaaa gccagcgtgc gggagtgcag tcagtggcca    720
ggggtgcata gagccttgtg ggccccgtgg aaggtgccgt tggctgtaca gctttttttt    780
tttttttttt tttttttttt tgagacagag tctcgctttt gttgcccagg ctggagtgca    840
gtggcgtgat ctcagctcac tgcaacctcc gcctcccggg ttcaagcgat tctcctgcct    900
cagcttcctg gtagctggga ctacaggcgc ccaccaccac acctggctaa tttttgtgtt    960
tttaatagag acggggtttc accatgttag ccaggctggc ctcaaactcc tgacctcaag   1020
cgatctgtct acctcagcct cccaaagtgc tggggttaca ggcatgagcc actgcgcaca   1080
ggcagctgtg catctttgaa tgtcataacc tgagcatctg agagctgctc ctgtcccctg   1140
gcccctgctc ttgaggaagt cccacgctga taggacagac agggtcataa gtgctgtgat   1200
gggggcctgc aggctgctgg agggctcagc cgggaccaga tgctgcccct ctttgtagag   1260
tgggacaatt gctgcaggcc catgggacct ctggtattag ccctgagggt tgtcactccg   1320
gggcctgccc ctttctgtgt tctgacctcc cagccccttg caggccccgc ctcccggaag   1380
gttatgacca ggcttggact ggtccaggct tccctttggc tcacatactg cctctgcgag   1440
gtcccctcca ggaagcctcc tgtgcacaac ccccagggct gccgcatccc tggtagcatc   1500
tccttggcag ctgggtgggc tggccctggg caaggagggc tgagcatgct gctggcctgt   1560
ggggttggag cagcggcggg atgcaacctc cctttcttca ggggaccttt ttggcgaaga   1620
caaactgtcc ataggaagtc gacctctgtt cccttggggg cagcagtgga agaggcagct   1680
gcttttgagc ttgtccctgt ccccagagaa gcctgaggcc ttcagtgccg ttgccagggc   1740
cgaggctgag gagcctacag cgtgtgttca ggactgaggg ccagggacgg gccacaggct   1800
ccctgcctgg ggtccaagcc tagatcgctc gctccccacc cgcaccaaag cccaggcaaa   1860
gggtgcttca gccacttcct gttgcaggct cagaccaagt cccctggcac ccacgcggct   1920
gcagcctcct cctgtgcgct gcagccacgc tggccccacc ctctgcagcc tccaatcctg   1980
agcccctgag ggaggatggg gaagcagctg gtctggccac ccctgccctc ccttagacct   2040
ccagagcccc cagtgtagcc acagaggatg ctgttggctt cagccccaag aagacgccgc   2100
ttcctccaga gggctaagta agtgggaatc cccctcccta cttgtcctgg gctccaggca   2160
gggcccctgg tgtaaggcct ggggctggaa gccgacccac ctaggtccag gctctggggc   2220
agaactgaaa ctccttggtt actgtcggct gcagcctggg agcaggccac tgccaaagct   2280
gtgggtcctt ccaggacagt ctccccatga ggccggtcct ccacctgctg tttcttcaca   2340
cctggtggcc agggatgtgg ccctgggtag aacgatgatt ctccactcct gtcattatgg   2400
aagccaccgc tgtctcccag cccagccagc cacctgggct gcagagcacc cctttcatgc   2460
cctccgggtg cctcccccctt ctcctgcccc agcctggctt tgtcctaccc tgctctcagg   2520
gaggggtacc ctggagtggg gccagggcat ggctctcccc cgagggagtt cctctctggc   2580
tgtccccagg gcagctctgc acagcctcag tacctggcgc acctcccttg acatccttct   2640
tagggacagt caggcactct gtgtggggca ctcaagagag ccaggcccgt cagcctctag   2700
ctcctgccag aatgcaggcc tgaggggtga ggggcggggc aggggcaggg gcagggacag   2760
gaactccggc gtgctctcca tccgcaaagg ttcactgagg ccccgagccc cagccactga   2820
gccaccaagt cagcctgggc caggcctggg tgccctgtct gcaatggagg cagagacggg   2880
```

-continued

```
gtctcggggc agttctgagg atgctgggtg cacagcgggg gcctcgccgg caggaatcac   2940
ttatgctctc tcctgggcca agctttgtgg atgcccagcc tggggccgcg gggagctggc   3000
aggtcagtgg cagacactgg tgggcagacc tagtgtctgg tagaacaggc atcaaggaag   3060
tggtgaccgg agggaagcca agtgcactca aaccctcggg tgagtcatca ccgccgggtc   3120
tttcacagct gctgaaagtg agcaacagtg atgaaggttt gtgagtttct gcgtgagcga   3180
gtgaatggac cagtagcagt ttccaggttg tggaagagcg ttccctcccc gggatgggga   3240
cacttggtta cagcaattcc taatccccca cccacccacc gcccactgca gaggtatgcg   3300
ggggccctgc ttcctgcagg caggagtgag gggcactcct gtgatgtggc acccctgtga   3360
ccgaggtcat gtgtgatcgg tgtaagggca ggaagcgagt cattggtctg caccaggcgt   3420
gggggcttct gcgagggcag gacccaaagt cggcctggcc tcccggctgc agcactcctt   3480
tccctttcga attaggttag agccctggga cgggaggtgc cctgtagacc acccccctca   3540
ccaacttccg tcctccgccc cacccccgcg gtgatccggt gaactgccgg ccccctgctg   3600
tgcaccgagt ggggcagtga ccctgacgtg gcgtctcctg ccgcccctgc caccgccacc   3660
acctccggtg gcccagcctc cgcattcccc acccccatgg aggaatgcac caggcctccc   3720
ttcctggatg cacccctcac ccacatgctt ccaaaccctg gcattttctg ctcccccttt   3780
actcccaccc cttcccctag gctcccagac aaaggggaag tggctggatc ctcttaaagg   3840
gacagtgtcc caccagctta ctgctgaact cccctcctca accccagttc cctagttaca   3900
gttaattagc attagcagac agcccatgag tgatacccat gcaggcccca ggctgtggag   3960
agtttcctgg gtaggaaaca gcccttaagg tccctcatct catccaggtc ccagtctttc   4020
ctacctgcct ctctcctaga ttgtggccct ttggagcctg gttcttctgt ccctgtgtga   4080
ccgacacata gcacccaaac agtggcagag cgggacggac cccctagcct gttctctgtg   4140
tgggtctgta ccctgaccca gacatgcccc cccacagcag gacccagggg ggcacatgtg   4200
tgcctgcggg ttcactgggg cacccgcatt tggtttattt tattttttag agagagggtc   4260
ttgctgtgtc acccagctgg agtgcagtgg tgtaatcata gcacactgca gccttcaact   4320
cctgggctca agcgatcctc cctccccagc ctccctagta gctgggagta caggacccac   4380
tgtatcctgg ctaatttttt aataattttt taagagatgg ggtcttactg tgttgcccag   4440
gctggcctca aacctctggc ctcaagtgat cctcccacct tcgcctcctg aagtgctgag   4500
attacaggca tgagccacca tgcccatccc agactgacat ttctatattt gttcatcctg   4560
gctgggcagg gctgctggtc cccaccccac cgggatgctt ggctgggaaa aagccgggaa   4620
tgtaggtcta accctggcct gtgttgtggc acctacagcc tggcattcct ccccatctgc   4680
ccttcaaggc cccaccaacc aggcctcctt ggtagcctct agtgaggaaa caggcgaacc   4740
gtggctttga tgaccctgca cacctgggga ttctcctcta tttttctttt tcttttttttt   4800
tttttggag acagagtctc actctgtcgc caggctggag tgcagtggca caattttggc   4860
tcactgcaac ctctgcctcc caggttcaag cgattcttct gcctcagcct cccgagtagc   4920
tgggattaca ggtgcccacc accatgcctg gctagttttt gtatttttag tggagactgg   4980
gttttgccat gttggccagg ctggtctcag actcctgacc ccaagtgatc tgcccacctc   5040
ggcctcccaa agtgctggga ttacaggtgt gagccaccgc tttgggaggc cgaggtgggc   5100
ggatcacgag gtcaagagct caagaccatc ctggccaaga tggtgaaacc ccatctctac   5160
taaaaataca aaaaattagc tgggcatggt ggtgtgtgcc tgtagtccca gctactcagg   5220
aggctgaggc aggaggatca cttgaacctg gaaggcagag gttgcagtga gccgagatcg   5280
```

-continued

```
agccactgca ctgcagcctg gcgacagagc aagactccgt ctcaaaaaac aaacaaaaag   5340

aaaacttgtt ctaattctta caaaggtgcc tgtagccgag gcaggggccc aggtgaggtg   5400

gaggagggcg ggagtggacg tctcagcccg gcccctctcc tgcaggtgtt gtgactgcag   5460

tgcctccctg tcgcaccagt actatgagaa ggatgggcag ctcttctgca agaaggacta   5520

ctgggcccgc tatggcgagt cctgccatgg gtgctctgag caaatcacca agggactggt   5580

tatggtgagc gccccctgcc ttgcacactc acctggggtg ggggtatcca agcagacccc   5640

atgctccagg tctctctccc atcattgtct ctcctggtct cctttttgct ggtctttgga   5700

gctgctttct gagcctgact gtctgtctgt atccctcagc gcccccatct atggagccag   5760

ctctgtccag gagctcagca gctggccagc cgggtccctg cagttgtttt tttggtgaca   5820

cccttggaag aggcctaggg gaggatctgt gggggttgtt gggtctgctg agctgggctg   5880

ttccctcctc acccccgcac caggtggctg gggagctgaa gtaccacccc gagtgtttca   5940

tctgcctcac gtgtgggacc tttatcggtg acggggacac ctacacgctg gtggagcact   6000

ccaagctgta ctggtgagtg ccttggcccc tccctgagcc taggaggccc acctgtgtca   6060

cagatctgca agggtgctga ctctcccaca cccgggcctc ctgccctttc ccatggggtg   6120

aggtttgttg gggcaaatgt tcatatctcc tttcccatcc cggcatggaa acaagtgaga   6180

aataacacac agaagtcagt gtgaaaaagc ctcagacggc caggcatgct ggctcacgcc   6240

tgtaaaccca gcactttggg attccgaggt gggtggatcc cttgaggcta ggagttcaag   6300

accagcctgg ccaacatggt ggaaccccat ctctattaaa aatacaaaaa ttaaccaggt   6360

gtggtggcgg gtgcctgtaa tcccagctac tcaggaggct gaggcaggag actctcttga   6420

acctgggagg tggaagttgc agtgagccaa gattgcacca ctgccctcca gcctaggcaa   6480

cagagcaaga ctctgtctca aaacagaaaa cctcagacgt cagctttctt actggccatg   6540

actgcagcat ggtgctggca caaaccacca gaggtggggt ggatgccaca agttaaggac   6600

accatcccca gcataactgc tccctcttta gacaccagcc acaagttcag ggtccccaa    6660

cccactcaca cttctgaccg actggctaca aattcaggga ctcccaagac cctgccaagt   6720

ttgatcgttt gctaacagac tcacagaact caggaaatcc tccattttta tcccagtttt   6780

attatgaagg acacagctca ggtccgacca aatgaagaag catctcccct ccctccccta   6840

gcacatcaat gtgatcacca accaggaagc ttcactgagc ttcagcagcc agagttttta   6900

ttgggatttc attacatcgt catgactgat tgagtcattg gccgtatgat caagcttagt   6960

ctctagcccc cgttcttgga ggtcaggctg gatgaaagct gcaaccctct tcaaatcaca   7020

tgatgtatct ttgcggggct gagtcatctc attagtatca actcaggaat agtctgaggg   7080

gctcatgaat aacaaagata ccccattcca aggacttaga gtctccctcc caggaatcag   7140

gacaaaaccc agacagattc tttcttatac aacactgatc aagctggatt agaggacaac   7200

gtggcttgat cccagatggg cttttaatga cttcctcctg aactggattt atcctcaggc   7260

cttgtcctgg ccgccttaca ggatcacagc gagtagacag acccgaatga ctcagaggga   7320

cgagggctgg ctgggcacgc acagttcctg ctcccagttc cataggaaga gtgaaagaaa   7380

agaaagctgg ccaggtgcag tggctcaccc ctataatccc agcactttgg gaggccaagg   7440

caggcagatc acctgaggtc tggagtttga ggccagcctg gccaacatgg tgaaaccgtc   7500

tctactaaaa ataagaaatt agccaggcat ggtggtgcgt gcccgtaatc ccagctactc   7560

aggaggctga ggcaggagaa tcgcttgaac ccaggaggcg gaggttacag tgagccaaga   7620
```

-continued

```
tcacaccact gcacttttgg acaattgcta gctttccttt tcttttgaga cagagtcttg   7680
ctttgtcacc caggctgggg tgcagtgttg taatcaacag agtgagactc catctcaaaa   7740
aaaaaaaaaa aaaggaaggg attgggggaa gagcctgggg ctgggggctg cagagatgct   7800
gaaattgatg acgcccttga cactcttttc ttcccacccc ggcggctctt gcagcgggca   7860
ctgctactac cagactgtgg tgacccccgt catcgagcag atcctgcctg actcccctgg   7920
ctcccacctg ccccacaccg tcaccctggt gtccatccca gcctcatctc atggcaagcg   7980
tggactttca gtctccattg accccccgca cggcccaccg ggctgtggca ccgagcactc   8040
acacaccgtc cgcgtccagg ggtgagtggc cggcctgccg aggctgccgt cggtgtggct   8100
atggctgttg atgtgggtgg cagagtctgg cactgggggc cctgaaaatg aatgggcgag   8160
tgtttgggta cagatggggc ccagttctga caacctggtt tgccagattt ctggcccagt   8220
cattcctctg aataccatta caaatgccag atacaataaa aagacatttt caaccgggca   8280
tggtggccca cacctgtaat ctcagcactt cgggaggccg aagtgggtgg atcacctgag   8340
gtcaggagtt cgagaccagc ctgggcaatg tggtgaaacc ccgtctctac taaaaataca   8400
aacgtagcca ggcatggtag tgtgtgccta tagtgccagc tgcttgggag gctgaggcag   8460
gagaatcact tgaacccagg aggtggaggt ttcagtgagc cccgactgcc attgcactcc   8520
aggctgggca acaagagtgt aactctgtat caaaaaaata aaaataaaaa aaacacactc   8580
aaaaaataaa aagacatttt ctttagtcca tgtctgatcc aacaagaaag aggaggaacc   8640
aagtcaagaa tgagtgaaga agctgggcgc agtaactcac acctgtaatc tcagcacttt   8700
gggaggccaa agtgagagga tcacttaagg ccagaagttt gagaccagct tgggcaacat   8760
agcgagacct gcatgtctac aaaaaaaaaa aaaaaattaa aaattagcca ggcatggtga   8820
aatcactgaa cacataaagg ctgggcatgg ttgctcacac ttataatcga aacactttgg   8880
gaggctgaga tgggaggatc acttgaggcc aggagttcga aaccagcctg ggaaacattg   8940
tagtcacagc tacttgggag gctgaggcag aaggatctct tgagcccagg aagtggctac   9000
agtgagctat aattgcacga ctgcactcta ggctgggcaa tggagcaaaa ccctgtctca   9060
aaaaaatggg gcagggctga taaagattag attactgtgt gactttgagc agctgctttc   9120
tctctaggct ttgggggtct gtttgaacaa tgagggagtt ggataccttg gagctttcta   9180
agatttctgt ggcgccttta ttgacacctt gagaagtagc atgcagtgtt tctacttttg   9240
ggcaattggt cacttctttt tttttgagac agtctcactc tgtcgcccag tctggggtgc   9300
agtggtgtga taccagctca ctgcaacctc cacccacaag gttcaagcaa ttcttgcacc   9360
tcagcccccct gagtagctgg gactacaggt gaccacatgt ggctaatttt tgtattttta   9420
gtaaagacag ggtttcacca tgttggccag gctcgtttca aactcctggg ctcaagtgat   9480
cctcccttct cggcctccca aagtgccggg attacaggtg tgagccaccg tgcccggccc   9540
aagtgctagc tttctctctc tctttttttt tttttcgaga cggagtctcg ctctgtcgcc   9600
caggctggag tgcagtggtg tggtctcggc tcactgcaag ccccgcctcc tgggttcacg   9660
ccattctcct gcctcagcct cccgagtagc tgggactaca ggcacctgcc accatgcccg   9720
gctaattttt tttttatatt tagtagagac agggtttcac catattaggc aggatggtct   9780
cgatctcctg acctcgtgat ccgcccgtct cggcctccca aagtgctgcg attacaggca   9840
tgagccacca cgcccggccc taccaagtgc tagctttcat ttgacgcagt gaatgtttct   9900
tgtacacctg gcaggtgcct ggcactgcat aggcactgtt gagatgtgaa ggtggccctg   9960
gggacagaaa attatactgg gcttgactgt gtgtctccat cccttgacat cagccaagcc  10020
```

-continued

```
agcagctgct ttacatacat gatgagcaga cagctgcttg aaagagatga ggaaactccc  10080
agaccaacgg ctcttaccag agggccaagg gaggtcccca cagagtcaga ggctgcagct  10140
ggtccctgaa atccaggcag aattttagaa atgaagacag tcagctgggt gcagcggctc  10200
atgcctgtta tctcagccac ttcggagggc tgaggtgaga ggattgcttg agcccaggag  10260
gtggaggctg cagcaagcta tgatgacacc atgcattcca gcttgggcga cagagcgaga  10320
ccctatctct aaaataaaaa tgaagaagac agttaatgac gtctcctccc tgtctgcctc  10380
actgggtaag cattcgccca gccaacatct ggaacatccc agttctgcaa agagccacac  10440
ccttcccaga aagagcccaa cttgccaaag atttacttat ttgttttaaa ctggttttag  10500
ttgaccgctt ttcattttgt gtatagcagc gttttaagga aggtctaatt tatccaggcc  10560
acctgctgct ttagcaaacc aagggagagg atgtgagatt ctaaggaatt tacatatgta  10620
tgtcatatat atatatatat atatagacac acaatttttt tttgagacag ggtcttgctc  10680
tgtcatacag gctggagtgc agtggcacaa tcatagctca ctatagcctc agatgcctgt  10740
gctcaagcaa tccactcacc tcggcctcct gagtagtgag actacaggca cacaccacca  10800
cacccagcta attttttaat tttttgtaga gactgagtct tgctgtgtcg cccaggctag  10860
tcttgaactc ctgggctcaa gcaatcctcc cacattggct tcccaaagtg ctaggattac  10920
aagcgtgagc cactatgcct ggcttatttt taaggttata tgcatgcaaa gcctgtatca  10980
atgaaaatat tttctttggt ttttttcaac ttttcatctt cgcattttgc agatttatag  11040
aaaatttgct aaaataataa gtccattgaa tacatacaca cccttcacca aggttcacca  11100
attcgtaact gccatatttg ggagttatat gtgtgtctct ctatatatac atatatggat  11160
acagatacat atacatgttt agtgacttgt ttatatttgt acatacatgt acatgttgtt  11220
atttattgat cgtttgggag taagttgcag ggatcattga ctccccccaca attatgctag  11280
atattctcaa aagaaggacc ttctcttttt tttttttttt tttttttggg agacagggta  11340
tcactgtcat tgaggctgga gtgcagtgat gcgatcacag ctcactgcag cctcaacctc  11400
ccaggctcaa gtgatcctcc cacctctgcc tcccaagtag ctgggactac aggcacgggc  11460
caccacgcct ggctaggcat tctgttatgt aattatcaat tgtatcttat agttcagtga  11520
tcacattttg gaaatgtaac attgatacca ttatctaata cacagaccat attcaaattt  11580
tgcctattgt ctctatactg aactactgag ctgtccttta tagcaatctc cccctcatcc  11640
acagtccagt ccatgatcaa cattgcattt aatcgtcatg tgtcatcagt atcttttttt  11700
tttttttttt tgagacggaa ttttgctctt gttgcccagg ttggagcgca atggcgcaat  11760
cttggcttat tgcaacctcc gcctttgggc ttaagtgatt ctcctgcctc agcctcctaa  11820
gtagctgaga ttacaggcgt gcaccattat gcatgcctaa tttttgtatt tttattagag  11880
acggggtttt accatgttgc cctggctggt cttgaactcc tgacctcaaa tgatccaccc  11940
acctcagcct cccaaaatgc tgggtttaca ggcatgagcc actgcgtctg gccatttcct  12000
cagcctttca ttgcccttca tgatcttgac atttttgaag tgtacaggcc agtcattaaa  12060
gtaaaatgtt tttccttttt tttttttttt tttttaaaaa gagacagggt ctcactgtgt  12120
tgcccaggct ggtctcagac tcctaggctc aagtgatcct cccgcctcag cttcccaaag  12180
tgctgggatt acaggcgtga gccatcgtac ctgccctcgc atttgggttt gactgatgtt  12240
tcctcttagg gagacaggct ctgcaggttt ggcctgatac tgcataagtg atcctctgtc  12300
cttccgagtg gatcttgcca ggagacatat gatgtcagtg tgccctttgc tgaggatgtt  12360
```

-continued

```
cactttgatt acttgttttt tctgtactgt aaggattttt ttccctttgt catcaataaa  12420
ccatttgtga gatttgagtc tgtaaatatc ctgttcccaa aaacccttcc ccaaatgatt  12480
tgagcatcta ttgatgattc ttgcctgtag cgattattac tagggtggct accaaatgct  12540
gaatttctaa ctctgttctt ccttctgcat ttgttactgt aaggaagagc ttctccccca  12600
tacgagaata gtctttttgt ttgcttggtt gtttttttga gatagggtct cactctgttg  12660
cccaggctgg agtgcagtga catgatcata gctcactgca gcctcgacct catgggctca  12720
agcgatcctc ctgcctcagc ctctcgagta gctgggacta caggcagcac caccatgcct  12780
ggctaatttt ttattttttg taatggtgag gtctcactat tttgctcagg ctggtctcga  12840
actcctgacc tcaagtgatc ttcccacctc agcctcccaa atagctggga ttacaggagt  12900
gtgccaccat gctcagctaa ttttctgtaa aaaatgtcat agagatgggg tcttgctatg  12960
ctgcccaggc tggtctcaaa cccctagtct caagcaatcc tcccaccttg gcctcccaaa  13020
gtgctgggat tccaggcatg agccaccaca cctggccctg tttttcttaa agttctcagt  13080
ctcctctctg ccttacccc atccccttt ccatctccag gacctagggc agagacaaag  13140
tgagcattcc ctaaaaagct tttatgaggc aaaatgaaaa ccagctcacg cctataatcc  13200
cagcactttg ggaggccaag gtgggtggat tacctgaggt caggagttca agaccagcct  13260
gaccaacata gagaaacccc atctgtacta aaaatacaaa attagccagg catggtggca  13320
catgcctgta atcccagcta ctcaggagcc tgaggcaaga gaatcacttg aacctgggag  13380
gcggaagttg caatgagccg agatcactcc attgcactcc agcctgggca acaagagcaa  13440
aactctgtct caaaaaaaaa aaagaaaaga aaagaaaacc aggtccctaa caccgaagag  13500
ttaaaagaaa taagtaaatt tggcaaattg gtctttttgt gagttagctt ataggcaact  13560
gatcgagggt ctctttcccg tcttcaccct gcaattgtgg ctcagggcaa gctgccagct  13620
ccctcctgcc aatgcaggag caatagagct tggcctcctc ttgcagggcg agtttgggag  13680
tcagatatga agccactaat ccgggacctt tttgggaccc aaggcactca tctgccccaa  13740
gcataccagg caggccaggt gcaatgactc atgtctgtaa tcctagcact ttgtttttgc  13800
gacggagtct cgctctgtcc acccaggctg gagtgcagtg gcagaatctt gactcactgc  13860
aacctccacc tcccaggttc aagcaattcc tgcctcagcc tcccaagtag ctaggactac  13920
aggcgcccac tgccacgctc ggctaatttt tgtattttca gtagagacgg cgtttcacca  13980
tgttggccag gctggtctca aactcctgac ttcaagtaat ccatccacct tggcctcccc  14040
aactgttggg attacaggtg tgagccactg cgcccggcca gtcctagccc tttgggaggc  14100
taaggcgggc ggattgcatg agctcaggag ttcgagacca gcctgggaaa tgtggtgtaa  14160
ccccgtctct actaaaaata caaaaaaaat tagctgggtg tggtggtgtg cacctgtaat  14220
cccagctact caggaggctg aggtacgaga atcgcttgaa ctcaggaggc agaggctgca  14280
gtgagctgag attgtgccat tgcactccag cctgggtaac agagtgagat tctgtctcca  14340
aaaaaaaaaa aaaaaaaaat tcgagaccaa acatacctgg gatttggaag gatagatctg  14400
ttcccccagg gtggagacaa tggtccattg aatgggaaca gctgagcatc ttgtgtgggt  14460
ggccagtgcc tacaagcgtg ccacctttct ccagctcaca cctgtggcag acatcagtaa  14520
ttgattacag aattcctccc ctgaaaccag aactcggtgt tctggccatc tgctacttcc  14580
cagtcacacg aagtagaatc ctccacctgc tcaccctgga tctggtgccc ttcgccttgg  14640
tttcctgttg ggctctgag ggacaggtgg gcactggcct gacccctgcc ttacccacag  14700
agtggatccg ggctgcatga gcccagatgt gaagaattcc atccacgtcg gagaccggat  14760
```

-continued

```
cttggaaatc aatggcacgc ccatccgaaa tgtgcccctg gacgaggtac ggtcctgagt  14820
ctgtggggca ggacgggagg tagtgccttc atgcctagcc ccctccccac tccaccccca  14880
ttcacatgcc tgctgtcccc agattgacct gctgattcag gaaaccagcc gcctgctcca  14940
gctgaccctc gagcatgacc ctcacgatac actgggccac gggctggggc ctgagaccag  15000
ccccctgagc tctccggctt atactcccag cggggaggcg ggcagctctg cccggcagaa  15060
acctgtcttg taagtcagcc tgctcctcgg ttcagctggg tgctttcact cctgctgggg  15120
ctcaggggct gtgggaccta ggtcggggag ccagccctgc acaaatgcag cccaggcttg  15180
agccagggag gtggaggctg cagtaagctg tcatcacacc actgctctcc agcttgggtg  15240
acaaaacaag acccactctc aaaaaaaaag aggaaacaca catttttttaa aaagccgggg  15300
acggggccag gcgtggtggc tcatgcctgt aatcccagca ctttgggagg ccgaggcagg  15360
tggatcacct gaggtcagga gttcaagacc agcctggcca acatgggaaa cctcatcttt  15420
actgaaaata caaaaattag ccgggcttgg tggcaggtgc ctgtagtccc agctactcag  15480
gaggctgagg cagatgaatc acttgaaccc aggagatgga ggttgcagtg agccaaggtc  15540
acgccactat actccagcct gggcaacagt gtgagactct gtctcaaaaa aaaagaggat  15600
gacagagcag gatctgaggg gttgagggga gctgggggct gccactagag ccaggatagg  15660
ccgagacact gggatgggca gcctttggac tgtcccaggc gggccctccc aaagcagggg  15720
gtgattgcat agactggcat ggacaggggc atgcaggcag gaggaggaag gggcagggcc  15780
ttggccgggt gctacctgtc ccccggtggc acttggcacc atgtgtgccc cccaggagga  15840
gctgcagcat cgacaggtct ccgggcgctg gctcactggg ctccccggcc tcccagcgca  15900
aggacctggg tcgctctgag tccctccgcg tagtctgccg gccacaccgc atcttccggc  15960
cgtcggacct catccacggg gaggtgctgg gcaagggctg cttcggccag gctatcaagg  16020
tacagagcat gccagggtct caggggacag tctgggtggg acccctccat cctccttcct  16080
tcccagtcta tggaaacaca gtggaagggg tatctggctt ccagactccc tggccagtgc  16140
cctctcctcc cttggcctcc tggagctaat taggaacagg ggacctccta caggtagact  16200
gagaccttat gtgcgggagg tcattgaaag gtggctccta gccaggcaca gtagtttatc  16260
cctgtaatcc cagcaccatg agaggctaag gctgtaggat cgcttgagcc caggaattca  16320
agaccagcct tgacatcatc tctacaaaaa atttaaaaat taattgggta tagtggtgca  16380
tgcctgtggt cccagctact tgggaggctt aggcaggagg attgtgagcc aggagttcaa  16440
ggctgcagtg agctatgatc atgccacagc actccagcct gggcaataga gcaagacccc  16500
atctcaaaaa aaaaaaaaaa aagacaaggg attaatacat cccatccact tgggtatttg  16560
ggaacatccc atgcacagcc tagagtatga agccatctgc acatctccct ggcagtcctg  16620
gggtggagat ggggcttcct agaaggcggg cttacagcag agcttctgtc ttcacacctc  16680
tgtgtcccac acgcaggtga cacaccgtga gacaggtgag gtgatggtga tgaaggagct  16740
gatccggttc gacgaggaga cccagaggac gttcctcaag gaggtcagtg agcggaatgc  16800
cctcttccct ccagagggac ttccaggtgc tcacccctgc cccatcaaca caggtcggaa  16860
aagggctctg ggaaccattg aaagaagagc gagcaggcca ggcatagtgg ctcacgcctg  16920
taatcccaac actttgggag gttaaggaga gaggatactt tgagaccaac ctgggcaaca  16980
tagcaagacc ccgtctctac aaaaaaattt taaattaacc gagcttggca atgtgcacct  17040
gtcatcccag ctactcgggg ggctgaggtg ggaggctcgc ttgagcccag gagttggagg  17100
```

-continued

```
ctgcaatgag ccatgatcgc accactgcac tccagcctgg ggaacaaggc aagaccctgt  17160
gtccaaaaaa aataaaagta actgcattgg tcgggcatag tggctcacgc ctgtaatccc  17220
agcactttgg gaggctgagc cgggcggatc acctgaggtc aggagttcga gactaccctg  17280
gccaacatgg caaaaccccg tctctactaa aaatacaaaa attagcccag catgatggtg  17340
gtgagtgcct gtcatccagg ctactcagga ggctgaggca ggagaatttc ttgaactcag  17400
gaggcggagg ttgcagtgag ccaagatcgt gccgctgccc tccagcctgg gcgacagagt  17460
gagactcctt ctcaaaaaaa aaaaaaagaa aagaaaaaag aaagtaactg caggcagggg  17520
actgggaaaa agagcatcgc tgggggtggg ggcagctcaa gcagagggca caggacgcca  17580
gagggtgtgg cagaggcagg agaggggagc tgggggttcc gtatctttga gaccgcctac  17640
agcccctggt gggatggaaa agggagaagc agacccaagc acagctggga ccacacagag  17700
cccgggccca gcctgtttgt gccccgccag gtgaaggtca tgcgatgcct ggaacacccc  17760
aacgtgctca agttcatcgg ggtgctctac aaggacaaga ggctcaactt catcactgag  17820
tacatcaagg gcggcacgct ccggggcatc atcaagagca tggtgagtcc tgggcagagc  17880
cagccacccc cgctgtgcgg ccccgggcaa agcagctccc tctgtgagcc tcagtctcat  17940
ctcttcaatg gggggaagcc acaggggtct caaaggccct ctgaaccctg attcctaatc  18000
aaaaagggga gcgactgact ccatctaaag ctaggaaagg ccaggtacaa tggtgcacac  18060
ctgttattct ggcactttgg gagcccaagg caagaggatc actcgaggcc aggaattcaa  18120
ggctgcagtg agctgtgatc tcaccactgc actccagcct ggaccacaca gcaagaccct  18180
atctcaaaaa ctaaaataaa attcagagct ttccttaagg atttgaataa aattacaaat  18240
ccatctttag aaataaagtg ctcaggccag gtgcagtggc tcatgcctat aatctcagca  18300
ctttcagagg ctgaggccag cagatcacct gaggtcagga gtccaagacc agcctggcca  18360
acatggtgaa accccgtctc tactaaaaat acaaaaatta gctgggcctg gtggcaggca  18420
cctgtaatcc cagcactttg ggagactgag gttggcagat cacctgaggt caggagttcg  18480
agaccatcct ggtaacccgt ctctactaaa aatacaaaaa attagccggg caaggtggca  18540
ggtgcctgta gtcccagcta ctcgggagac tgaagcagga gaatggcgtt gaacccaggg  18600
ggcagagcct gcagtgagcc aagatcgcac cactgcgctc tagcctgggt gacagcgaga  18660
ttccgtctca aaaaaaaagc acttggagga agcctcacag agtcctgtgc tggaccacac  18720
cctggggatc cagtcctggc ctccagcccc atttctgtac caccctgaga ccatgggatc  18780
ttcctcaggt tggattacct tgtatccaag gtgtggaccc tatgggctcc tgctaggtgt  18840
aacttgacac aacgggttcc gttgtcaggt gcaatttaga aactctgggc taggccaagc  18900
gcagtggctc acacctgaat tcccaaactt tggaaggccg aggcaggagg gtcactagag  18960
gtcaggaggt caagaccagc ttggacaaca taatgagatc ccaatcccat ctctacaaaa  19020
aaaattaaaa aattagccaa atgtggtgac acatgcctgt ggttccagct ccacaggagg  19080
ctgaggcaga aggatcactt gagcacagga ggtcgaggct gcactccagc ctgggtgata  19140
gagtgagacc ctgtctcaat aaaaaataaa gatctccaag gggatgaggt ttgagaatga  19200
ggcgtctccc ccaaatgatt tgagcccaaa gccccgttct cctggcatgg ctcagtgctg  19260
ccactgcgca ggtgaccttg ctgggccctt ctacctctta cctgtctgtg aaagtaggtt  19320
ctaatttttt aaaaacctag aaagatgagt tttttgtttt tgtttttgtt tttcccgaga  19380
tggagttttg ctcttactgt ccagcctgaa gtgcaatggc gtgatctcgg ctcactgcaa  19440
cctccacctc ccaggttcaa tcgattctgc ctcagcctcc cgagtagctg ggattacagg  19500
```

-continued

```
agcccaccac cacacccggc taatttttgc gtttttagta gagacagggt ttcaccatgt  19560
tggtcaggct ggtctcaaac tcctgacctc gtgatccaac cactctgacc tcccaaagtg  19620
ttgggattac aggcgtgagc caccacacct gacagaaaga tgagatttta tagaaaataa  19680
atatagcttg ttttctcaga ggaggcagat tgggagctat agaggaatat ccctgcttag  19740
agtttgaaat cagttctgtt aggaaataat gtttgtaggg gccgggtgcg gtggctcacg  19800
cctgtaatgc cagcactttg ggaggctgag gcaggtggat cacttgaggt taggagtttg  19860
agaacagcct ggccaacatg gtgaaaccct gtctctacta aaactacaaa aattagctgg  19920
gtttggtggt ggacacctgt aatcccagct acttgggagg ctgaggcgag agaattgctt  19980
gaggccgggt gcagtggctc atgcctgtaa tcccaacact gggaggccaa ggtgggcaga  20040
tcacctgagg taaggagttc aagaccagcc tgaccaacat ggtgaaaccc cgtctctact  20100
aaaaatacaa aaaattagct gggtgtggtg gcgcatgccc atagtcccag ctactcagga  20160
ggctgagaca caagaatcac ttgagccccg gaggcgaagg ttgtagggag ctgagatggt  20220
accactgcac tccaccctgg gtgacagagt gagactccat ctaaagaaaa aaaaaaaagg  20280
aaataatgtc tgtgagctgt gttgactcat actccttaga agcagacagt tgtgggtgcc  20340
cgaagaaatc ggggtgttgg ggagcccagg gaccctctag gacgcttgcc tcttcctgcc  20400
tctgtctcat gcaaccatcc ctgccatcgg ggcccccacc ggccccaccc tggccattct  20460
ttctccatcc caggacagcc agtacccatg gagccagaga gtgagctttg ccaaggacat  20520
cgcatcaggg atggtgagtg agccgggtgc tctagctcca ttcataatcc caccaggaat  20580
ttgcaaacag aacccacaaa gaagctttga aagagggcag agggggtcga tgggagagtg  20640
ggaagaatcg tcccgactgg cctgattggg gtgggagcag agggagttcc tggggagcca  20700
ggatgggctg gggtccctct gcacagctgc cccctgactc ccgtgtcccc gtccctaggc  20760
ctacctccac tccatgaaca tcatccaccg agacctcaac tcccacaact gcctggtccg  20820
cgaggtgagt accagggccc cacgtggctg ggtgtcagga gacagcagga gcccatccaa  20880
ccccagcctc agggccttcc cagaactgga ggcccctcca tgttgcctcc atgacttcaa  20940
tttgaggtgg gggtgggggg cagcagcccg tggggaagag cgcagggtca ggaggcagac  21000
agacctgggt ttgagtcctg tctctgccac tgactcatgg tggaccatca gagtcccagg  21060
ctggtaggag ggtctcataa atcaatgaag gagaaagtga catgtaagct acaaaggacc  21120
aggaccgtgg tcttcataga gcacagccca tggcagagtg gccatgggct acaccagaca  21180
gcaccagcat ctgggggcca cagagtgggg gcataggcgt atgggctgga gtggtcaggg  21240
caggcttcct gaaagaggag gcttggccag acacagtggc tcacacctgt aatcccagca  21300
ctttgggagg ccgaggcagg cggatcacga ggtcaggaga tcgagaccgt cctggctaac  21360
atgggcactg tggctcacac ctacaatccc aacactttgg gaggccgagg tgggtggatc  21420
acttgaagcc aggagttcaa gaccagcctg gccaacatgg ctaacacggt gaaaccccat  21480
ctctactaaa aatataaaaa attagccggg cgtggtggca ggtgcctgta gtcccaacta  21540
cttgggaggc tgaagcagga gaatggtgtg aacccgggag gcggaacttg cagtgagcca  21600
agatcgcgcc accgcactcc agcctgggtg acagagcgag actccatctc aaaaaaaaaa  21660
agaggaggct ttaggtggat atttaagcag gggacgggca ggcaaagagc ccagtgtcta  21720
aggattgtca agggaggaga gcccggttct ccaccaaaag cacaggagcg agtaaccatg  21780
cccatctgga gaggtggtgt attcgtgtcc tggggctgcc atcatgaagt actgtgaacc  21840
```

-continued

```
agatggctca aaacaacaga aatgtgctgg gcacagtggc tcacacctaa aatcccagca  21900
atttgggagg ccaaggcagg tggattgctt gagctcagga gtttgagacc agcctgggca  21960
acattacgaa agcccatctc tgccaaaaat acaaaacgga atagccagcc gtggtggcat  22020
aagcctatgg tcccaactac ctgggaggct gaggtgggag gatcacttga gcctgggagg  22080
tagaggttgc agtgagccaa gattgtgcta ctctactcca gcctgggaga cagagccaga  22140
ccctgtctca aaaaaacaaa acaaaacaag gccaggcact gtggctcacg cctgtaatcc  22200
cagcactttg ggaggccgaa gtgggtggat cacttgaagc caggagttca agaccagcct  22260
ggccaacatg gcaaaaccct gtttctacta aaaattcaaa aattagcagg catggtggcg  22320
catgcctgta atcccagcta ctcgggaggc tgaggcagga gaattgcttg aacccaggag  22380
gcagaggttg tagtgagctg agattatgcc actgcactcc agcctgggtg atagagtcag  22440
acaccgtctc aaaaaaaaaa aagcatcaca tggcaagagg ggctgacaag agacccccaa  22500
actgaccatt atacagaccc actcttgtga taactaacct ggtccctcaa taacccatta  22560
atctgttaat tcatacagag ccctcatgac ccaatcacct cttacaggcc ctgcctctta  22620
ataccgttag agtcaggcca ggcatggtga catgggcctg tagtcccagc tagttggaag  22680
gctaggtggg aggatccctt gagtccagga ggtaaatgtt acagtgagct ctgattgtgt  22740
cactgcactc cagcctgggc aacagagcga gcccctgttt ttaaaacagc aacaagccag  22800
gcacagtggc tcacgcctgt aatcccaaca ctttgggaga ctgaggcagg cagatcactt  22860
gaggtcagga gttcaagacc agcctcacca acacagtgag acccctctct actaaaaata  22920
caaaaattag ctgggcgtgg tggtgggtgc ctgtagtctc agctactcat gagactgagg  22980
cagaattgct tgaacccggg aggtggaggt tgctgtgagc cgagatcacg tcactgcact  23040
ccagcaacag agtgggactc catctcaaaa aaaataaaaa ataacagaga tctgtgttgg  23100
cttacacctg taatcccagc actttgggag tccaaggtgg gcagattgct tgagcccagg  23160
agtttgagac cagccaggca acatggcaaa aaaataaaaa aatttgtctc tacaaaaaaa  23220
ttaaaaaatt agctggcatg gtggtgagta tctatagtac cagctactca ggaggtggag  23280
gtgggaggat cgcttgagcc tgggaagttg aggctgcaat gagctgtgtt cgtgccactg  23340
cactccagcc tgggccacgg gagggagact ctgcctcaaa aaaaaaaaaa aaaaatcaaa  23400
cccgaaaagc aaaaaacata gacctcacct gcttattggg aatattcaag ataaaattag  23460
gccaggcacg gtggctcacg cctgtaatcc cagcactttg ggaggccgac gtgggcggat  23520
cacgaggtca ggagatcgag accatcctgg ctaacacggt gaaaccccgt ctctactaaa  23580
aatacaaaaa attagctggg catggtggca ggcgcctgta gtcccagcta cttgggaggc  23640
tgaggcagga gaatggcgtg aacctgggag gcagagcttg cagtgagctg agatcgtgcc  23700
actgcacttc aacctgggca atagagcaag actccaactc aaaaaaaaaa aaaaaaagat  23760
aaaattgggc caggtatggt ggcttactcc tgtaatccca gcactttgaa aggctgaggc  23820
aggtggacca cttgaggcca gaagttgaag accagtctgg gcaacatagc aagaccctat  23880
ctcaatcagt caatcaacct aaataaatag taaatctggt ggcatgccaa gcacaggacc  23940
tgggtctata atcaaaattc ctgtcttgat gggcacagtg gctcacacct gtaatcccag  24000
cactttggta ggccacagtg ggtggatcac ctgagatcag gagttcgaaa cctgcctagc  24060
caagtatggt gaaacccgtc tttactaaaa atacaaaaat tagccaggca tggtggcagg  24120
cgcctgtaat cccagctact cgggagggtg aggcaggaga atcgcttgaa cctgggaggc  24180
ggaggttgca gtgagccgag atcatgccac tgcgctccag cctgggtgac agagcaagac  24240
```

-continued

```
tccgtctgaa aaaaaaaaca aaagaattcc tgtcttctct ccgaaacaaa gcagcatcag  24300
tgcccccgca ggtgggaggg agcgcttgca ggagggagca gtgggtccgc cacgacggtc  24360
tggggagcag gtggggaggg ggcagagggt gcagcgtgtg gtgggaggga ggaagccaca  24420
ctgctatctt caggtgcttc ccgcagctcc atttgcaaag agcggatggg tttggggaag  24480
gaaggggtcc ccaccctgtg ccaatacagc gtatcagagg tatgttctct gggctgtcta  24540
cgggttggct tggggtcctg gggaggggca ggccaagcgg gcagtactag gatcgggtcc  24600
cagcatgacc cggcttcacc ttcccagaac aagaatgtgg tggtggctga cttcgggctg  24660
gcgcgtctca tggtggacga gaagactcag cctgagggcc tgcggagcct caagaagcca  24720
gaccgcaaga agcgctacac cgtggtgggc aacccctact ggatggcacc tgagatgatc  24780
aacggtgagt ggttcagccc tgcccatcat ggccctcacg ggaagccatg gggggagccca  24840
ggagagctgt aacctcccaa gcccctggcc cctcccagcc tccttggctc ttcagttacc  24900
ctgtgggtcc tgttgctcct ataacacact tagtggcagc caggcacggt ggctcacgcc  24960
tgtaatccca gcactttggg aggctgaggt gagtggatca cctgaggtca gtagttggag  25020
accagcctag ccaacatggt gaaacccccca ttctttacta aaaatacaaa aattagctgg  25080
gcatggtggc gggtgcctgt aatcccagct actagggaag ctgaggcagg agaatcgctt  25140
gaacctggga ggcagaggtt gcagtgagcc gagatcgcgc cattgcactc cagcctgggt  25200
gacgagcgaa actccatctc aaaaaataaa taaatagaag acacttagtg gcttaaataa  25260
atgatcatac agttctggag tctgaagtcc agcgtcagcc tcaccgggct gaaatcaagg  25320
cgccggtagg gtgagctcct tctgcaggct ccgggggcacc tgtttcctga cctttctgg  25380
ctcgtggagg cttcctcatt cctcctgttg ctgccccctc ctctgtcttc agggctggct  25440
gcaaagcatc ttctcttctc tgatctctgc atccatcccc gcatctcttt ccctggctct  25500
aaccttcctc cttttttttt tttttttaa agagggtctc gctctgttac tcaggctgga  25560
gtgcagtggt gccaccatag ctcactgcag cctcaacctt ctgggctcaa actgtcatcc  25620
caccccagcc tcctgaatag ctgggaccac aggcatgcaa caccacaccc agctaatttt  25680
tttatttttt atttttttatt tttttttgag acagagtctc gctgtgtctc ccaggctaga  25740
gtgcagtggc gtgatctcag ctcactgcaa gctccgcctc ctgggttcac gccattctcc  25800
tgcctcagcc tcccgagtag ctgggactac aggcgcccgc caacacgcct ggctaatttt  25860
ttgtattttt agtagaaacg gggtttcacc gtgttagcca agatggtgtc gatctcctga  25920
cctcgtgatc cgcccgtctc ggcctcccaa agtgctggga ttacaggcgt gagccaccgc  25980
gcctggccaa ttttttaaat ttttaataga gacgggggta tcactatgtt gcccaggctg  26040
gtctcaaact cctggcttca ggcgatcctc ctgccttgac ctttcaaagt gctgggattc  26100
caggcatgag ccaccatggc cctccatcct tctgataggg acccttacgg tgacattggg  26160
cccacctgga taatccaaaa gcagccctcc atctcaagac cctcaactta atcccatctg  26220
cagagtccga tggaaggtgg gacgtataca agtcccaggg atcaggacgc agtcatcttt  26280
ggggatcata gttctgcctc ccacagggtc tgcttccctc agtccatttc tttgctgtca  26340
atggtcctat atatgcccag attataggtt ataaagtcct tctacaagca ggtgacacat  26400
gaacacaggt tcagggcagg cagaccccag ccatcacctc atcatagtta acctagttaa  26460
attagcctgg catgtggcgt ggtgcctaat gcctgtggtc ccagctactc aggaagccaa  26520
agcgggagat ttacttgagc caaggagatc aaggctgcag tgagctatga tcataccact  26580
```

-continued

```
gccttctagc ctgggcaacg gagtgagacc ctgtctcaag aaaacaaaaa ataggccagg  26640
cacagtggct cacacctgta attccagcac tttgggaggc tgaagcaggc ggattgcttg  26700
aggccaggag ttcgagacca gcctggccaa catggtgaaa cgctgtctct actgaaaata  26760
caaaaattac ccgggtgtgg tggcacagct actagggagg ctgaggcagg agaatcactt  26820
gaacccagga gcagaggtta cattgggcca agattgcacc actgcactcc agcctgggca  26880
acagaggaag actgtgtctc aaaaagaaaa aaaaaaaaac cttcctgtaa tcccagcact  26940
ttgggaggct gaggtgggcg gatcacgagg tcaagagatt gagaccatcc tggtcaacat  27000
gatgaaaccc catctctact aaaaatacaa aaaaattagc tgggcgtggt tgcacgcgtc  27060
tgtagtccca gctacccggg aggctggggc aggagaatga tgtgaaccca ggaggcggag  27120
cttgcagtga gccgagatcg caccactgta ctccagcctg acgacagagt gggactctgt  27180
gtcaaacaca cacacacaca cacacacaca cacacacaca cacacacaca cacacagagt  27240
taacatagcc cgcaaagaag actataaaac agtcttagtg gccgggcgca gtggttcacg  27300
cttgtaatcc cagcactttg ggaggccgag gcaggtggat catgaggtca ggagtttgag  27360
accagcctgg ccaacacagt gaaaccccat ctctactaaa aatacaaaaa ttagctggac  27420
atggtttcgg gcgcccgtaa tcccagctac tcaggaggct gaggcaggag agttgcttga  27480
acccaggagg cagaggcagg agagttgctt gaacccagga ggcagaggtt gcagtgggcg  27540
acagagcaag actctgtctc aaaaaacaaa aaagtcttag tgtttcctat gtttagggat  27600
tagtgtgagg attaaaggtt gtaaactcat ttccacctag ttggcattca gtaaatgaga  27660
attgacattt agtactaatt gtttcgggta ttttgttttt tgtttttttgt tttttgtttt  27720
ttctgagacc gagtcttgct ctgtcatcca ggctagaatg catggtgcga tctcggctca  27780
ctgcaagctc cgcctcccgg gttcacacca ttctcctgcc tcagcctccc acgtagctgg  27840
gactacaggc gcccgccacc acgcctggct aattttttgt atttttagta gagacggggt  27900
ttcaccatga tctcgatctc ctgacctcgt gatccacccg cctcagcctc ccaaagtgct  27960
gggattacag gtgtgagcca ccgtgcccgg ccagtttttt gtttttgaga tggagtcttg  28020
cattgtcacc caggctggag tacagtggcg tgatctcggc tcactgcaac ctccacctcc  28080
tgggttcaag tgattctcct gcctcagttt ccctagtagc tgggattaca ggcacctgcc  28140
accatgcctg gctaattttt ctatttttag tagagatggg gtttcaccat gttggccagg  28200
ctgatcttga actcctgacc tcaggtgatc cacccgcctc ggcctcccaa agtgctggga  28260
ttacaggtgt gaaccactgt gcccggccat gtaccgatta tttttaacat cattaagtag  28320
ctggtatcat tcccatttta caataaggaa actgaggctc agagagtctg tgtcagtttc  28380
ctgaggttgc tgtaataaat tgttagaaac ttgattattt aaaacagcag aaaatggtca  28440
ggcacagtgg ctcacacctg taatcccagc actttgggag gccgaggcgg gcagatcact  28500
ggaggtcagg agttcgagac cagcctggcc aacatggtga aacaccatct ctactaaaag  28560
tacaaaaatt agctgggcat ggtggcaggc gcctgtaatc ccagctactc gggaaattga  28620
ggcaggagaa tcgcttgaac ccaggaggca gaggttgcag tgagccacaa tcgtaccact  28680
gcactcttgc ctggacaaca aagcaagact ccatctcaag ataaaataaa cagcagaaat  28740
ttattccctc ttagttttgg aagccagaag gttgaaatcc aacagggctg cgctccctcc  28800
agggcgatct aggggagaat gcattccttg cctcttccac cttctggttg ttttgcattc  28860
ctgggcttgt ggccgcatca ctccagtctc cacccctgtc ttcacagggc cacctcctcc  28920
tcttctgctg tgtcttctct gtgtctctct caagagggca tttgcagtgg catttggggc  28980
```

-continued

```
ccacccagat catccagcat catctcatct ccagatcctt aacttaatcc catctgcaaa  29040
agaccctttt tctgacccag taacattcac agattccaga gacctgacat ggttcccttt  29100
tgggaccagc acagagttca tgacttgtgc aaagtcacgc agctgatcgg tgcctcgaac  29160
tccttgtcca gggctctgcc ccttgctcct cagagctccc aaaggcttgc tcagacctgg  29220
tggggttggg ggaaagagcc taagcctggg ttcccataga ggttgccggc atctgcctcc  29280
tgggcctgga cctcccggcc ggggcatcct cccagctggc ctggtcccct gccttttggc  29340
atccctggca cccccatgtg ttcatctgct gacagtcggt ctctttatcc aggccgcagc  29400
tatgatgaga aggtggatgt gttctccttt gggatcgtcc tgtgcgaggt aggtccaggg  29460
ttgggtagca gcggtgttga ggcctgggct cctccccact cacccaggct gcaggctcag  29520
catctgcagg ggcctcatgc caggaagcct gcccacagca aggcatgggc tggcccccat  29580
ggggtactgc agtcaggctg cagccaggcc cagtgccacc tgccctcaaa ccacctggat  29640
ggcacccaga tgcccaggct gagggccccc tggagtaact gccgggcctt gtactggaca  29700
gatcatcggg cgggtgaacg cagaccctga ctacctgccc cgcaccatgg actttggcct  29760
caacgtgcga ggattcctgg accgctactg ccccccaaac tgcccccega gcttcttccc  29820
catcaccgtg cgctgttgcg atctggaccc cgagaagagg tgagtggggt ggggccctgg  29880
cctgggagac ggtggggccg attcccggga cagccagacc caccgttccc cacccacctg  29940
tcacccaggc catcctttgt gaagctggaa cactggctgg agaccctccg catgcacctg  30000
gccggccacc tgccactggg cccacagctg gagcagctgg acagaggttt ctgggagacc  30060
taccggcgcg gcgagagcgg actgcctgcc caccctgagg tccccgactg agccagggcc  30120
actcagctgc ccctgtcccc acctctggag aatccacccc caccagattc ctccgcggga  30180
ggtggccctc agctgggaca gtggggaccc aggcttctcc tcagagccag gccctgactt  30240
gccttctccc accccgtgga ccgcttcccc tgccttctct ctgccgtggc ccagagccgg  30300
cccagctgca cacacacacc atgctctcgc cctgctgtaa cctctgtctt ggcagggctg  30360
tcccctcttg cttctccttg catgagctgg agggcctgtg tgagttacgc ccctttccac  30420
acgccgctgc cccagcaacc ctgttcacgc tccacctgtc tggtccatag ctccctggag  30480
gctgggccag gaggcagcct ccgaaccatg ccccatataa cgcttgggtg cgtgggaggg  30540
cgcacatcag ggcagaggcc aagttccagg tgtctgtgtt cccaggaacc aaatggggag  30600
tctggggccc gttttccccc caggggggtgt ctaggtagca acaggtatcg aggactctcc  30660
aaacccccaa agcagagaga gggctgatcc catggggcgg aggtccccag tggctgagca  30720
aacagcccct tctctcgctt tgggtctttt ttttgtttct ttcttaaagc cactttagtg  30780
agaagcaggt accaagcctc agggtgaagg gggtcccttg agggagcgtg gagctgcggt  30840
gccctggccg gcgatgggga ggagccggct ccggcagtga gaggataggc acagtggacc  30900
gggcaggtgt ccaccagcag ctcagcccct gcagtcatct cagagcccct tcccgggcct  30960
ctcccccaag gctccctgcc cctcctcatg cccctctgtc ctctgcgttt tttctgtgta  31020
atctattttt taagaagagt ttgtattatt ttttcatacg gctgcagcag cagctgccag  31080
gggcttggga ttttattttt gtggcgggcg ggggtgggag ggccattttg tcactttgcc  31140
tcagttgagc atctaggaag tattaaaact gtgaagcttt ctcagtgcac tttgaacctg  31200
gaaaacaatc ccaacaggcc cgtgggacca tgacttaggg aggtgggacc cacccacccc  31260
catccaggaa ccgtgacgtc caaggaacca aacccagacg cagaacaata aaataaattc  31320
```

-continued

```
cgtactcccc acccaggtcc tgcgtggcga tgtgtgtctg gggccctggg gaaatagtca  31380

aggtaagagg agttagtctt ccctgaccag aagacaagga tgagtgtggt ggctcatgcc  31440

tgtgatccca gcactctggg aggctgagac aggacgatcc cttaagccca ggagttcaag  31500

accagtctgg acaacatagt gagatcctgt ctctacaaaa attttttttt aattagttgg  31560

gcagaggcca ggtgtggtgg ctcatgcctg taatcccagc actttgggag gcagaggcgg  31620

gtggatcacc tgaagttagg agttcaagac cagtctggcc aacatggtga aaactcgtct  31680

ctactaaaaa tacaaaaatt agccgggcgt ggtggcacat gcctgtagtc ctagctactt  31740

gggagactga ggcaggagaa tcgcttgaac ccgaaaggca gaggttgcag tgagccgagg  31800

tggtgccatt ccactccagc ctgggaaaga gcgagacttt gtctccaaaa aaaaaaaaaa  31860

aaaaaattgg caggccaggc acagtggctc acacctgtaa tcccagccct ctgggaggcc  31920

gaggcaggag gatctcctga ggtcaggagt ttgagaacag cctgactgac atagtgaaac  31980

cccatctcta ctaacaatac aaaattagcc aggtgtgatg gcacatgcct gaaatcccag  32040

ctacttgggg ggttgaggca ggagaattgc ttgaacccag gaggcagagg ttgcagtgag  32100

ccgagattgc accattgcac cccagcctgg gcaacaagag cgaaactcca tctcaaaaaa  32160

aaaaaaaaaa attagttggg catggtggca tgcacctata gtcccagcta ctcaggaggc  32220

tgaggtggga ggatcctttg agcccaagag atcaaggctg cagtgagcca tgtttgcacc  32280

actgcactcc agcctgggca acaaaacaag actctgtctc aaaaaaaaaa aaaaaaaaaa  32340

aaaggcaggg atggaggggg gaagagaaca cagcccagtt ttaggtggag ctgaggtggt  32400

ggcccagcca ggacaagtga agagtcttca gaggctgggt ttggagggcc gtgcatattc  32460

cggaggtact gctttcatac ttaaatgttt tcttgtaaaa ctcacacctg taatcccagc  32520

actttgggag gccaaggtgg gcggatcatc tgaggtcggg ggttcaagac caacctgacc  32580

aacatggaga aaccccgtct actaaaaata caaaaaatta gccaggtgtg gtgacacatg  32640

cctgtaatcc cagctactcg ggaggctgag gtaggagaat tgcttgaacc tgggaggcgg  32700

aagttgtggt gagctgagat cgtgccatta cacttcagcc tgggcaacaa gagcaaaact  32760

ccatctcaaa caaaactaaa ctaaactaaa ctaaagggtt ctatcgagaa gatgggctgc  32820

acgtgatggc tcacacctag actcccagcg cttcaggagg ccgaggtgga aggatcactt  32880

gaggccagga gttcaagatc tgcctgggca acatagcaag accctgtttt tacccaaaaa  32940

ataaaaaaat tacccagatg ctgtggtgtg tgcctgtagt accagctact gagaggctga  33000

ggcaggagga ccgcttgagc ctgggaggtc aaggctgcag tgagctgtga tcgtgccact  33060

gcactccagc ctgggtgaca cagcaagacc ttgtctcaaa aataaataaa ac          33112
```

<210> SEQ ID NO 4
<211> LENGTH: 597
<212> TYPE: PRT
<213> ORGANISM: Homo sapiens

<400> SEQUENCE: 4

```
Arg Cys Cys Asp Cys Ser Ala Ser Leu Ser His Gln Tyr Tyr Glu Lys
 1               5                  10                  15

Asp Gly Gln Leu Phe Cys Lys Lys Asp Tyr Trp Ala Arg Tyr Gly Glu
            20                  25                  30

Ser Cys His Gly Cys Ser Glu Gln Ile Thr Lys Gly Leu Val Met Val
        35                  40                  45

Ala Gly Glu Leu Lys Tyr His Pro Glu Cys Phe Ile Cys Leu Thr Cys
    50                  55                  60
```

-continued

```
Gly Thr Phe Ile Gly Asp Gly Asp Thr Tyr Thr Leu Val Glu His Ser
65                  70                  75                  80

Lys Leu Tyr Cys Gly His Cys Tyr Tyr Gln Thr Val Val Thr Pro Val
                85                  90                  95

Ile Glu Gln Ile Leu Pro Asp Ser Pro Gly Ser His Leu Pro His Thr
            100                 105                 110

Val Thr Leu Val Ser Ile Pro Ala Ser Ser His Gly Lys Arg Gly Leu
        115                 120                 125

Ser Val Ser Ile Asp Pro Pro His Gly Pro Pro Gly Cys Gly Thr Glu
    130                 135                 140

His Ser His Thr Val Arg Val Gln Gly Val Asp Pro Gly Cys Met Ser
145                 150                 155                 160

Pro Asp Val Lys Asn Ser Ile His Val Gly Asp Arg Ile Leu Glu Ile
                165                 170                 175

Asn Gly Thr Pro Ile Arg Asn Val Pro Leu Asp Glu Ile Asp Leu Leu
            180                 185                 190

Ile Gln Glu Thr Ser Arg Leu Leu Gln Leu Thr Leu Glu His Asp Pro
        195                 200                 205

His Asp Thr Leu Gly His Gly Leu Gly Pro Glu Thr Ser Pro Leu Ser
    210                 215                 220

Ser Pro Ala Tyr Thr Pro Ser Gly Glu Ala Gly Ser Ser Ala Arg Gln
225                 230                 235                 240

Lys Pro Val Leu Arg Ser Cys Ser Ile Asp Arg Ser Pro Gly Ala Gly
                245                 250                 255

Ser Leu Gly Ser Pro Ala Ser Gln Arg Lys Asp Leu Gly Arg Ser Glu
            260                 265                 270

Ser Leu Arg Val Val Cys Arg Pro His Arg Ile Phe Arg Pro Ser Asp
        275                 280                 285

Leu Ile His Gly Glu Val Leu Gly Lys Gly Cys Phe Gly Gln Ala Ile
    290                 295                 300

Lys Val Thr His Arg Glu Thr Gly Glu Val Met Val Met Lys Glu Leu
305                 310                 315                 320

Ile Arg Phe Asp Glu Glu Thr Gln Arg Thr Phe Leu Lys Glu Val Lys
                325                 330                 335

Val Met Arg Cys Leu Glu His Pro Asn Val Leu Lys Phe Ile Gly Val
            340                 345                 350

Leu Tyr Lys Asp Lys Arg Leu Asn Phe Ile Thr Glu Tyr Ile Lys Gly
        355                 360                 365

Gly Thr Leu Arg Gly Ile Ile Lys Ser Met Asp Ser Gln Tyr Pro Trp
    370                 375                 380

Ser Gln Arg Val Ser Phe Ala Lys Asp Ile Ala Ser Gly Met Ala Tyr
385                 390                 395                 400

Leu His Ser Met Asn Ile Ile His Arg Asp Leu Asn Ser His Asn Cys
                405                 410                 415

Leu Val Arg Glu Asn Lys Asn Val Val Val Ala Asp Phe Gly Leu Ala
            420                 425                 430

Arg Leu Met Val Asp Glu Lys Thr Gln Pro Glu Gly Leu Arg Ser Leu
        435                 440                 445

Lys Lys Pro Asp Arg Lys Lys Arg Tyr Thr Val Val Gly Asn Pro Tyr
    450                 455                 460

Trp Met Ala Pro Glu Met Ile Asn Gly Arg Ser Tyr Asp Glu Lys Val
465                 470                 475                 480
```

-continued

Asp Val Phe Ser Phe Gly Ile Val Leu Cys Glu Ile Ile Gly Arg Val
                485                 490                 495

Asn Ala Asp Pro Asp Tyr Leu Pro Arg Thr Met Asp Phe Gly Leu Asn
            500                 505                 510

Val Arg Gly Phe Leu Asp Arg Tyr Cys Pro Pro Asn Cys Pro Pro Ser
        515                 520                 525

Phe Phe Pro Ile Thr Val Arg Cys Cys Asp Leu Asp Pro Glu Lys Arg
    530                 535                 540

Pro Ser Phe Val Lys Leu Glu His Trp Leu Glu Thr Leu Arg Met His
545                 550                 555                 560

Leu Ala Gly His Leu Pro Leu Gly Pro Gln Leu Glu Gln Leu Asp Arg
                565                 570                 575

Gly Phe Trp Glu Thr Tyr Arg Arg Gly Glu Ser Gly Leu Pro Ala His
            580                 585                 590

Pro Glu Val Pro Asp
        595

<210> SEQ ID NO 5
<211> LENGTH: 3003
<212> TYPE: DNA
<213> ORGANISM: Homo sapiens
<220> FEATURE:
<221> NAME/KEY: misc_feature
<222> LOCATION: (1)...(3003)
<223> OTHER INFORMATION: n = A,T,C or G

<400> SEQUENCE: 5
gaagcagctg gtctggccac ccctgccctc ccttagacct ccagagcccc cagtgtagcc 60
acagaggatg ctgttggctt cagccccaag aagacgccgc ttcctccaga gggctaagtg 120
ttgtgactgc agtgcctccc tgtcgcacca gtactatgag aaggatgggc agctcttctg 180
caagaaggac tactgggccc gctatggcga gtcctgccat gggtgctctg agcaaatcac 240
caagggactg gttatggtgg ctggggagct gaagtaccac cccgagtgtt tcatctgcct 300
cacgtgtggg acctttatcg gtgacgggga cacctacacg ctggtggagc actccaagct 360
gtactgcggg cactgctact accagactgt ggtgaccccc gtcatcgagc agatcctgcc 420
tgactcccct ggctcccacc tgccccacac cgtcaccctg gtgtccatcc cagcctcatc 480
tcatggcaag cgtggacttt cagtctccat tgaccccccg cacggcccac cgggctgtgg 540
caccgagcac tcacacaccg tccgcgtcca gggagtggat ccgggctgca tgagcccaga 600
tgtgaagaat tccatccacg tcggagaccg gatcttggaa atcaatggca cgcccatccg 660
aaatgtgccc ctggacgaga ttgacctgct gattcaggaa accagccgcc tgctccagct 720
gaccctcgag catgaccctc acgatacact gggccacggg ctggggcctg agaccagccc 780
cctgagctct ccggcttata ctcccagcgg ggaggcgggc agctctgccc ggcagaaacc 840
tgtcttgagg agctgcagca tcgacaggtc tccgggcgct ggctcactgg gctccccggc 900
ctcccagcgc aaggacctgg gtcgctctga gtccctccgc gtagtctgcc ggccacaccg 960
catcttccgg ccgtcggacc tcatccacgg ggaggtgctg ggcaagggct gcttcggcca 1020
ggctatcaag gtgacacacc gtgagacagg tgaggtgatg gtgatgaagg agctgatccg 1080
gttcgacgag gagacccaga ggacgttcct caaggaggtg aaggtcatgc gatgcctgga 1140
acaccccaac gtgctcaagt tcatcggggt gctctacaag gacaagaggc tcaacttcat 1200
cactgagtac atcaagggcg gcacgctccg gggcatcatc aagagcatgg acagccagta 1260
cccatggagc cagagagtga gctttgccaa ggacatcgca tcagggatgg cctacctcca 1320

-continued

```
ctccatgaac atcatccacc gagacctcaa ctcccacaac tgcctggtcc gcgagaacaa   1380
gaatgtggtg gtggctgact tcgggctggc gcgtctcatg gtggacgaga agactcagcc   1440
tgagggcctg cggagcctca agaagccaga ccgcaagaag cgctacaccg tggtgggcaa   1500
cccctactgg atggcacctg agatgatcaa cggccgcagc tatgatgaga aggtggatgt   1560
gttctccttt gggatcgtcc tgtgcgagat catcgggcgg gtgaacgcag accctgacta   1620
cctgccccgc accatggact ttggcctcaa cgtgcgagga ttcctggacc gctactgccc   1680
cccaaactgc cccccgagct tcttccccat caccgtgcgc tgttgcgatc tggaccccga   1740
gaagaggcca tcctttgtga agctggaaca ctggctggag accctccgca tgcacctggc   1800
cggccacctg ccactgggcc cacagctgga gcagctggac agaggtttct gggagaccta   1860
ccggcgcggc gagagcggac tgcctgccca ccctgaggtc cccgactgag ccagggccac   1920
tcagctgccc ctgtccccac ctctggagaa tccaccccca ccagattcct ccgcgggagg   1980
tggccctcag ctgggacagt ggggacccag gcttctcctc agagccaggc cctgacttgc   2040
cttctcccac cccgtggacc gcttcccctg ccttctctct gccgtggccc agagccggcc   2100
cagctgcaca cacacaccat gctctcgccc tgctgtaacc tctgtcttgg cagggctgtc   2160
ccctcttgct tctccttgca tgagctggag ggcctgtgtg agttacgccc ctttccacac   2220
gccgctgccc cagcaaccct gttcacgctc cacctgtctg gtccatagct ccctggaggc   2280
tgggccagga ggcagcctcc gaaccatgcc ccatataacg cttgggtgcg tgggagggcg   2340
cacatcaggg cagaggccaa gttccaggtg tctgtgttcc caggaaccaa atggggagtc   2400
tggggcccgt tttcccccca gggggtgtct aggtagcaac aggtatcgag gactctccaa   2460
acccccaaag cagagagagg gctgatccca tggggcggag gtccccagtg gctgagcaaa   2520
cagcccccttc tctcgctttg ggtcnnnnnn nngtttcttt cttaaagcca ctttagtgag   2580
aagcaggtac caagcctcag ggtgaagggg gtcccttgag ggagcgtgga gctgcggtgc   2640
cctggccggc gatggggagg agccggctcc ggcagtgaga ggataggcac agtggaccgg   2700
gcaggtgtcc accagcagct cagcccctgc agtcatctca gagccccttc ccgggcctct   2760
cccccaaggc tccctgcccc tcctcatgcc cctctgtcct ctgcgttttt tctgtgtaat   2820
ctatttttta agaagagttt gtattatttt ttcatacggc tgcagcagca gctgccaggg   2880
gcttgggatt ttatttttgt ggcgggcggg ggtgggaggg ccattttgtc actttgcctc   2940
agttgagcat ctaggaagta ttaaaactgt gaagctttct cagtgcactt tgaacctgga   3000
aaa                                                                 3003
```

<210> SEQ ID NO 6
<211> LENGTH: 3003
<212> TYPE: DNA
<213> ORGANISM: Homo sapiens

<400> SEQUENCE: 6

```
gaagcagctg gtctggccac ccctgccctc ccttagacct ccagagcccc cagtgtagcc     60
acagaggatg ctgttggctt cagccccaag aagacgccgc ttcctccaga gggctaagtg    120
ttgtgactgc agtgcctccc tgtcgcacca gtactatgag aaggatgggc agctcttctg    180
caagaaggac tactgggccc gctatggcga gtcctgccat gggtgctctg agcaaatcac    240
caagggactg gttatggtgg ctggggagct gaagtaccac cccgagtgtt tcatctgcct    300
cacgtgtggg acctttatcg gtgacgggga cacctacacg ctggtggagc actccaagct    360
```

-continued

```
gtactgcggg cactgctact accagactgt ggtgaccccc gtcatcgagc agatcctgcc    420
tgactcccct ggctcccacc tgccccacac cgtcaccctg gtgtccatcc cagcctcatc    480
tcatggcaag cgtggacttt cagtctccat tgaccccccg cacggcccac cgggctgtgg    540
caccgagcac tcacacaccg tccgcgtcca gggagtggat ccgggctgca tgagcccaga    600
tgtgaagaat tccatccacg tcggagaccg gatcttggaa atcaatggca cgcccatccg    660
aaatgtgccc ctggacgaga ttgacctgct gattcaggaa accagccgcc tgctccagct    720
gaccctcgag catgaccctc acgatacact gggccacggg ctggggcctg agaccagccc    780
cctgagctct ccggcttata ctcccagcgg ggaggcgggc agctctgccc ggcagaaacc    840
tgtcttgagg agctgcagca tcgacaggtc tccgggcgct ggctcactgg gctccccggc    900
ctcccagcgc aaggacctgg gtcgctctga gtccctccgc gtagtctgcc ggccacaccg    960
catcttccgg ccgtcggacc tcatccacgg ggaggtgctg ggcaagggct gcttcggcca   1020
ggctatcaag gtgacacacc gtgagacagg tgaggtgatg gtgatgaagg agctgatccg   1080
gttcgacgag gagacccaga ggacgttcct caaggaggtg aaggtcatgc gatgcctgga   1140
acaccccaac gtgctcaagt tcatcggggt gctctacaag gacaagaggc tcaacttcat   1200
cactgagtac atcaagggcg gcacgctccg ggcatcatc  aagagcatgg acagccagta   1260
cccatggagc cagagagtga gctttgccaa ggacatcgca tcagggatgg cctacctcca   1320
ctccatgaac atcatccacc gagacctcaa ctcccacaac tgcctggtcc gcgagaacaa   1380
gaatgtggtg gtggctgact tcgggctggc gcgtctcatg gtggacgaga agactcagcc   1440
tgagggcctg cggagcctca agaagccaga ccgcaagaag cgctacaccg tggtgggcaa   1500
cccctactgg atggcacctg agatgatcaa cggccgcagc tatgatgaga aggtggatgt   1560
gttctccttt gggatcgtcc tgtgcgagat catcgggcgg gtgaacgcag accctgacta   1620
cctgccccgc accatggact ttggcctcaa cgtgcgagga ttcctggacc gctactgccc   1680
cccaaactgc cccccgagct tcttccccat caccgtgcgc tgttgcgatc tggaccccga   1740
gaagaggcca tcctttgtga agctggaaca ctggctggag accctccgca tgcacctggc   1800
cggccacctg ccactgggcc cacagctgga gcagctggac agaggtttct gggagaccta   1860
ccggcgcggc gagagcggac tgcctgccca ccctgaggtc cccgactgag ccagggccac   1920
tcagctgccc ctgtccccac ctctggagaa tccacccccca ccagattcct ccgcgggagg   1980
tggccctcag ctgggacagt ggggacccag gcttctcctc agagccaggc cctgacttgc   2040
cttctcccac cccgtggacc gcttcccctg ccttctctct gccgtggccc agagccggcc   2100
cagctgcaca cacacaccat gctctcgccc tgctgtaacc tctgtcttgg cagggctgtc   2160
ccctcttgct tctccttgca tgagctggag ggcctgtgtg agttacgccc ctttccacac   2220
gccgctgccc cagcaaccct gttcacgctc cacctgtctg gtccatagct ccctggaggc   2280
tgggccagga ggcagcctcc gaaccatgcc ccatataacg cttgggtgcg tgggagggcg   2340
cacatcaggg cagaggccaa gttccaggtg tctgtgttcc caggaaccaa atggggagtc   2400
tggggcccgt tttcccccca gggggtgtct aggtagcaac aggtatcgag gactctccaa   2460
acccccaaag cagagagagg gctgatccca tggggcggag gtccccagtg gctgagcaaa   2520
cagccccttc tctcgctttg ggtctttttt ttgtttcttt cttaaagcca ctttagtgag   2580
aagcaggtac caagcctcag ggtgaagggg gtcccttgag ggagcgtgga gctgcggtgc   2640
cctggccggc gatggggagg agccggctcc ggcagtgaga ggataggcac agtggaccgg   2700
gcaggtgtcc accagcagct cagcccctgc agtcatctca gagccccttc ccgggcctct   2760
```

-continued

```
cccccaaggc tccctgcccc tcctcatgcc cctctgtcct ctgcgttttt tctgtgtaat   2820

ctatttttta agaagagttt gtattatttt ttcatacggc tgcagcagca gctgccaggg   2880

gcttgggatt ttatttttgt ggcgggcggg ggtgggaggg ccattttgtc actttgcctc   2940

agttgagcat ctaggaagta ttaaaactgt gaagctttct cagtgcactt tgaacctgga   3000

aaa                                                                 3003
```

<210> SEQ ID NO 7
<211> LENGTH: 816
<212> TYPE: DNA
<213> ORGANISM: Homo sapiens

<400> SEQUENCE: 7

```
gaagcagctg gtctggccac ccctgccctc ccttagacct ccagagcccc cagtgtagcc     60

acagaggatg ctgttggctt cagccccaag aagacgccgc ttcctccaga gggctaagtg    120

ttgtgactgc agtgcctccc tgtcgcacca gtactatgag aaggatgggc agctcttctg    180

caagaaggac tactgggccc gctatggcga gtcctgccat gggtgctctg agcaaatcac    240

caagggactg gttatggtgg ctggggagct gaagtaccac cccgagtgtt tcatctgcct    300

cacgtgtggg acctttatcg gtgacgggga cacctacacg ctggtggagc actccaagct    360

gtactgcggg cactgctact accagactgt ggtgaccccc gtcatcgagc agatcctgcc    420

tgactcccct ggctcccacc tgccccacac cgtcaccctg gtgtccatcc cagcctcatc    480

tcatggcaag cgtggacttt cagtctccat tgaccccccg cacggcccac cgggctgtgg    540

caccgagcac tcacacaccg tccgcgtcca gggagtggat ccgggctgca tgagcccaga    600

tgtgaagaat tccatccacg tcggagaccg gatcttggaa atcaatggca cgcccatccg    660

aaatgtgccc ctggacgaga ttgacctgct gattcaggaa accagccgcc tgctccagct    720

gaccctcgag catgaccctc acgatacact gggccacggg ctggggcctg agaccagccc    780

cctgagctct ccggcttata ctcccagcgg ggaggc                              816
```

<210> SEQ ID NO 8
<211> LENGTH: 823
<212> TYPE: DNA
<213> ORGANISM: Homo sapiens

<400> SEQUENCE: 8

```
gaagcagctg gtctggccac ccctgccctc ccttagacct ccagagcccc cagtgtagcc     60

acagaggatg ctgttggctt cagccccaag aagacgccgc ttcctccaga gggctaagtg    120

ttgtgactgc agtgcctccc tgtcgcacca gtactatgag aaggatgggc agctcttctg    180

caagaaggac tactgggccc gctatggcga gtcctgccat gggtgctctg agcaaatcac    240

caagggactg gttatggtgg ctggggagct gaagtaccac cccgagtgtt tcatctgcct    300

cacgtgtggg acctttatcg gtgacgggga cacctacacg ctggtggagc actccaagct    360

gtactgcggg cactgctact accagactgt ggtgaccccc gtcatcgagc agatcctgcc    420

tgactcccct ggctcccacc tgccccacac cgtcaccctg gtgtccatcc cagcctcatc    480

tcatggcaag cgtggacttt cagtctccat tgaccccccg cacggcccac cgggctgtgg    540

caccgagcac tcacacaccg tccgcgtcca gggagtggat ccgggctgca tgagcccaga    600

tgtgaagaat tccatccacg tcggagaccg gatcttggaa atcaatggca cgcccatccg    660

aaatgtgccc ctggacgaga ttgactgctg attcaggaaa ccagccgcac tgctccagac    720
```

-continued

```
tgaccctcga gcatgaccct cacgatacaa ctgggacacg gcggctgggg ccttgagacc    780

agcccccctg agactctccg gcttatactc ccagcgggga ggc                      823
```

ISOLATED HUMAN KINASE PROTEINS, NUCLEIC ACID MOLECULES ENCODING HUMAN KINASE PROTEINS, AND USES THEREOF

This application claims priority to U.S. Provisional application 60/380,134 filed May 16, 2002.

FIELD OF THE INVENTION

The present invention is in the field of kinase proteins that are related to the LIM domain kinase subfamily, recombinant DNA molecules, and protein production. The present invention specifically provides a novel alternative splice form of a LIM domain kinase. The present invention provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

LIM Domain Kinases (LIMKs)

The novel human protein provided by the present invention is a novel LIM domain kinase (LIMK) alternative splice form. The novel LIMK splice form of the present invention shares the highest degree of sequence similarity with LIMK1, isoform 1 (see the amino acid sequence alignment of SEQ ID NO:2 with LIMK1 in FIG. 2).

LIMK1 contains a protein kinase domain in the C-terminal half of the protein, and two repeats of cysteine-rich LIM/double zinc finger motifs at the N-terminus, with an intervening proline-serine-rich region that contains casein kinase and map kinase recognition sites (Mizuno et al., *Oncogene* 1994 June; 9(6):1605–12). The LIM domain is thought to participate in protein-protein interactions by binding to other LIM motifs. LIM domains are highly conserved cysteine-rich structures that contain 2 zinc fingers. Approximately 40 eukaryotic LIM-containing proteins are known to exist. Because the LIM domain is often present in the homeodomain-containing transcriptional regulators and oncogenic nuclear proteins, LIMK1 is thought to play a role in developmental or oncogenic processes through interactions with such LIM-containing proteins (Mizuno et al., *Oncogene* 1994 June; 9(6):1605–12). LIMK1 is also thought to be a component of an intracellular signaling pathway and is thought to be involved in brain development (Tassabehji et al., *Nature Genet.* 13: 272–273, 1996). Consistent with this involvement in the brain, virtual northern blot analysis indicates expression of the present novel LIMK splice form in brain neuroblastoma cells and hypothalamus tissue (see FIG. 1)

In addition to its association with oncogenic processes, intracellular signaling, brain development, LIMK has specifically been found to be deleted in Williams syndrome, and LIMK1 is likely to be responsible for the unexplained neurologic features of Williams syndrome (Tassabehji et al., *Nat Genet* 1996 July; 13(3):272–3). Furthermore, LIMK1 hemizygosity has been implicated in the impaired visuospatial constructive cognition of Williams syndrome (Frangiskakis et al., *Cell* 86: 59–69, 1996).

Additionally, LIMK1 has been identified as a potent activator of serum response factor (SRF; involved in regulating transcription of numerous serum-inducible and muscle-specific genes). SRF activation by LIMK1 depends on the ability of LIMK1 to regulate actin treadmilling (Sotiropoulos et al., *Cell* 98: 159–169, 1999).

LIMK is phosphorylated and activated by ROCK, which is a downstream effector of Rho. LIMK phosphorylates cofilin, thereby reducing the actin-depolymerizing activity of cofilin. This pathway leads to Rho-induced reorganization of the actin cytoskeleton (Maekawa et al., *Science* 285: 895–898, 1999).

Thus, it is clear that novel LIMK proteins and alternative splice forms, particularly those related to LIMK1, have valuable commercial utilities related to the treatment and diagnosis of such pathologies as brain/neurological disorders, cancers, and disorders associated with serum response factor.

For a further review of LIMKs, see Bernard et al., *Genomics* 35: 593–596, 1996; Maekawa et al., *Science* 285: 895–898, 1999; Mao et al., *Cytogenet. Cell Genet.* 74: 190–191, 1996; Okano et al., *J. Biol. Chem.* 270: 31321–31330, 1995; Proschel et al., *Oncogene* 11: 1271–1281, 1995; Osborne et al., *Genomics* 36 (2), 328–336 (1996); and Edwards et al., *J. Biol. Chem.* 274 (16), 11352–11361 (1999).

Kinase proteins, particularly members of the LIM domain kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the LIM domain kinase subfamily.

SUMMARY OF THE INVENTION

The present invention is based in part on the identification of amino acid sequences of human kinase peptides and proteins that are related to the LIM domain kinase subfamily, as well as allelic variants and other mammalian orthologs thereof. The present invention specifically provides a novel alternative splice form of a LIM domain kinase. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone.

DESCRIPTION OF THE FIGURE SHEETS

FIG. 1A–1B provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone.

FIG. 2A–2I provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence. FIG. 2 also provides EST alignments that support the alternative 5' end of the novel splice form of the present invention.

FIG. 3A–3R provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 26 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the LIM domain kinase subfamily. Utilizing these sequences, additional genomic sequences were assembled and transcript and/or cDNA sequences were isolated and characterized. Based on this analysis, the present invention provides amino acid sequences of human kinase peptides and proteins that represent a novel LIM domain kinase alternative splice form, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the LIM domain kinase subfamily and the expression pattern observed. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known LIM domain kinase family or subfamily of kinase proteins.

Specific Embodiments

Peptide Molecules

The present invention provides nucleic acid sequences that encode protein molecules that have been identified as being members of the kinase family of proteins and are related to the LIM domain kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated in FIG. 3, the map position was determined to be on chromosome 7.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated in FIG. 3, the map position was determined to be on chromosome 7. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that were identified at 26 different nucleotide positions in the gene encoding the kinase proteins of the present invention.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis. A large percentage of pharmaceutical agents are being developed that modulate the activity of kinase proteins, particularly members of the LIM domain kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. Such uses can readily be determined using the information provided herein, that which is known in the art, and routine experimentation.

The proteins of the present invention (including variants and fragments that may have been disclosed prior to the present invention) are useful for biological assays related to kinases that are related to members of the LIM domain kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated in FIG. 3, the map position was determined to be on chromosome 7.

FIG. 3 provides information on SNPs that were identified at 26 different nucleotide positions in the gene encoding the kinase proteins of the present invention.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 26 different nucleotide positions.

The probe can correspond to any sequence along the entire length of the nucleic acid molecules provided in the Figures. Accordingly, it could be derived from 5' noncoding regions, the coding region, and 3'. noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated in FIG. 3, the map position was determined to be on chromosome 7.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that were identified at 26 different nucleotide positions in the gene encoding the kinase proteins of the present invention. As indicated in FIG. 3, the map position was determined to be on chromosome 7. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that were identified at 26 different nucleotide positions in the gene encoding the kinase proteins of the present invention.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1. indicates that kinase proteins of the present invention are expressed in brain neuroblastoma, hypothalamus, liver adenocarcinoma, whole embryo (especially in the head), thyroid gland, uterus leiomyosarcoma, renal cell adenocarcinoma, duodenal adenocarcinoma, hypernephrona, retinal epithelium, and hip bone, as indicated by virtual northern blot analysis. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that were identified at 26 different nucleotide positions in the gene encoding the kinase proteins of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in*

*Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, *Vaccinia* viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule, wherein the nucleotide sequence of said nucleic acid molecule consists of a nucleotide sequence selected from the group consisting of:

(a) a nucleotide sequence that encodes a polypeptide having an amino acid sequence comprising SEQ ID NO:2;

(b) SEQ ID NO:1;

(c) SEQ ID NO:3;

(d) nucleotides 2068–30111 of SEQ ID NO:3; and (e) a nucleotide sequence that is completely complementary to the nucleotide sequence of (a), (b), (c), or (d).

2. An isolated nucleic acid molecule comprising a nucleotide sequence selected from the group consisting of:

(a) a transcript or cDNA sequence that encodes a polypeptide having an amino acid sequence comprising SEQ ID NO:2;

(b) SEQ ID NO:1; and (c) a nucleotide sequence that is completely complementary to the nucleotide sequence of (a) or (b).

3. An isolated nucleic acid molecule, wherein the nucleotide sequence of said nucleic acid molecule consists of SEQ ID NO:1 or the complete complement thereof.

4. An isolated nucleic acid molecule having a nucleotide sequence comprising SEQ ID NO:1 or the complete complement thereof.

5. An isolated nucleic acid molecule, wherein the nucleotide sequence of said nucleic acid molecule consists of SEQ ID NO:3 or the complete complement thereof.

6. An isolated nucleic acid molecule, wherein the nucleotide sequence of said nucleic acid molecule consists of nucleotides 2068–30111 of SEQ ID NO:3 or the complete complement thereof.

7. An isolated nucleic acid molecule, wherein the nucleotide sequence of said nucleic acid molecule consists of a nucleotide sequence that encodes a polypeptide comprising SEQ ID NO:2, or the complete complement of said nucleotide sequence.

8. An isolated transcript or cDNA nucleic acid molecule comprising a nucleotide sequence that encodes a polypeptide comprising SEQ ID NO:2, or the complete complement of said nucleotide sequence.

9. A nucleic acid construct comprising the nucleic acid molecule of claim 1 or 2 fused to a heterologous nucleotide sequence.

10. The nucleic acid construct of claim 9, wherein the heterologous nucleotide sequence encodes a heterologous amino acid sequence.

11. A vector comprising the nucleic acid molecule of claim 1 or 2.

12. An isolated host cell containing the vector of claim 11.

13. A process for producing a polypeptide, the process comprising culturing the host cell of claim 12 under conditions sufficient for the production of said polypeptide, and recovering said polypeptide.

14. The vector of claim 11, wherein said vector is selected from the group consisting of a plasmid, a virus, and a bacteriophage.

15. The vector of claim 11, wherein said nucleic acid molecule is inserted into said vector in proper orientation and correct reading frame such that a polypeptide comprising SEQ ID NO:2 is expressed by a cell transformed with said vector.

16. The vector of claim 15, wherein said isolated nucleic acid molecule is operatively linked to a promoter sequence.

* * * * *